US 8,778,921 B2

(12) United States Patent
Porter et al.

(10) Patent No.: US 8,778,921 B2
(45) Date of Patent: Jul. 15, 2014

(54) ANSAMYCIN HYDROQUINONE COMPOSITIONS

(75) Inventors: James R. Porter, Rowley, MA (US); Sonali Puri, Ashland, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 4 days.

(21) Appl. No.: 13/124,461

(22) PCT Filed: Oct. 15, 2009

(86) PCT No.: PCT/US2009/060819
§ 371 (c)(1),
(2), (4) Date: Jun. 3, 2011

(87) PCT Pub. No.: WO2010/045442
PCT Pub. Date: Apr. 22, 2010

(65) Prior Publication Data
US 2011/0263563 A1    Oct. 27, 2011

Related U.S. Application Data

(60) Provisional application No. 61/105,648, filed on Oct. 15, 2008.

(51) Int. Cl.
| C07D 225/04 | (2006.01) |
| A61K 31/395 | (2006.01) |
| A61K 31/7016 | (2006.01) |
| A61K 45/06 | (2006.01) |
| A61K 9/10 | (2006.01) |
| A61K 9/19 | (2006.01) |
| A61K 9/50 | (2006.01) |

(52) U.S. Cl.
CPC . *A61K 45/06* (2013.01); *A61K 9/10* (2013.01); *A61K 9/19* (2013.01); *A61K 9/5026* (2013.01); *A61K 31/395* (2013.01)
USPC ........ 514/183; 514/229.8; 514/375; 540/456; 540/461; 540/462

(58) Field of Classification Search
None
See application file for complete search history.

(56) References Cited

U.S. PATENT DOCUMENTS

| 4,261,989 | A | * | 4/1981 | Sasaki et al. | 514/183 |
| 4,762,857 | A | | 8/1988 | Bollin, Jr. et al. | |
| 4,792,443 | A | * | 12/1988 | Filomeno | 424/62 |
| 5,387,584 | A | | 2/1995 | Schnur | |
| 5,932,566 | A | | 8/1999 | Schnur et al. | |
| 6,872,715 | B2 | | 3/2005 | Santi et al. | |
| 6,878,526 | B1 | | 4/2005 | Warenius et al. | |
| 7,465,718 | B2 | | 12/2008 | Zhang et al. | |
| 7,608,613 | B2 | * | 10/2009 | Adams et al. | 514/183 |
| 7,767,663 | B2 | * | 8/2010 | Adams et al. | 514/183 |
| 8,003,634 | B2 | * | 8/2011 | Adams et al. | 514/183 |
| 2004/0053909 | A1 | | 3/2004 | Snader et al. | |
| 2005/0227955 | A1 | * | 10/2005 | Adams et al. | 514/183 |
| 2006/0019941 | A1 | * | 1/2006 | Adams et al. | 514/183 |
| 2006/0205705 | A1 | | 9/2006 | Ross et al. | |
| 2007/0048323 | A1 | | 3/2007 | Rubin | |
| 2007/0129342 | A1 | | 6/2007 | Mansfield et al. | |
| 2008/0139582 | A1 | | 6/2008 | Honigberg et al. | |

FOREIGN PATENT DOCUMENTS

| EP | 0270317 | 6/1988 |
| EP | 0 920 873 | 6/1999 |
| GB | 2 106 111 A | 4/1993 |
| JP | WO 2007/001049 | 1/2007 |
| WO | WO-93/14215 | 7/1993 |
| WO | WO-95/01342 | 1/1995 |
| WO | WO-96/40265 | 12/1996 |
| WO | WO-03/013430 | 2/2003 |
| WO | WO-03/026571 | 4/2003 |
| WO | WO-03/066005 | 8/2003 |

(Continued)

OTHER PUBLICATIONS

Clevenger, R. C. et al., "Design, Synthesis, and Evaluation of a Radicicol and Geldamycin Chimera, Radamide", Organic Letters, 6(24):4459-4462 (2004).
Fritz et al., "Comparison of the cellular and biochemical properties of ansamycin and non-ansamycin based Hsp90 inhibitors," Infinity Pharmaceuticals, Inc., Presented by Christian Fritz on Oct. 22, 2008 at the 20th EORTC-NCI-AACR Symposium on "Molecular Targets and Cancer Therapeutics," (Geneva, Switzerland, Oct. 21-24, 2008).
Fumo et al., "17-Allylamino-17-demethoxygeldanamycin (17-AAG) is effective in down-regulating mutated, constitutively activated KIT protein in human mast cells," Blood, published online Oct. 9, 2003.

(Continued)

*Primary Examiner* — Jefferey S. Lundgren
*Assistant Examiner* — Michael Schmitt
(74) *Attorney, Agent, or Firm* — Dana M. Gordon; Foley Hoag LLP

(57) ABSTRACT

Aspects of the present invention provide compositions comprising a sulfur containing compound and a compound of the formula (I); and also provide methods of their preparation and use.

26 Claims, 24 Drawing Sheets

(56) References Cited

FOREIGN PATENT DOCUMENTS

| WO | WO 03066005 A2 * | 8/2003 |
|---|---|---|
| WO | WO-04/000347 | 12/2003 |
| WO | WO-2004/082676 A1 | 9/2004 |
| WO | WO-2005/063714 | 4/2005 |
| WO | WO-2005/095347 | 10/2005 |
| WO | WO-2006/098761 | 9/2006 |
| WO | WO-2007/002093 | 1/2007 |
| WO | WO-2007/009007 | 1/2007 |
| WO | WO-2008/073424 A2 | 6/2008 |
| WO | WO-2008/128063 | 10/2008 |

OTHER PUBLICATIONS

Ge et al., "Design, Synthesis, and Biological Evaluation of Hydroquinone Derivatives of 17-Amino-17-demethoxygeldanamycin as Potent, Water-Soluble Inhibitors of Hsp90," J. Med. Chem. 49:4606-4615 (2006).
Guo, et al., "A Potential Role for NAD(P)H:quinine oxideductasel (NQO1) in the Mechanism of Action of the Hsp90 Inhibitors Geldanamycin and 17AAG" AACR Annual Meeting, Apr. 2005, vol. 46, 4936.
Guo, W. et al., "Formation of 17-Allylamino-Demethoxygeldanamycin (17-AAG) Hydroquinone by NAD(P)H:Quinone Oxireductase 1: Role of 17-AAG Hydroquinone in Heat Shock Protein 90 Inhibition", Cancer Res., 65(21):10006-10015 (2005).
Hostein et al., "Inhibition of Signal Transduction by the Hsp90 Inhibitor 17-Allylamino-17-demethoxygeldanamycin Results in Cytostasis and Apoptosis," Cancer Research, 61:4003-4009 (2001).
Hu, Z. et al., "Isolation and Characterization of Novel Geldanamycin Analogues", Journ. Antibiot, 57(7):421-428 (2004).
"Infinity Halts Ring Trial in Advanced Gastrointestinal Stromal Tumors," Infinity Pharmaceuticals, Inc., Press Release, Apr. 15, 2009.
"Infinity Provides Update on Phase 2 Signal-Finding Clinical Study of IPI-504 in Advanced Prostate Cancer," Infinity Pharmaceuticals, Inc. Press Release, Jul. 14, 2008.
Kelland, L. R. et al., "DT-Diaphorase Expression and Tumor Cell Sensitivity to 17-Allylamino, 17-demethoxygeldanamycin, an Inhibitor of Heat Shock Protein 90", Journ. of the Nat. Cancer Inst., 91(22):1940-1949 (1999).
Maroney et al., "Dihydroquinone Ansamycins: Toward Resolving the Conflict between Low in Vitro Affinity and High Cellular Potency of Geldanamycin Derivatives," Biochemistry, 45:5678-5685 (2006).
Melis, et al.; "Synchronous colorectal adenocarcinoma and gastrointestinal stromal tumor (GIST)"; Int. J. Colorectal Dis., 22:109-114 (2007).
Miller, et al., "Depletion of the erbB-2 Gene Product p185 by Benzoquinoid Ansamycins," Cancer Research, 54:2724-2730 (1994).
Mitsiades, C. S. et al., "Antimyeloma activity of heat shock protein-90 inhibition", Blood, 107(3):1092-1100 (2006).
Mitsiades, et al., "IPI-504: A Novel Hsp90 Inhibitor with in vitro and in vivo Antitumor Activity" Blood, 104:660A (2004).
O'Brien, P.J, "Molecular Mechanisms of Quinone Cytotoxicity," Chem.-Biol. Interactions, 80:1-41 (1991).
Oh et al., "A single arm Phase 2 trial of IPI-504 in patients with castration resistant prostate cancer (CRPC)," Abstract submitted Oct. 24, 2008, for the 2009 ASCO Genitourinary Cancers Symposium, Orlando, FL, Feb. 26-28, 2009.
Oku et al., "NMR and Quantum Chemical Study on the OH•••πand CH•••O Interactions between Trehalose and Unsaturated Fatty Acids: Implication for the Mechanism of Antioxidant Function of Trehalose," J. Am. Chem. Soc. 125:12739-12748 (2003).
Oku et al., "Combined NMR and Quantum Chemical Studies on the Interaction between Trehalose and Dienes Relevant to the Antioxidant Function of Trehalose," J. Phys. Chem. 109:3032-3040 (2005).
Onuoha et al., "Mechanistic Studies on Hsp90 Inhibition by Ansamycin Derivatives," J. Mol. Biol., 372:287-297 (2007).
Porter, James R, "Synthesis and Biological Evaluation of IPI-504, an Aqueous Soluble Analog of 17-AAG and Potent Inhibitor of Hsp90," Presentation by James Porter at ACS Meeting: MEDI-210, Mar. 29, 2006.
Palombella, et al., "Antitumor Activity of IPI-504, a novel Hsp90 Inhibitor in Multiple Myeloma" Blood, 104: Abstract 4922 (2004).
Reigner, et al., "Simultaneous Assay of Pentachlorophenol and Its Metabolite Tetrachlorohydroquinone, by Gas Chromatography Without Derivitation," J. Chromatography, 533:111-124 (1990).
Rubin, et al., "Gastrointestinal stromal tumour," Lancet, 369:1731-41 (2007).
Schnur, et al., "erbB-2 Oncogene Inhibition by Geldanamycin Derivatives: Synthesis, Mechanism of Action, and Structure-Activity Relationships," J. Med. Chem, 38:3813-3820 (1995).
Schnur, R. C. et al., "Inhibition of the Oncogene Product p. 185erbB-2 in Vitro and in Vivo by Geldanamycin and Dihydrogeldanamycin Derivatives", J. Med. Chem., 38:3806-3812 (1995).
Sydor et al., "Anti-tumor activity of a novel, water soluble Hsp90 inhibitor IPI-504 in multiple myeloma," Experimental and Molecular Therapeutics 55: Modulation of Protein Stability, Abstract #6160, Apr. 2005.
Sydor et al., "Development of 17-allylamino-17-demethoxygeldanamycin hydroquinone hydrochloride (IPI-504), an anti-cancer agent directed against Hsp90," PNAS, 103(46):1740817413 (2006).
International Search Report for PCT/US2009/060819 dated Dec. 15, 2009.
International Search Report for PCT/US2010/035403 dated Jul. 8, 2010.

* cited by examiner

ANSAMYCIN HYDROQUINONE COMPOSITIONS

RELATED APPLICATIONS

This application is a 371 national stage application based on Patent Cooperation Treaty Application serial number PCT/US2009/060819, filed Oct. 15, 2009; which claims the benefit of priority to U.S. Provisional Patent Application Ser. No. 61/105,648, filed Oct. 15, 2008.

BACKGROUND

Heat shock protein 90 (Hsp90) is a highly abundant mammalian protein, which is essential for cell viability and which exhibits dual chaperone functions. It plays a key role in the cellular stress-response by interacting with proteins after their native conformations have been altered by various environmental stresses, such as heat shock, thereby ensuring adequate protein-folding and preventing non-specific aggregation. Hsp90 may also play a role in buffering proteins against the effects of mutation, presumably by correcting the inappropriate folding of mutant proteins. Hsp90 also has an important regulatory role under normal physiological conditions and it is responsible for the conformational stability and maturation of a number of specific client proteins.

Hsp90 antagonists are currently being explored in a large number of biological contexts where a therapeutic effect may be obtained for a condition or disorder by inhibiting one or more aspects of Hsp90 activity. Although the primary focus of the research has been on proliferative disorders, such as cancers, other conditions have also been shown to be amenable to treatment using Hsp90 antagonists.

Geldanamycin is a macrocyclic lactam that is a member of the benzoquinone-containing ansamycin family of natural products. Geldanamycin's nanomolar potency and apparent selectivity for killing tumor cells, as well as the discovery that its primary target in mammalian cells is Hsp90, has stimulated interest in its development as an anti-cancer drug. However, the low solubility and association of hepatotoxicity with the administration of geldanamycin have led to difficulties in developing an appropriate composition for therapeutic applications. In particular, geldanamycin is poorly water soluble, making it difficult to deliver in therapeutically effective doses.

There have been considerable efforts to develop analogs of geldanamycin with reduced hepatotoxicity, increased aqueous solubility and comparable bioactivity. For example, geldanamycin analogs substituted at the 17-position with various amino groups ("17-amino-substituted geldanamycin analogs") such as 17-AAG have shown reduced hepatotoxicity while maintaining Hsp90 binding but still suffer from low aqueous solubility (for example, see U.S. Pat. Nos. 4,261, 989; 5,387,584; and 5,932,566). Examination of the corresponding hydroquinones has been limited as these compounds have generally been found to be unstable due to facile air oxidation (see Schnur et al., *J. Med. Chem.* (1995) 38:3813-3820 and Schnur et al., *J. Med. Chem.* (1995) 38:3806-3812).

SUMMARY OF THE INVENTION

The present invention provides compositions of hydroquinones of 17-amino-substituted geldanamycin analogs and also provides methods of their preparation and use.

For example, in one aspect, the present invention provides a composition comprising a sulfur-containing compound and a hydroquinone compound of the formula (I):

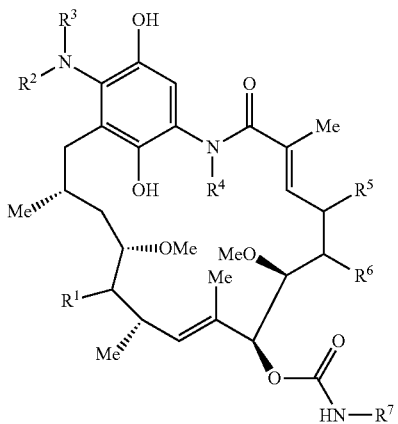

wherein $R^1$, $R^2$, $R^3$, $R^4$, $R^5$, $R^6$ and $R^7$ are as defined herein.

In another aspect, the present invention provides a pharmaceutical formulation comprising a composition, as described herein, and a pharmaceutically acceptable excipient.

In yet another aspect, the present invention provides a method for making a hydroquinone composition comprising:

(i) reducing a compound of formula (II):

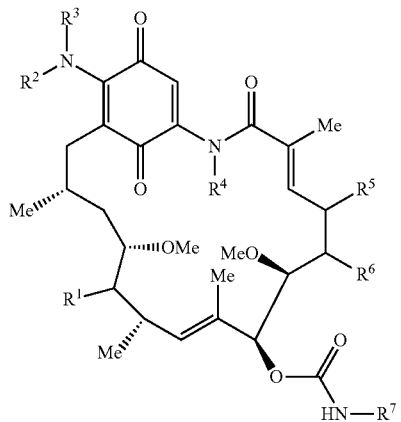

or a pharmaceutically acceptable salt thereof, to a compound of formula (I):

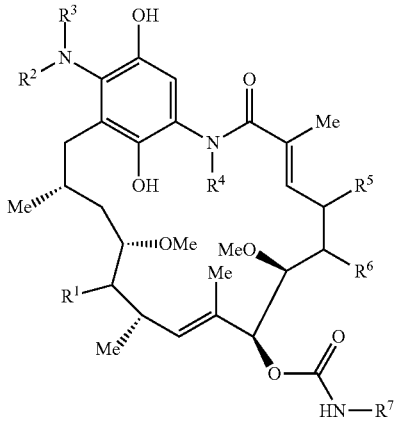

in the presence of a sulfur-containing compound,
wherein R$^1$, R$^2$, R$^3$, R$^4$, R$^5$, R$^6$ and R$^7$ are as defined herein, and (ii) isolating a precipitate, wherein the precipitate is a composition comprising a compound of formula (I) and a sulfur-containing compound.

In still yet another aspect, the present invention provides a method of treating a hyperproliferative disorder, such as cancer, comprising administering to a subject in need thereof a therapeutically effective amount of a composition or formulation of the present invention.

Details of the invention are set forth in the accompanying Description and Examples as described herein. Other features, objects, and advantages of the invention will be apparent from this description and from the claims.

DEFINITIONS

Figure 1:
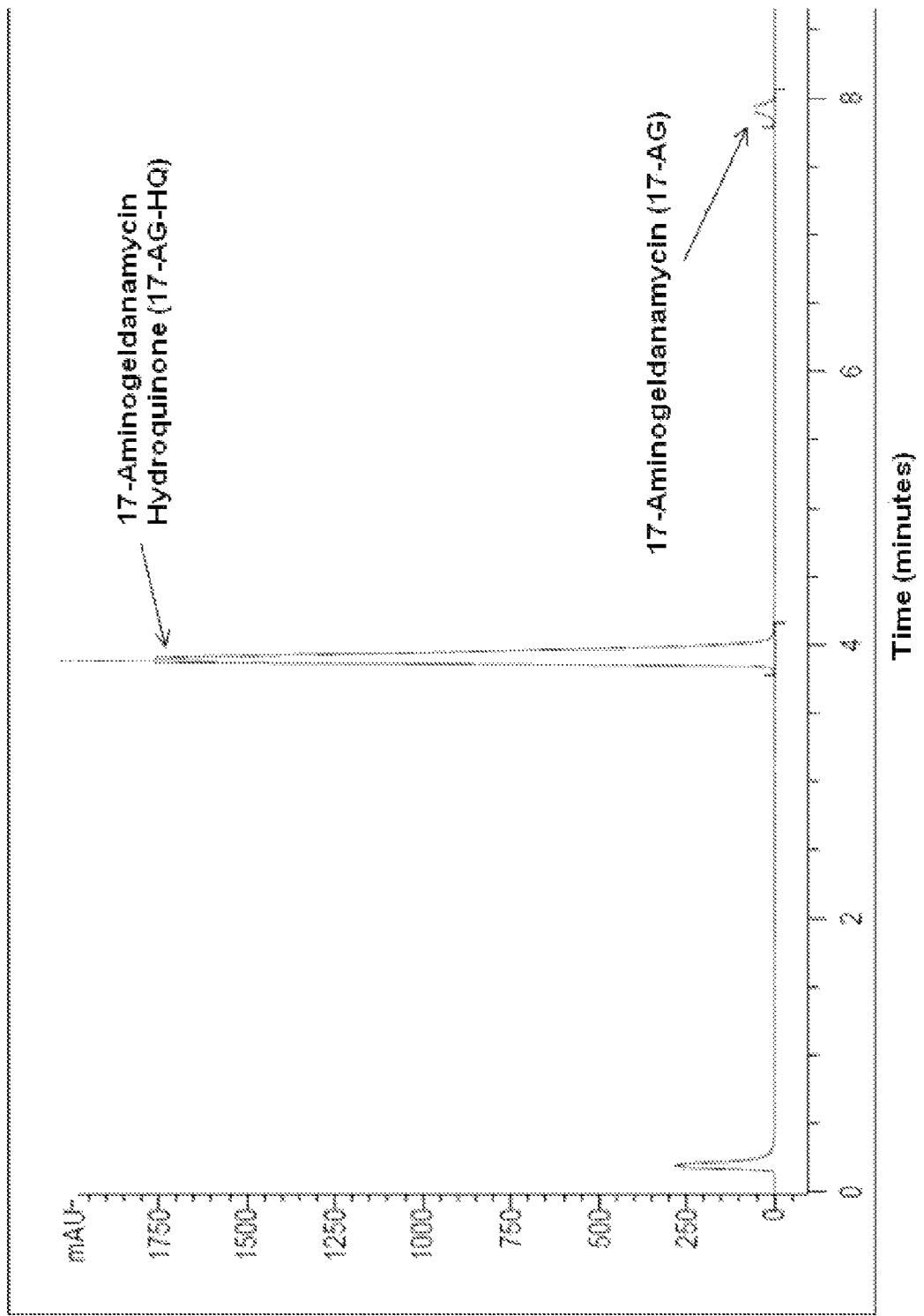
FIG. 1 depicts an HPLC chromatograpm of 17-aminogeldanamycin hydroquinone (17-AG-HQ) and the oxidation degradant, 17-amino-geldanamycin (17-AG), of Example 2 having retention times of 3.8 and 7.9, respectively.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Certain compounds of the present invention can comprise one or more asymmetric centers, and thus can exist in various isomeric forms, e.g., enantiomers and/or diastereomers. The compounds provided herein may be in the form of an individual enantiomer, diastereomer or geometric isomer, or may be in the form of a mixture of stereoisomers, including racemic mixtures and mixtures enriched in one or more stereoisomer. In certain embodiments, the compounds provided herein are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

Where a particular enantiomer is preferred, it may be provided substantially free of the corresponding enantiomer, i.e., optically enriched. "Optically-enriched," as used herein, means that the compound is made up of a greater proportion of one enantiomer compared to the other. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from mixtures by methods known to those skilled in the art, including chiral high pressure liquid chromatography (HPLC) and the formation and crystallization of chiral salts; or preferred enantiomers may be prepared by asymmetric syntheses. See, for example, Jacques, et al., *Enantiomers, Racemates and Resolutions*, Wiley Interscience, New York, 1981; Wilen, S. H., et al., *Tetrahedron* 33:2725 (1977); Eliel, E. L. *Stereochemistry of Carbon Compounds*, McGraw-Hill, NY, 1962; and Wilen, S. H. *Tables of Resolving Agents and Optical Resolutions* p. 268, E. L. Eliel, Ed., Univ. of Notre Dame Press, Notre Dame, IN 1972.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, alone or as part of another group, "alkyl" refers to a monoradical of a straight-chain or branched saturated hydrocarbon group having from 1 to 8 carbon atoms ("$C_{1-8}$ alkyl"). In some embodiments, an alkyl group can have from 1 to 6 carbon atoms ("$C_{1-6}$ alkyl"). In some embodiments, an alkyl group can have from 1 to 4 carbon atoms ("$C_{1-4}$ alkyl"). Examples of $C_{1-4}$ alkyl groups include methyl, ethyl, propyl, isopropyl, butyl, isobutyl, sec-butyl and tent-butyl. Examples of $C_{1-6}$ alkyl groups include the aforementioned $C_{1-4}$ alkyl groups as well as pentyl, isopentyl, neopentyl, hexyl and the like. Additional examples of alkyl groups include heptyl, octyl and the like. Unless otherwise specified, each instance of an alkyl group is independently unsubstituted or substituted with 1-5 groups as described herein.

As used herein, alone or as part of another group, "alkenyl" refers to a monoradical of a straight-chain or branched hydrocarbon group having from 2 to 8 carbon atoms and one or more carbon-carbon double bonds ("$C_{2-8}$ alkenyl"). In some embodiments, an alkenyl group can have from 2 to 6 carbon atoms ("$C_{2-6}$ alkenyl"). In some embodiments, an alkenyl group can have from 2 to 4 carbon atoms ("$C_{2-4}$ alkenyl"). The one or more carbon-carbon double bonds can be internal (such as in 2-butenyl) or terminal (such as in 1-butenyl). Examples of $C_{2-4}$ alkenyl groups include ethenyl, 1-propenyl, 2-propenyl, 1-butenyl, 2-butenyl, butadienyl and the like. Examples of $C_{2-6}$ alkenyl groups include the aforementioned $C_{2-4}$ alkenyl groups as well as pentenyl, pentadienyl, hexenyl and the like. Additional examples of alkenyl include heptenyl, octenyl, octatrienyl and the like. Unless otherwise specified, each instance of an alkenyl group is independently unsubstituted or substituted with 1-5 groups as described herein.

As used herein, alone or as part of another group, "alkynyl" refers to a monoradical of a straight-chain or branched hydrocarbon group having from 2 to 8 carbon atoms and one or more carbon-carbon triple bonds ("$C_{2-8}$ alkynyl"). In some embodiments, an alkynyl group can have from 2 to 6 carbon atoms ("$C_{2-6}$ alkynyl"). In some embodiments, an alkynyl group can have from 2 to 4 carbon atoms ("$C_{2-4}$ alkynyl"). The one or more carbon-carbon triple bonds can be internal (such as in 2-butynyl) or terminal (such as in 1-butynyl). Examples of $C_{2-4}$ alkynyl groups include ethynyl, 1-propynyl, 2-propynyl, 1-butynyl, 2-butynyl and the like. Examples of $C_{2-6}$ alkenyl groups include the aforementioned $C_{2-4}$ alkynyl groups as well as pentynyl, hexynyl and the like. Additional examples of alkynyl include heptynyl, octynyl and the like. Unless otherwise specified, each instance of an alkynyl group is independently unsubstituted or substituted with 1-5 groups as described herein.

As used herein, alone or as part of another group, "cycloalkyl" refers to a monocyclic, saturated carbocyclyl group having from 3 to 10 ring carbon atoms ("$C_{3-10}$ cycloalkyl"). In some embodiments, a cycloalkyl group can have from 3 to 6 ring carbon atoms ("$C_{3-6}$ cycloalkyl"). In some embodiments, a cycloalkyl group can have from 5 to 6 ring carbon atoms ("$C_{5-6}$ cycloalkyl"). Examples of $C_{5-6}$ cycloalkyl groups include cyclopentyl and cyclohexyl. Examples of $C_{3-6}$ cycloalkyl groups include the aforementioned $C_{5-6}$ cycloalkyl groups as well as cyclopropyl and cyclobutyl. Examples of $C_{3-8}$ cycloalkyl groups include the aforementioned $C_{3-6}$ cycloalkyl groups as well as cycloheptyl and cyclooctyl. Unless otherwise specified, each instance of a cycloalkyl group is independently unsubstituted or substituted with 1-5 groups as described herein.

As used herein, alone or as part of another group, "cycloalkenyl" refers to an unsaturated non-aromatic carbocyclyl group (i.e., a carbocyclyl group containing one or more double bonds) having from 3 to 10 ring carbon atoms ("$C_{3-10}$ cycloalkyl"). "Cycloalkenyl" is intended to encompass rings having multiple sites of unsaturation, but is not intended to include aryl moieties, as herein defined. In some embodiments, a cycloalkenyl group can have from 3 to 6 ring carbon atoms ("$C_{3-6}$ cycloalkenyl"). In some embodiments, a cycloalkenyl group can have from 5 to 6 ring carbon atoms ("$C_{5-6}$ cycloalkenyl"). Examples of $C_{5-6}$ cycloalkenyl groups include cyclopentenyl and cyclohexenyl. Examples of $C_{3-6}$ cycloalkenyl groups include the aforementioned $C_{5-6}$ cycloalkenyl groups as well as cyclopropenyl and cyclobutenyl. Examples of $C_{3-8}$ cycloalkenyl groups include the aforementioned $C_{3-6}$ cycloalkenyl groups as well as cycloheptenyl and cyclooctenyl. Unless otherwise specified, each instance of a cycloalkenyl group is independently unsubstituted or substituted with 1-5 groups as described herein.

As used herein, alone or as part of another group, "heterocyclyl" refers to a refers to a non-aromatic ring system having from 3 to 10 ring carbon atoms and 1 to 4 ring heteroatoms, each heteroatom independently selected from nitrogen, oxygen and sulfur. "Heterocyclyl" is intended to encompass (i) rings having multiple sites of unsaturation, but is not intended to include heteroaryl moieties, as herein defined; and (ii) fused ring systems wherein one ring is aromatic and the other is non-aromatic. In some embodiments, a heterocyclyl group can have from 3 to 7 ring atoms selected from carbon atoms and 1 to 3 heteroatoms, each heteroatom independently selected from nitrogen, oxygen and sulfur. In some embodiments, a heterocyclyl group can have from 5 to 7 ring atoms selected from carbon atoms and 1 or 2 heteroatoms, each heteroatom independently selected from nitrogen, oxygen and sulfur. In some embodiments, a heterocyclyl group can have from 5 to 6 ring atoms selected from carbon atoms and 1 to 3 heteroatoms, each heteroatom independently selected from nitrogen, oxygen and sulfur. Heterocyclyl groups can be saturated or can contain one or more carbon-carbon double bonds, carbon-nitrogen double bonds, or carbon-carbon triple bonds. In heterocyclyl groups that contain one or more nitrogen atoms, the point of attachment can be a carbon or nitrogen atom, as valency permits. Exemplary heterocyclyl groups with 1-2 ring heteroatoms include oxiranyl, aziridinyl, oxetanyl, azetidinyl, pyrrolidinyl, dihydropyrrolyl, tetrahydrofuranyl, dihydrofuranyl, tetrahydrothiophenyl, dihydrothiophenyl, pyrazolidinyl, imidazolidinyl, oxazolidinyl, isoxazolidinyl, thiazolidinyl, piperidinyl, tetrahydropyridinyl, dihydropyridinyl, piperazinyl, tetrahydropyranyl, dioxanyl, morpholinyl, azepanyl, diazepanyl, diazepinyl, oxepanyl, dioxepanyl, oxazepanyl, oxazepinyl, pyrrolidine-2,5-dione, pyrrole-2,5-dione and the like. Exemplary heterocyclyl groups with 1-3 heteroatoms include the aforementioned heterocyclyl groups as well as triazolidinyl, oxadiazolidinyl, triazinanyl and the like. Heterocyclyl groups can be monocyclic ("monocyclic heterocyclyl") as in the aforementioned examples, bicyclic ("bicyclic heterocyclyl"), or tricyclic ("tricyclic heterocyclyl"). Bicyclic heterocyclyl groups can include one or more heteroatoms in one or both rings. Examples of such bicyclic heterocyclyl groups include tetrahydroindolyl, decahydroquinolinyl, decahydroisoquinolinyl, octahydrochromenyl, octahydroisochromenyl, decahydronaphthyridinyl, decahydro-1,8-naphthyridinyl, octahydropyrrolo [3,2-b]pyrrole and the like. Unless otherwise specified, each instance of a heterocyclyl group is independently unsubstituted or substituted with 1-5 groups as described herein.

As used herein, alone or as part of another group, "aryl" refers to a radical of an aromatic monocyclic or bicyclic ring system having 6 or 10 ring carbon atoms. Examples of such aryl groups include phenyl, 1-naphthyl and 2-naphthyl. Unless otherwise specified, each instance of an aryl group is independently unsubstituted or substituted with 1-5 groups as described herein.

The term "aralkyl" refers to an alkyl group substituted by an aryl group, wherein the alkyl and aryl portions are independently unsubstituted or substituted as described herein.

As used herein, alone or as part of another group, "heteroaryl" refers to a radical of a 5- to 10-membered aromatic ring system having ring carbon atoms and 1 to 4 ring heteroatoms, each heteroatom independently selected from nitrogen, oxygen and sulfur. Examples of such heteroaryl groups include pyrrolyl, furanyl (furyl), thiophenyl (thienyl), pyrazolyl, imidazolyl, oxazolyl, isoxazolyl, thiazolyl, triazolyl, oxadiazolyl, thiadiazolyl, tetrazolyl, pyridinyl (pyridyl), pyridazinyl, pyrimdinyl, pyrazinyl, triazinyl, indolyl, benzofuranyl, benzothiophenyl (benzothienyl), indazolyl, benzimidazolyl, benzoxazolyl, benzisoxazolyl, benzothiazolyl, quinolinyl, isoquinolinyl, cinnolinyl, quinazolinyl, quinoxalinyl, phthalazinyl, naphthyridinyl and the like. In some embodiments a heteroaryl group can be monocyclic ("monocyclic heteroaryl"), and in some embodiments a heteroaryl group can be bicyclic ("bicyclic heteroaryl"). Unless otherwise specified, each instance of a heteroaryl group is independently unsubstituted or substituted with 1-5 groups as described herein.

The term "heteroaralkyl" refers to an alkyl group substituted by a heteroaryl group, wherein the alkyl and heteroaryl portions are independently unsubstituted or substituted as described herein.

As described herein, compounds may contain substituted or unsubstituted carbon atoms. In general, the term "substituted" means that one or more hydrogens of the carbon atom are replaced with a substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable compounds, i.e., compounds that are not substantially altered when subjected to conditions to allow for their production, detection, and, in certain embodiments, their recovery, purification, and/ or use for one or more of the purposes disclosed herein.

Exemplary substituents include, but are not limited to, halo, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(O)R$^{aa}$, —CO$_2$H, —CO$_2$R$^{aa}$, —OC(O)R$^{aa}$, —OCO$_2$R$^{aa}$, —C(O)N(R$^{bb}$)$_2$, —OC(O)N(R$^{bb}$)$_2$, —NR$^{bb}$C(O)R$^{aa}$, —NR$^{bb}$CO$_2$R$^{aa}$, —NR$^{bb}$C(O)N(R$^{bb}$)$_2$, —C(NR$^{bb}$)N(R)$^{bb}$$_2$, —OC(NR$^{bb}$)R$^{aa}$, —OC(NR$^{bb}$)OR$^{aa}$, —C(NR$^{bb}$)N(R$^{bb}$)$_2$, —OC(NR$^{bb}$)N(R$^{bb}$$_2$, —NR$^{bb}$C(NR$^{bb}$)N(R$^{bb}$)$_2$, —NR$^{bb}$SO$_2$R$^{aa}$, —SO$_2$N(R$^{bb}$)$_2$, —SO$_2$R$^{cc}$, —SO$_2$OR$^{cc}$, —OSO$_2$R$^{aa}$, —SOR$^{aa}$, —Si(R$^{cc}$)$_3$, —OSi(R$^{aa}$)$_3$, —C(S)N (R$^{bb}$)$_2$, —C(O)SR$^{cc}$, —C(S)SR$^{cc}$, —SC(S)SR$^{cc}$, —P(O)$_2$R$^{aa}$, —P(O)(R$^{aa}$)$_2$, —OP(O)(R$^{aa}$)$_2$, —OP(O)(OR$^{aa}$)$_2$, —OP(O)(OR$^{cc}$)$_2$, C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, 3-10 membered heteroaryl, wherein each of the C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl may be optionally substituted with 1-5 R$^{dd}$ groups;

or two geminal substituents may be joined to form =O, =S, =NN(R$^{bb}$)$_2$, =NNR$^{bb}$C(O)R$^{aa}$, =NNR$^{bb}$CO$_2$R$^{aa}$, =NNR$^{bb}$S(O)$_2$R$^{aa}$, =NR$^{bb}$, =NOR', —O(C(R$^{cc}$)$_2$)$_{2-3}$O—, or —S(C(R$^{cc}$)$_2$)$_{2-3}$S—;

or two vicinal substituents may be joined to form —O(C(R$^{cc}$)$_{1-2}$O— or —S(C(R$^{cc}$)$_2$)$_{2-3}$S—;

each instance of R$^{aa}$ is, independently, selected from C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl, wherein each of the C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl may be optionally substituted with 1-5 R$^{dd}$ groups;

each instance of R$^{bb}$ is, independently, selected from —H, —OH, —OR$^{aa}$, an amino protecting group (e.g., —C(O)R$^{aa}$, —C(O)OR$^{aa}$, —SO$_2$R$^{aa}$), C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl, wherein each of the C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl may be optionally substituted with 1-5 R$^{dd}$ groups;

each instance of R$^{cc}$ is, independently, selected from —H, C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl, wherein each of the C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl may be optionally substituted with 1-5 R$^{dd}$ groups;

each instance of R$^{dd}$ is, independently, selected from halo, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(O)R$^{ee}$, —CO$_2$H, —CO$_2$R$^{ee}$, —OC(O)R$^{ee}$, —OCO$_2$(R$^{ee}$), —C(O)N(R)$^{ff}$$_2$, —OC(O)N(R$^{ff}$)$_2$, —NR$^{ff}$C(O)R$^{ee}$, —NR$^{ff}$CO$_2$R$^{ee}$, —NR$^{ff}$C(O)N(R$^{ff}$)$_2$, —C(NR$^{ff}$)OR$^{ee}$, —OC(NR$^{ff}$)R$^{ee}$), —OC(NR$^{ff}$)OR$^{ee}$, —C(NR$^{ff}$N(R$^{ff}$)$_2$, —OC(NR$^{ff}$)N(R$^{ff}$)$_2$, —NR$^{ff}$C(NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{cc}$, —SOR$^{ee}$, —Si(R$^{cc}$), —OSi(R$^{ee}$)$_3$, —C(S)N(R$^{ff}$)$_2$, —C(O)SR$^{ee}$, —C(S)SR$^{ee}$, —SC(S)SR$^{ee}$, —P(O)$_2$R$^{ee}$, —P(O)(R$^{ee}$)$_2$, —OP(O)(R$^{ee}$)$_2$, —OP(O)(OR$^{ee}$)$_2$, C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, 3-10 membered heteroaryl, wherein each of the C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl are optionally substituted with 1-5 R$^{gg}$ groups; or two geminal R$^{dd}$ substituents may be joined to form =O or =S;

each instance of R$^{ee}$ is, independently, selected from C$_{1-6}$ alkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, and 3-10 membered heteroaryl, wherein each of the C$_{1-6}$ alkyl, C$_{2-6}$ alkenyl, C$_{2-6}$ alkynyl, C$_{3-10}$ cycloalkyl, C$_{3-10}$ cycloalkenyl, $C_{6-10}$ aryl, 3-10 membered heterocyclyl, and 3-10 membered heteroaryl are optionally substituted with 1-5 $R^{gg}$ groups;

each instance of $R^{ff}$ is, independently, selected from H, $C_{1-6}$ alkyl, $C_{2-6}$ alkenyl, $C_{2-6}$ alkynyl, $C_{3-10}$ cycloalkyl, $C_{3-10}$ cycloalkenyl, $C_{6-10}$ aryl, 3-10 membered heterocyclyl, and 3-10 membered heteroaryl, wherein each of the $C_{1-6}$ alkyl, $C_{2-6}$ alkenyl, $C_{2-6}$ alkynyl, $C_{3-10}$ cycloalkyl, $C_{3-10}$ cycloalkenyl, $C_{6-10}$ aryl, 3-10 membered heterocyclyl, and 3-10 membered heteroaryl are optionally substituted with 1-5 $R^{gg}$ groups;

each instance of $R^{gg}$ is, independently, halo, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$X, —NH(C$_{1-6}$ alkyl)$_2$X, —NH$_2$(C$_{1-6}$ alkyl)X, —NH$_3$X, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(O)(C$_{1-6}$ alkyl), —CO$_2$H, —CO$_2$(C$_{1-6}$ alkyl), —OC(O)(C$_{1-6}$ alkyl), —OCO$_2$(C$_{1-6}$ alkyl), —C(O)NH$_2$, —C(O)N(C$_{1-6}$ alkyl)$_2$, —OC(O)NH(C$_{1-6}$ alkyl), —NHC(O)(C$_{1-6}$ alkyl), —N(C$_{1-6}$ alkyl)C(O)(C$_{1-6}$ alkyl), —NHCO$_2$(C$_{1-6}$ alkyl), —NHC(O)N(C$_{1-6}$ alkyl)$_2$, —NHC(O)NH(C$_{1-6}$ alkyl), —NHC(O)NH$_2$, —C(NH)O(C$_{1-6}$ alkyl), —OC(NH)(C$_{1-6}$ alkyl), —OC(NH)OC$_{1-6}$ alkyl, —C(NH)N(NH)(C$_{1-6}$ alkyl)$_2$, —C(NH)NH(C$_{1-6}$ alkyl), —C(NH)NH$_2$, —OC(NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(NH)NH$_2$, —NHSO$_2$(C$_{1-6}$ alkyl)$_2$, —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(S)N(C$_{1-6}$ alkyl)$_2$, C(S)NH(C$_{1-6}$ alkyl), C(S)NH$_2$, —(O)S(C$_{1-6}$ alkyl), —C(S)SC$_{1-6}$ alkyl, —SC(S)SC$_{1-6}$ alkyl, —P(O)$_2$(C$_{1-6}$ alkyl), —P(O)(C$_{1-6}$ alkyl)$_2$, —OP(O)(C$_{1-6}$ alkyl)$_2$, —OP(O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ cycloalkyl, C$_{3-10}$ cycloalkenyl, C$_{6-10}$ aryl, 3-10 membered heterocyclyl, 3-10 membered heteroaryl; or two geminal $R^{gg}$ substituents may be joined to form =O or =S; and X$^-$ is a counterion.

As used herein "vicinal" refers to two substituents attached to two adjacent carbon atoms.

As used herein "geminal" refers to two substituents attached to a single carbon atom.

As used herein, "halo" and "halogen" refer to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like) and carboxylate ions (e.g., acetate, ethanoate, propanoate, benzoate, glycerate, lactate, tartrate, glycolate, and the like).

Suitable amino protecting groups include, but are not limited to, amide groups (e.g., —C(O)R$^{aa}$), carbamate groups (e.g., —C(O)OR$^{aa}$), and sulfonyl amino groups (e.g., —SO$_2$R$^{aa}$). Such amino protecting groups are well known in the art and include those described in detail in *Protecting Groups in Organic Synthesis*, T. W. Greene and P. G. M. Wuts, 3$^{rd}$ edition, John Wiley & Sons, 1999.

Exemplary amide groups suitable for use as amino protecting groups include, but are not limited to, formamide, acetamide, chloroacetamide, trichloroacetamide, trifluoroacetamide, phenylacetamide, 3-phenylpropanamide, picolinamide, 3-pyridylcarboxamide,N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Exemplary carbamate groups suitable for use as amino protecting groups include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-91,3-dithianyl]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl) ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Exemplary sulfonyl amino groups suitable for use as amino protecting groups include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other suitable amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide and 3-nitropyridinesulfenamide (Npys).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art (see, e.g., S. M. Berge et al., *J. Pharmaceutical Sciences*, 1977, 66, 1-19). Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

DETAILED DESCRIPTION

The present invention provides compositions of hydroquinones of 17-amino-substituted geldanamycin analogs and methods of preparation and use.

For example, in one aspect, the present invention provides a composition comprising a sulfur-containing compound and a hydroquinone compound of the formula (I):

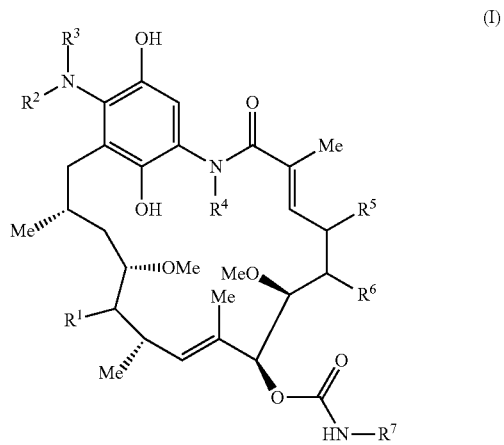

wherein:

$R^1$ is —H, —OR$^8$, —SR$^8$, —N(R$^8$)(R$^9$), —N(R$^8$)C(O)R$^9$, —N(R$^8$)C(O)OR$^9$, —N(R$^8$)C(O)N(R$^8$)(R$^9$), —OC(O)R$^8$, —OC(O)OR$^8$, —OS(O)$_2$R$^8$, —OS(O)$_2$OR$^8$, —OP(O)$_2$OR$^8$ or —CN;

each of $R^2$ and $R^3$ is, independently, selected from —H, alkyl, alkenyl, alkynyl, cycloalkyl, cycloalkenyl, heterocyclyl, aryl, aralkyl, heteroaryl, heteroaralkyl, or —C(=O)CH$_3$; or $R^2$ and $R^3$ taken together with the nitrogen to which they are bonded represent a 3- to 8-membered heterocyclyl ring which contains 1 to 3 heteroatoms selected from O, N, S, and P;

$R^4$ is —H, alkyl, alkenyl or aralkyl;

$R^5$ and $R^6$ are each —H, or $R^5$ and $R^6$ taken together form a bond;

$R^7$ is —H, alkyl, alkenyl, alkynyl, cycloalkyl, cycloalkenyl, heterocyclyl, aryl, aralkyl, heteroaryl, or heteroaralkyl; and each instance of $R^8$ and $R^9$ is, independently, selected from —H, alkyl, alkenyl, alkynyl, cycloalkyl, cycloalkenyl, heterocyclyl, aryl, aralkyl, heteroaryl, or heteroaralkyl; or $R^8$ and $R^9$ taken together represent a 3 to 8 membered optionally substituted heterocyclyl ring which contains 1 to 3 heteroatoms selected from O, N, S, and P.

In certain embodiments, $R^1$ is —$OR^8$, —$OC(O)R^8$, —$OC(O)OR^8$, —$OS(O)_2R^8$, —$OS(O)_2OR^8$, or —$OP(O)_2R^8$. In certain embodiments, $R^1$ is —$OR^8$. In certain embodiments, $R^1$ is —OH. In certain embodiments, $R^1$ is —O(C=O)CH$_3$.

In certain embodiments, each of $R^2$ and $R^3$ is, independently, selected from —H, alkyl, alkenyl, alkynyl, cycloalkyl, cycloalkenyl, heterocyclyl, aryl, aralkyl, heteroaryl, or heteroaralkyl. In certain embodiments, each of $R^2$ and $R^3$ is, independently, —H, alkyl, alkenyl or aralkyl.

In certain embodiments, $R^2$ is —H. In certain embodiments, $R^3$ is —H. In certain embodiments, both $R^2$ and $R^3$ are —H.

In certain embodiments, $R^2$ is alkyl, alkenyl or aralkyl and $R^3$ is —H.

In certain embodiments, $R^2$ is alkyl and $R^3$ is —H. In certain embodiments, $R^2$ is 'CH$_2$CH$_2$F and $R^3$ is —H.

In certain embodiments, $R^2$ is alkenyl and $R^3$ is —H. In certain embodiments, $R^2$ is —CH$_2$CH=CH$_2$ and $R^3$ is —H.

In certain embodiments, $R^2$ is aralkyl and $R^3$ is —H. In certain embodiments, $R^2$ is —CH$_2$Ph and $R^3$ is —H.

In certain embodiments, $R^4$ is —H.

In certain embodiments, $R^5$ and $R^6$ are each —H. In other embodiments, $R^5$ and $R^6$ taken together form a bond.

In certain embodiments, $R^7$ is —H or alkyl. In certain embodiments, $R^7$ is —H.

In certain embodiments, $R^8$ is —H, alkyl, alkenyl, or alkynyl. In certain embodiments, $R^8$ is —H.

In certain embodiments, $R^9$ is —H, alkyl, alkenyl, or alkynyl. In certain embodiments, $R^9$ is —H.

In certain embodiments, both $R^8$ and $R^9$ are —H.

In other embodiments, wherein $R^1$ is —N($R^8$)($R^9$), $R^8$ and $R^9$ taken together represent a 3 to 8 membered heterocyclyl ring containing 1 to 3 heteroatoms selected from O, N, S, and P. In certain embodiments, wherein $R^1$ is —N($R^8$)($R^9$), $R^8$ and $R^9$ taken together represent a 3 to 5 membered heterocyclyl ring. In certain embodiments, wherein $R^1$ is —N($R^8$)($R^9$), $R^8$ and $R^9$ taken together represent a 3 membered heterocyclyl ring (e.g., aziridinyl). In certain embodiments, wherein $R^1$ is —N($R^8$)($R^9$), $R^8$ and $R^9$ taken together represent a 4 membered heterocyclyl ring (e.g., azetidinyl). In certain embodiments, wherein $R^1$ is —N($R^8$)($R^9$), $R^8$ and $R^9$ taken together represent a 5 membered heterocyclyl ring (e.g., pyrrolidinyl).

In certain embodiments, wherein $R^5$ and $R^6$ taken together form a bond, the hydroquinone compound is of the formula (I-a):

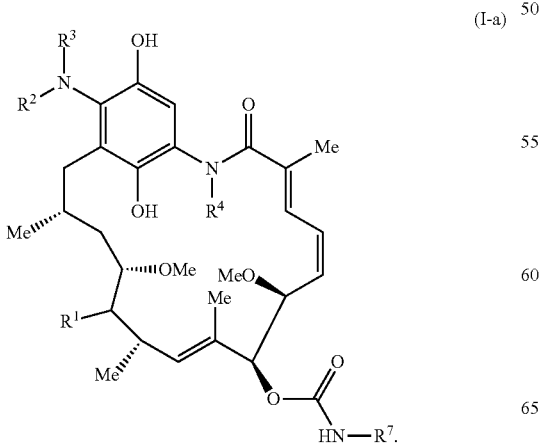

(I-a)

In certain embodiments, wherein $R^1$ is —$OR^8$ and $R^5$ and $R^6$ taken together form a bond, the hydroquinone compound is of the formula (I-b):

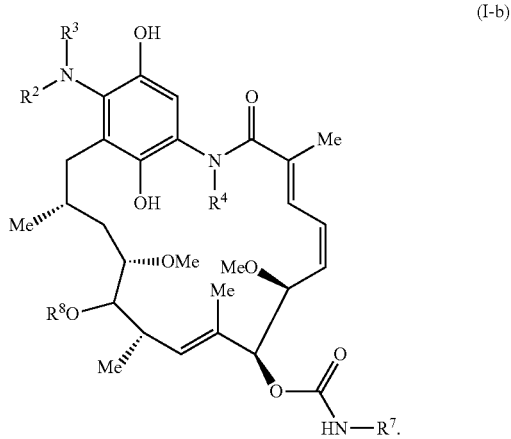

(I-b)

In certain embodiments, wherein $R^1$ is —$OR^8$, $R^4$ is —H, and $R^5$ and $R^6$ taken together form a bond, the hydroquinone compound is of the formula (I-c):

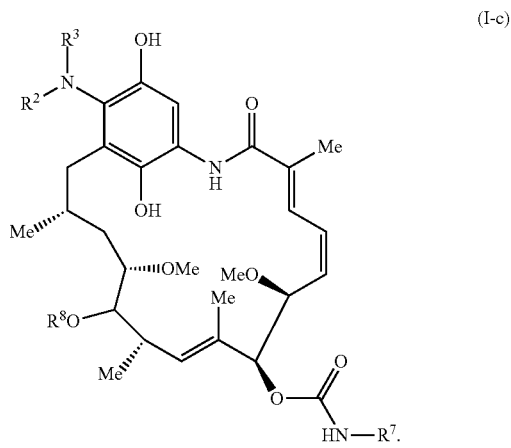

(I-c)

In certain embodiments, wherein $R^1$ is —$OR^8$, $R^4$ and $R^7$ are —H, and $R^5$ and $R^6$ taken together form a bond, the hydroquinone compound is of the formula (I-d):

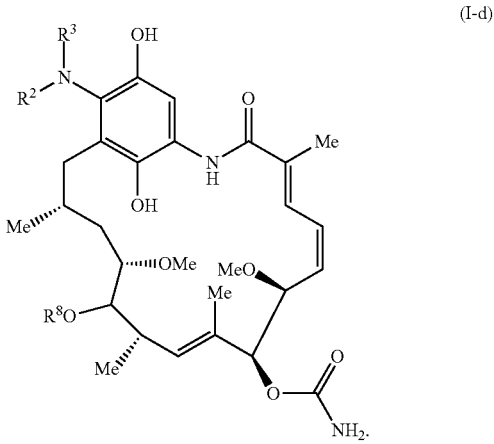

(I-d)

In certain embodiments, wherein R¹ is —OH, R⁴ and R⁷ are —H, and R⁵ and R⁶ taken together form a bond, the hydroquinone compound is of the formula (I-e):
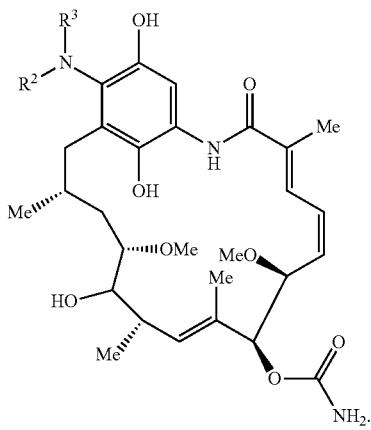
(I-e)
In certain embodiments, the hydroquinone compound of formula (I) is selected from the group consisting of:
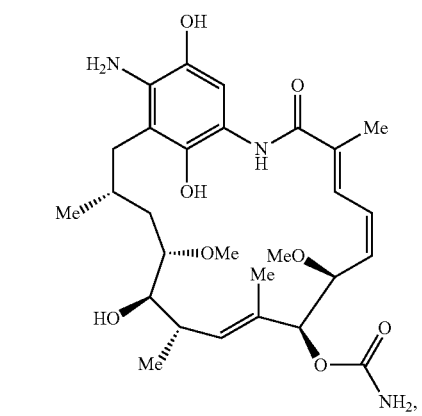
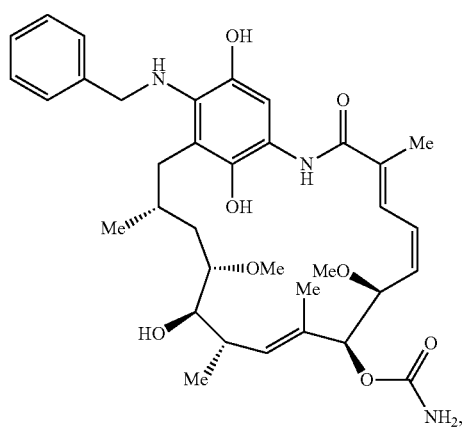
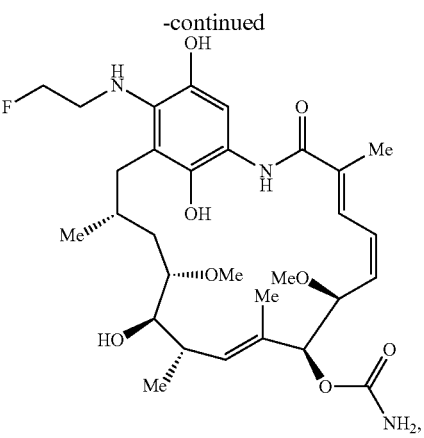
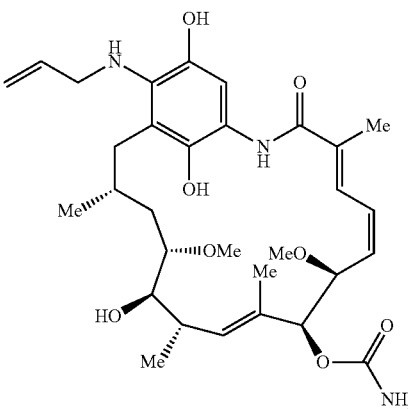
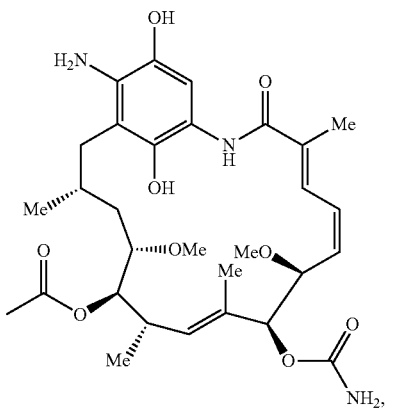
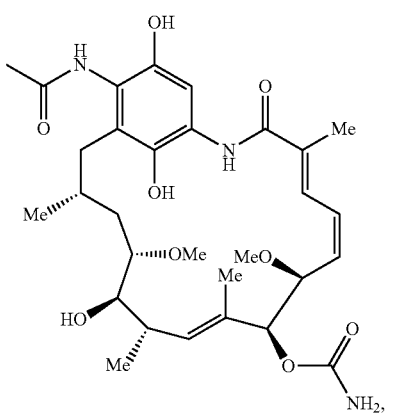

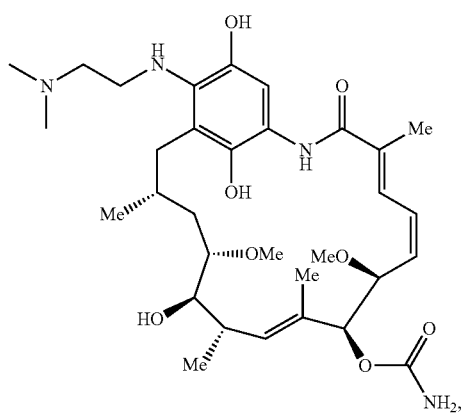
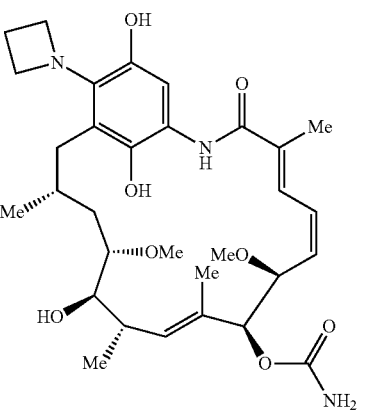
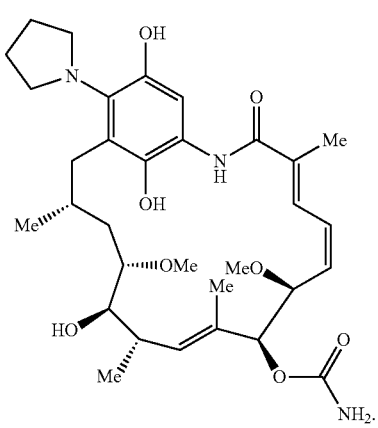
In certain embodiments, the compound of formula (I) is 17-amino-geldanamycin hydroquinone (17-AG-HQ):
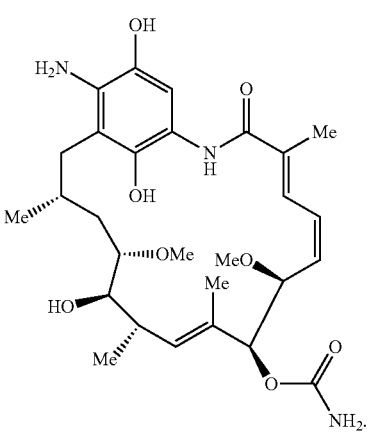
17-AG-HQ
In certain embodiments, the compound of formula (I) is 17-benzylamino-geldanamycin hydroquinone (17-BAG-HQ):

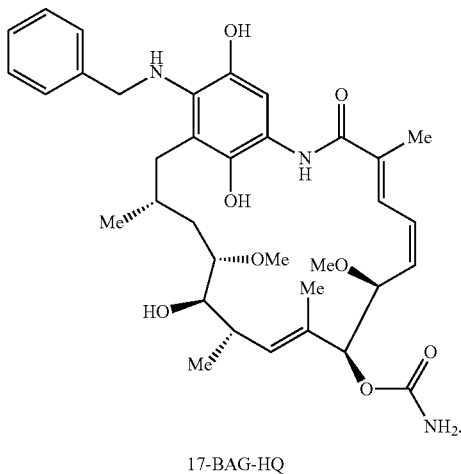 [SMILES: CO[C@H]1/C=C\C=C(/C)C(=O)Nc2cc(O)c(NCc3ccccc3)c(c2O)C[C@@H](C)C[C@H](OC)[C@H](O)[C@@H](C)/C=C(\C)[C@@H]1OC(N)=O]

17-BAG-HQ

In certain embodiments, the compound of formula (I) is 17-(2-fluoroethylamino)-geldanamycin hydroquinone (17-FEAG-HQ):

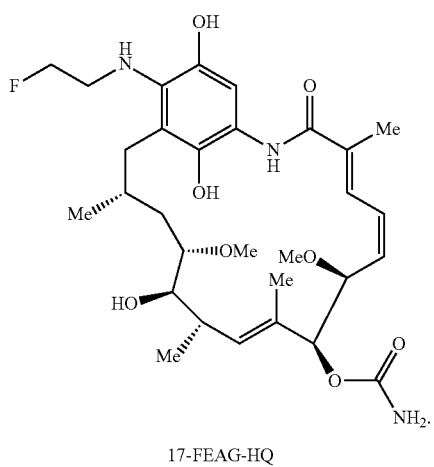 [SMILES: CO[C@H]1/C=C\C=C(/C)C(=O)Nc2cc(O)c(NCCF)c(c2O)C[C@@H](C)C[C@H](OC)[C@H](O)[C@@H](C)/C=C(\C)[C@@H]1OC(N)=O]

17-FEAG-HQ

In certain embodiments, the compound of formula (I) is 17-allylamino-geldanamycin hydroquinone (17-AAG-HQ):

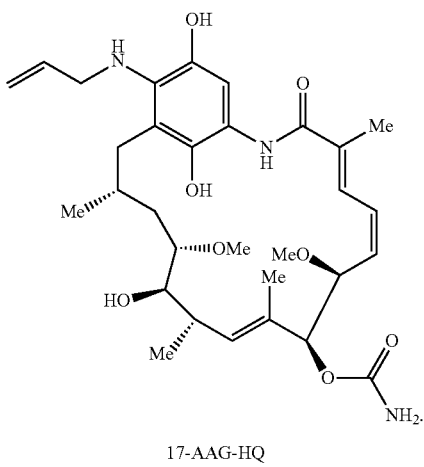 [SMILES: C=CCNc1c(O)cc2c(O)c1C[C@@H](C)C[C@H](OC)[C@H](O)[C@@H](C)/C=C(\C)[C@H](OC(N)=O)[C@@H](OC)/C=C\C=C(/C)C(=O)N2]

17-AAG-HQ

In certain embodiments, the composition is a stable composition.

As used herein, a "stable composition" refers a composition comprising a sulfur-containing compound and a baseline amount of the compound of formula (I) (e.g., such as percent purity as measured by HPLC) such that, after being subjected to standard stability conditions (e.g., 40° C. and 75% relative humidity) for a specified period of time (e.g., 1 day, 2 days, 3 days, 4 days, 5 days, 7 days, 14 days, 21 days, or 30 days), at least about 80% of the original amount of the compound of formula (I) remains in the composition (i.e., has not oxidized to a compound of formula (II) or degraded to other by-products). In certain embodiments, at least about 85%, at least about 90%, at least about 91%, at least about 92%, at least about 93%, at least about 94%, or at least about 95% of the original amount of the hydroquinone compound of formula (I) remains in the composition for a specified period of time (e.g., 1 day, 2 days, 3 days, 4 days, 5 days, 7 days, 14 days, 21 days, or 30 days).

In certain embodiments, the composition is stable at 40° C. and 75% relative humidity for at least 1 day. In certain embodiments, the composition is stable at 40° C. and 75% relative humidity for at least 2 days, 3 days, 4 days, 5 days, 7 days, 14 days, 21 days, or 30 days.

As generally defined above, the inventive compositions comprise a compound of formula (I) and a sulfur-containing compound. Exemplary sulfur-containing compounds include, but are not limited to, sulfites, sulfates, sulfones and the like. In certain embodiments, the sulfur-containing compound is not a sulfonate (i.e., a sulfonic acid salt). In certain embodiments, the sulfur-containing compound is a sulfite.

Exemplary sulfites include, but are not limited to, potassium bisulfate ($KHSO_3$), sodium bisulfate ($NaHSO_3$), calcium bisulfate ($Ca(HSO_3)_2$), magnesium bisulfate ($Mg(HSO_3)_2$), potassium metabisulfite ($K_2S_2O_5$), sodium metabisulfite ($Na_2S_2O_5$), calcium metabisulfite ($CaS_2O_5$), magnesium metabisulfite ($MgS_2O_5$), potassium sulfite ($K_2SO_3$), sodium sulfite ($Na_2SO_3$), calcium sulfite ($CaSO_3$), magnesium sulfite ($MgSO_3$), potassium hydrosulfite ($K_2S_2O_4$), sodium hydrosulfite ($Na_2S_2O_4$), calcium hydrosulfite ($CaS_2O_4$), magnesium hydrosulfite ($MgS_2O_4$), and sodium formaldehyde sulfoxylate ("SFS"; $HOCH_2S(=O)ONa$).

In certain embodiments, the sulfite is potassium bisulfite, sodium bisulfite, potassium metabisulfite, sodium metabisulfite, potassium sulfite, sodium sulfite, potassium hydrosulfite, or sodium hydrosulfite. In certain embodiments, the sulfite is sodium bisulfite, sodium metabisulfite, sodium sulfite, or sodium hydrosulfite. In certain embodiments, the sulfite is sodium hydrosulfite.

In certain embodiments, the sulfite is a compound of the formula (III):

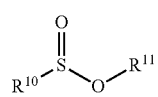

(III)

wherein:
$R^{10}$ is selected from $—OR^{12}$, $—CH_2OR^{12}$, $—S(=O)OR^{12}$ and $—S(=O)_2OR^{12}$;
$R^{11}$ and $R^{12}$ are independently selected from $—H$ and $—M$; and
M is a cation selected from sodium, potassium, magnesium or calcium.

In certain embodiments, $R^{10}$ is selected from —OH, —OM, —CH$_2$OH, —CH$_2$OM, —S(=O)OH, S(=O)OM, —S(=O)$_2$OH and —S(=O)$_2$OM.

In certain embodiments, $R^{11}$ is —M.

In certain embodiments, M is sodium or potassium. In certain embodiments, M is sodium.

In certain embodiments, the sulfur content is a measure of the sulfur-containing compound present in the composition.

In certain embodiments, the sulfur content of the composition is greater than 0.05 percent as measured by Elemental Analysis.

In certain embodiments the sulfur content of the composition is greater than 0.05 percent, greater than 0.06 percent, greater than 0.07 percent, greater than 0.08 percent, greater than 0.09 percent, greater than 0.1 percent, greater than 0.2 percent, greater than 0.3 percent, greater than 0.4 percent, greater than 0.5 percent, greater than 0.6 percent, greater than 0.7 percent, greater than 0.8 percent, greater than 0.9 percent, greater than 1 percent, greater than 2 percent, greater than 3 percent, greater than 4 percent, greater than 5 percent, greater than 6 percent, greater than 7 percent, greater than 8 percent, greater than 9 percent, or greater than 10 percent, as measured by Elemental Analysis.

In certain embodiments the sulfur content of the composition is at least about 0.06 percent, at least about 0.07 percent, at least about 0.08 percent, at least about 0.09 percent, at least about 0.1 percent, at least about 0.2 percent, at least about 0.3 percent, at least about 0.4 percent, at least about 0.5 percent, at least about 0.6 percent, at least about 0.7 percent, at least about 0.8 percent, at least about 0.9 percent, at least about 1 percent, at least about 2 percent, at least about 3 percent, at least about 4 percent, at least about 5 percent, at least about 6 percent, at least about 7 percent, at least about 8 percent, at least about 9 percent, or at least about 10 percent, as measured by Elemental Analysis.

In certain embodiments, the sulfur content of the composition is between about 0.1 percent and about 10 percent, between about 0.2 percent and about 10 percent, between about 0.3 percent and about 10 percent, between about 0.4 percent and about 10 percent, between about 0.1 percent and about 9 percent, between about 0.1 percent and about 8 percent, between about 0.1 percent and about 7 percent, or between about 0.1 percent and about 6 percent, as measured by Elemental Analysis.

In certain embodiments, the sulfur-containing compound is at least about 1% (w/w), is at least about 2% (w/w), at least about 5% (w/w), at least about 10% (w/w), at least about 20% (w/w), at least about 30% (w/w), at least about 40% (w/w), at least about 50% (w/w), at least about 60% (w/w), at least about 70% (w/w), at least about 80% (w/w), at least about 90% (w/w), at least about 95% (w/w), at least about 98% (w/w), or at least about 99% (w/w) of the composition.

In certain embodiments, the sulfur-containing compound is between about 5% (w/w) and about 99% (w/w), between about 5% (w/w) and about 90% (w/w), between about 5% (w/w) and about 80% (w/w), between about 5% (w/w) and about 70% (w/w), between about 5% (w/w) and about 60% (w/w), between about 5% (w/w) and about 50% (w/w), between about 5% (w/w) and about 40% (w/w), between about 5% (w/w) and about 30% (w/w), between about 5% (w/w) and about 20% (w/w), or between about 5% (w/w) and about 10% (w/w) of the composition.

In certain embodiments, the sulfur-containing compound is between about 10% (w/w) and about 90% (w/w), between about 20% (w/w) and about 90% (w/w), between about 30% (w/w) and about 90% (w/w), between about 40% (w/w) and about 90% (w/w), between about 50% (w/w) and about 90% (w/w), between about 60% (w/w) and about 90% (w/w), between about 70% (w/w) and about 90% (w/w), or between about 80% (w/w) and about 90% (w/w) of the composition.

In certain embodiments, the molar ratio of the compound of formula (I) to sulfur-containing compound is about 0.001:1, about 0.01:1, about 0.1:1, about 1:1, about 5:1; about 10:1, about 20:1, about 30:1, about 40:1, about 50:1; about 60:1; about 70:1; about 80:1; about 90:1; about 100:1, or about 1000:1.

In certain embodiments, the molar ratio of sulfur-containing compound to the compound of formula (I) is about 0.001:1, about 0.01:1, about 0.1:1, about 1:1, about 5:1; about 10:1, about 20:1, about 30:1, about 40:1, about 50:1; about 60:1; about 70:1; about 80:1; about 90:1; about 100:1, or about 1000:1.

The applicants have found that increasing the sulfur content in composition, e.g., by increasing the amount of sulfur-containing compound in the composition, increases the stability of the compound of formula (I). Without wishing to be bound to any particular theory, it is hypothesized that this increase in stability is due to an increase in non-covalent (non-ionic) associations between the hydroquinone moiety of the compound of formula (I) and the sulfur-containing compound, e.g., for example, hydrogen bonding associations.

For example, in certain embodiments, wherein the sulfur containing compound is a sulfite, the increase in stability of the composition may be due formation of one or more hydrogen-bonded complexes of the formula (IV):

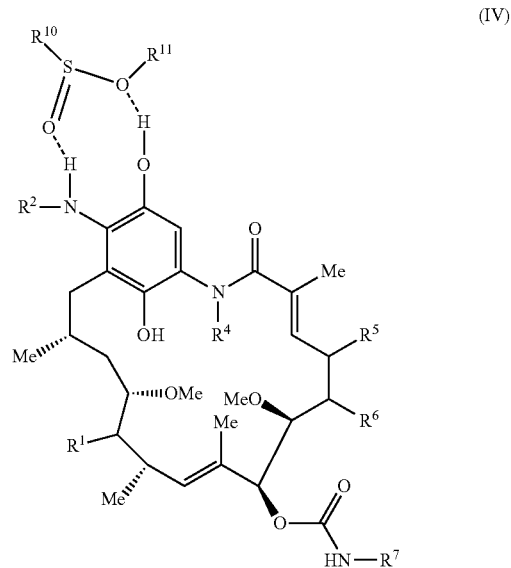

(IV)

wherein:
$R^{10}$ is selected from —OR$^{12}$, —CH$_2$OR$^{12}$, —S(=O)OR$^{12}$ and —S(=O)$_2$OR$^{12}$;
$R^{11}$ and $R^{12}$ are independently selected from —H and —M; and
M is a cation selected from sodium, potassium, magnesium or calcium.

Formulations

In certain embodiments, the present invention provides pharmaceutical formulations comprising a composition, as described above, and a pharmaceutically acceptable excipient.

Pharmaceutically acceptable excipients include any and all solvents, diluents, or other liquid vehicle, surface active agents, isotonic agents, thickening or emulsifying agents, sugars, polymers, surfactants, antioxidants, solubilizing or suspending agents, chelating agents, preservatives, dilutents, granulating and/or dispersing agents, binding agents, and/or lubricating agents, or combinations thereof, as suited to the particular dosage form desired and according to the judgment of the formulator. Remington's Pharmaceutical Sciences, Sixteenth Edition, E. W. Martin (Mack Publishing Co., Easton, Pa., 1980) discloses various carriers used in preparing pharmaceutically acceptable formulations and known techniques for the preparation thereof. Except insofar as any conventional carrier medium is incompatible with the inventive compositions, such as by producing any undesirable biological effect or otherwise interacting in a deleterious manner with any component of the composition, its use is contemplated to be within the scope of this invention.

In certain embodiments, at least one excipient provided in the formulation is a sugar. The term "sugar" as used herein refers to a natural or an unnatural monosaccharide, disaccharide, oligosaccharide, or polysaccharide, comprising one or more triose, tetrose, pentose, hexose, heptose, octose, or nonose saccharides. Sugars may include substances derived from saccharides by reduction of the carbonyl group (alditols), by oxidation of one or more terminal groups to carboxylic acids (aldonic acids), or by replacement of one or more hydroxyl group(s) by a hydrogen (deoxy sugars), an amino group (amino sugars), a thiol group (thio sugars), an acylamino group, a sulfate group, a phosphate group, or similar heteroatomic group; or any combination of the foregoing modifications. The term sugar also includes derivatives of these compounds (i.e., sugars that have been chemically modified by acylation, alkylation, and formation of glycosidic bonds by reaction of sugar alcohols with aldehydes or ketones, etc.). Sugars may be present in cyclic form (i.e., oxiroses, oxetosesm furanoses, pyranoses, septanoses, octanoses, etc.) as hemiacetals, hemiketals, or lactones, or in acyclic form. The saccharides may be ketoses, aldoses, polyols and/or a mixture of ketoses, aldoses and polyols.

Exemplary sugars include, but are not limited to, glycerol, polyvinylalcohol, propylene glycol, sorbitol, ribose, arabinose, xylose, lyxose, allose, altrose, mannose, mannitol, gulose, dextrose, idose, galactose, talose, glucose, fructose, dextrates, lactose, sucrose, starches (i.e., amylase and amylopectin), sodium starch glycolate, cellulose and cellulose derivatives (i.e., methylcellulose, hydroxypropyl cellulose, hydroxyethyl cellulose, hydroxyethylmethyl cellulose, carboxymethyl cellulose, cellulose acetate, cellulose acetate phthalate, croscarmellose, hypomellose, and hydroxypropyl methyl cellulose), carrageenan, cyclodextrins (e.g., hydroxypropyl-gamma-CD), dextrin, polydextrose, and trehalose. In certain embodiments, the sugar is selected from anhydrous lactose, lactose monohydrate, trehalose and hydroxypropyl-gamma-CD.

In certain embodiments, at least one excipient provided in the formulation is a polymer. Exemplary polymers include, but are not limited to, polyvinyl alcohol (PVA), gelatin, polyvinyl pyrolidone (PVP), albumin, polyethyleneimine (PEI), acacia gum, cellulose derivatives, calcium polypectate, maleic anhydride derivatives, polyacrylic and methacrylic acid, phospholipids, glycols (such as propylene glycol or polyethylene glycol), polyglcolide and lactide derivatives, polyethylene-polyoxypropylene-block polymers, starch, waxes, oils, alginates and alginic acid, calcium caseinate, carrageenan, pectins, polyhexametaphosphate, polyvinyl acetate, polyvinyl alcohol, and the like; mixtures thereof; and the like. In certain embodiments, the polymer is polyvinyl alcohol (PVA).

In certain embodiments, at least one excipient provided in the formulation is a surfactant. Exemplary surfactants include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the surfactant is a Tween surfactant (e.g., Tween 60, Tween 80, etc.).

In certain embodiments, at least one excipient provided in the formulation is an antioxidant. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, cysteine hydrochloride, thioglycerol, sodium mercaptoacetate, sodium formaldehyde sulfoxylate (SFS), lecithin and organic phosphites (e.g., dimethyl phosphite, diethyl phosphite, dibutyl phosphite, triethyl phosphite, tris(2-chloroethyl) phosphite, tris(2-4-t-butyl-phenyl)-phosphite, etc.). In certain embodiments, the antioxidant is dibutyl phosphite. In certain embodiments, the antioxidant is sodium bisulfite ($NaHSO_3$).

In certain embodiments, at least one excipient provided in the formulation is a solubilizing or suspending agent. Exemplary solubilizing or suspending agents include, but are not limited to, water, organic solvents and oils, or mixtures thereof.

Exemplary organic solvents include, but are not limited to, ethanol, propanol, butanol, chloroform, dichloromethane, ethyl acetate, diethyl ether, hexames, acetone, benzene, toluene, and xylenes.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In certain embodiments, at least one excipient provided in the formulation is a chelating agent. Exemplary chelating agents include, but are not limited to, ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

In certain embodiments, at least one excipient provided in the formulation is a preservative.

Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include, but are not limited to, ethanol, polyethylene glycol, phenol, phenolic compounds, bisphenol, chlorobutanol, hydroxybenzoate, and phenylethyl alcohol.

Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

In certain embodiments, at least one excipient provided in the formulation is a diluent. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In certain embodiments, at least one excipient provided in the formulation is a granulating and/or dispersing agent. Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

In certain embodiments, at least one excipient provided in the formulation is a binding agent. Exemplary binding agents include, but are not limited to, starch (e.g., cornstarch and starch paste); gelatin; sugars (e.g., sucrose, glucose, dextrose, dextrin, molasses, lactose, lactitol, mannitol, etc.); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In certain embodiments, at least one excipient provided in the formulation is a buffering agent. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

In certain embodiments, at least one excipient provided in the formulation is a lubricating agent. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

In some embodiments, the one or more pharmaceutically acceptable excipients added to the formulation are at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

The formulations described herein may be prepared by any method known or hereafter developed in the art of pharmacology. In general, such preparatory methods include the step of bringing the inventive composition into association with one or more excipients as described above and herein, and then, if necessary and/or desirable, shaping and/or packaging the product into a desired single- or multi-dose unit.

A formulation of the present invention may be prepared, packaged, and/or sold in bulk, as a single unit dose, and/or as a plurality of single unit doses. As used herein, a "unit dose"

is discrete amount of the formulation comprising a predetermined amount of the inventive composition.

The relative amounts of the inventive composition and excipients in the formulation will vary, depending upon the identity, size, and/or condition of the subject treated and further depending upon the route by which the formulation is to be administered. By way of example, the composition may comprise between 0.1% and 100% (w/w) of the formulation.

Liquid dosage forms for oral and parenteral administration include, but are not limited to, pharmaceutically acceptable emulsions, microemulsions, solutions, suspensions, syrups and elixirs. In addition to the inventive composition, the liquid dosage form may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral formulations can include adjuvants such as wetting agents, emulsifying and suspending agents, sweetening, flavoring, and perfuming agents. In certain embodiments for parenteral administration, the inventive compositions are mixed with solubilizing agents such as Cremophor, alcohols, oils, modified oils, glycols, polysorbates, cyclodextrins, polymers, and combinations thereof.

Injectable formulations, for example, sterile injectable aqueous or oleaginous suspensions may be prepared according to the known art using suitable dispersing or wetting agents and suspending agents. The sterile injectable formulation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Formulations for rectal or vaginal administration are typically suppositories which can be prepared by mixing the inventive compositions with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage formulations for oral administration include capsules, tablets, pills, powders, and granules. In such solid dosage forms, the inventive composition is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid dosage formulations of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the inventive composition only, or preferentially, in a certain part of the intestinal tract, optionally, in a delayed manner. Examples of embedding inventive compositions which can be used include polymeric substances and waxes. Solid dosage formulations of a similar type may be employed as fillers in soft and hard-filled gelatin capsules using such excipients as lactose or milk sugar as well as high molecular weight polethylene glycols and the like.

Compositions and formulations according to the invention can be provided in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the inventive composition may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Formulations for topical and/or transdermal administration of an inventive composition includes ointments, pastes, creams, lotions, gels, powders, solutions, sprays, inhalants and/or patches. Generally, the inventive composition is admixed under sterile conditions with a pharmaceutically acceptable carrier and/or any needed preservatives and/or buffers as may be required. The present invention also contemplates the use of transdermal patches, which often have the added advantage of providing controlled delivery of an active ingredient to the body. Such dosage forms may be prepared, for example, by dissolving and/or dispensing the inventive composition in the proper medium. Alternatively or additionally, the rate may be controlled by either providing a rate controlling membrane and/or by dispersing the inventive composition in a polymer matrix and/or gel.

Suitable devices for use in delivering intradermal formulations include short needle devices such as those described in U.S. Pat. Nos. 4,886,499; 5,190,521; 5,328,483; 5,527,288; 4,270,537; 5,015,235; 5,141,496; and 5,417,662. Intradermal formulations may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, comprise from about 1% to about 10% (w/w) of the inventive composition. Formulations for topical administration may further comprise one or more of the additional ingredients described above and herein.

A pharmaceutical formulation may be prepared, packaged, and/or sold for pulmonary administration via the buccal cavity. Such a formulation may comprise dry particles which comprise the inventive composition and which have a diameter in the range from about 0.5 to about 7 nanometers or from about 1 to about 6 nanometers. Such formulations are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the inventive composition. The propellant may further comprise additional ingredients such as a liquid non-ionic and/or solid anionic surfactant and/or a solid diluent (which may have a particle size of the same order as particles comprising the active ingredient).

Pharmaceutical formulations for pulmonary delivery may provide the inventive composition in the form of droplets of a solution and/or suspension. Such formulations may be prepared, packaged, and/or sold as aqueous and/or dilute alcoholic solutions and/or suspensions, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are also useful for intranasal delivery. Another formulation suitable for intranasal administration is a coarse powder comprising inventive composition and having an average particle from about 0.2 to 500 micrometers. Such a formulation is administered in the manner in which snuff is taken, i.e., by rapid inhalation through the nasal passage from a container of the powder held close to the nares. Formulations suitable for nasal administration may, for example, comprise from about as little as 0.1% (w/w) and as much as 100% (w/w) of the inventive composition, and may comprise one or more of the additional ingredients as described above and herein.

General considerations in the manufacture of pharmaceutical formulations may be found, for example, in *Remington: The Science and Practice of Pharmacy* 21$^{st}$ ed., Lippincott Williams & Wilkins, 2005.

Although the descriptions of pharmaceutical formulations provided herein are principally suitable for administration to humans, it will be understood by the skilled artisan that such formulations are generally suitable for administration to animals of all sorts (e.g., primates, cattle, pigs, horses, sheep, cats, dogs, and birds). Modification of pharmaceutical formulations suitable for administration to humans in order to render the formulations suitable for administration to various animals is well understood, and the ordinarily skilled veterinary pharmacologist can design and/or perform such modification with merely ordinary, if any, experimentation.

Methods of Treatment

The present invention also provides a method of treating a hyperproliferative disorder comprising administering to a subject in need thereof a therapeutically effective amount of a composition or formulation of the present invention, as described above and herein.

The term "subject", as used herein, refers to a mammal, such as primates, cattle, pigs, horses, sheep, cats, dogs, birds (including commercially relevant birds such as chickens, ducks, geese, and/or turkeys) and humans (e.g., male, female, infant, child, adolescant, adult).

The terms "treat" or "treating," as used herein, refers to partially or completely alleviating, inhibiting, ameliorating and/or relieving a condition from which the subject is suffering or is suspected to suffer. Treating may be via prophylactic or therapeutic administration.

The term "therapeutically effective amount," as used herein, refers to the minimal amount of a compound of formula (I) provided in the composition such that, when administered, it is sufficient to treat the subject.

Hydroquinone ansamycins (e.g., such as a compound of formula (I)) are known to oxidize in vitro and in vivo at physiological pH to the corresponding benzoquinone. Ansamycins, which includes the benzoquinone 17-AAG, are known Hsp90 inhibitors. Moreover, the hydroquinones of ansamycins are also known to have Hsp90 inhibitory activity.

Hsp90 inhibitors, such as 17-AAG, have been shown to have activity against a number of cell lines and human cancer models, including, but not limited to, CML (Gone et al., *Blood* (2002) 100:3041-44), CLL (Castro et al., *Blood* (2005) 106: 2506-2512), gastric cancer and small cell lung cancer (Shen et al., *Bioorg. Med. Chem.* (2005) 13: 4960-71), non-small cell lung cancer (Nguyen et al., *Ann. Thorac. Surg.* (2000) 70: 1853-1860; Shimamura et al., *Cancer Research* (2005) 65:6401-640), thyroid cancer (Marsee et al., *J. Biol. Chem.* (2004) 279:43990-7), leukemia (Yang et al., *Onco-* gene (2006) 1-11; Nimmanapalli et al., *Cancer Res*. (2001) 61: 1799-1804), c-Kit-related diseases, such as mastocytosis, gastrointestinal stromal tumors (GISTs), mast cell leukemia, acute myelogenous leukemia and testicular cancer (Fumo et al., *Blood* (2004) 103: 1078-84), breast cancer (de Candia et al. *PNAS* (2003) 100:12337-12342; Münster et al., *Cancer Res*. (2001) 61: 2945-2952), prostate cancer (Georgakis et al. *Clin. Cancer Res*. (2006) 12:584-90; Solit et al., *Clin. Cancer Res*. (2002) 8:986-993; Neckers, *Trends Mol Med.* 2002;8(4 suppl):S55-S61), melanoma (Grbovic et al., *PNAS* (2006) 103:57-62; Burger et al., *Anti-Cancer Drugs* (2004) 15: 377-388), colon cancer (Chung et al., *J. Natl. Cancer Inst*. (2003) 95: 1624-1633), and ovarian cancer (Banerji et al., *Clin Cancer Res.* 2005;11:7023-7032).

The compositions and formulations of the present invention can be used to treat hyperproliferative disorders including, for example, gastrointestinal stromal tumor (GIST), colon cancer, colorectal cancer, pancreatic cancer, breast cancer, ovarian cancer, prostate cancer, small-cell lung cancer, non-small cell lung cancer, melanoma, multiple myeloma, myelodysplastic syndrome, leukemia, acute lymphocytic leukemia, acute myelocytic leukemia, chronic myelocytic leukemia, chronic lymphocytic leukemia, polycythemia Vera, Hodgkin lymphoma, non-Hodgkin lymphoma, Waldenstrom's macroglobulinemia, heavy chain disease, soft-tissue sarcomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, endometrial cancer, follicular lymphoma, diffuse large B-cell lymphoma, mantle cell lymphoma, hepatocellular carcinoma, thyroid cancer, gastric cancer, esophageal cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, thyroid cancer, neuroendocrine cancers and carcinoid tumors.

Actual dosage levels of the compound of formula (I) present in the composition may be varied so as to obtain an amount of the compound which is effective to achieve the desired therapeutic response for a particular subject, composition, and mode of administration, without being toxic to the subject. The selected dosage level will depend depend upon a variety of clinical factors including the route of administration; the time of administration; the rate of excretion or metabolism of the compound; the rate and extent of absorption; the duration of the treatment; other drugs, compounds and/or materials used in combination with the compound employed; the age, sex, weight, condition, general health and prior medical history of the subject being treated; and like factors well known in the medical arts.

The administered dose can be at least about 0.01 mg, at least about 0.05 mg, at least about 0.1 mg, at least about 0.5 mg, at least about 1 mg, at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 125 mg, at least about 150 mg, at least about 175 mg or at least about 200 mg of the compound of formula (I).

The dose can be administered daily, every other day, three times a week, twice a week, weekly, or bi-weekly. The dosing schedule can include a "drug holiday," (e.g., the drug can be administered for two weeks on, one week off), or continuously, without a drug holiday.

The dose can be administered in any pharmaceutically acceptable manner, e.g., orally, intravenously, intraarterially, intramuscularly, subcutaneously, intradermally, intrathecally, or intracerebrally. In certain embodiments, the dose is administered orally.

In certain embodiments, the compositions described herein can be used in combination with another therapy (e.g., another therapeutic agent or radiation) in order to achieve selective activity in the treatment of cancer. Exemplary therapeutic agents include, but are not limited to, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, doxorubicin, vindesine, leurosine, paclitaxel, taxol, taxotere, docetaxel, cis-platin, imatinib mesylate, gemcitebine, estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins. Particularly useful agents include taxotere, Gleevec (imatinib), Tarceva (erlotinib), Sutent (sunitinib), Tykerb (lapatinib) and Xeloda (capecitabine).

The composition of the present invention and the therapeutic agent do not have to be administered in the same formulation, and may, because of different physical and chemical characteristics, be administered by different routes. The mode of administration and the advisability of administration, where possible, in the same formulation, are well within the knowledge of the skilled clinician. The initial administration can be made according to established protocols known in the art, and then, based upon the observed effects, the dosage, modes of administration and times of administration can be modified by the skilled clinician.

The particular choice of therapy will depend upon the diagnosis of the attending physicians and their judgment of the condition of the patient and the appropriate treatment protocol.

The composition of the present invention and the therapy may be administered concurrently (e.g., simultaneously, essentially simultaneously or within the same treatment protocol) or sequentially, depending upon the nature of the hyperproliferative disorder, the condition of the subject, and the actual choice of therapeutic agent to be administered in conjunction (i.e., within a single treatment protocol) with the composition of the present invention.

If the composition of the present invention and the therapy are not administered simultaneously or essentially simultaneously, then the optimum order of administration may be different for different tumors. Thus, in certain situations the composition of the present invention may be administered first, followed by the administration of the therapy; and in other situations the therapy may be administered first, followed by the administration of the composition of the present invention. This alternate administration may be repeated during a single treatment protocol. The determination of the order of administration, and the number of repetitions of administration of each therapy during a treatment protocol, is well within the knowledge of the skilled physician after evaluation of the disease being treated and the condition of the patient.

When the composition of the present invention is administered in combination with another therapy, the dose of each will, in most instances, be lower than the corresponding dose for single-agent therapy.

Methods of Preparation

Also provided are methods for preparing a hydroquinone composition of the present invention, comprising the steps of:

(i) reducing a compound of formula (II):

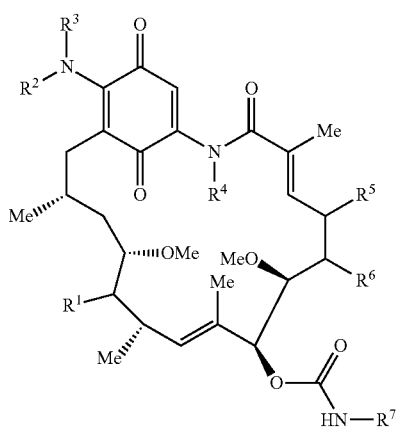

or a pharmaceutically acceptable salt thereof, to a compound of formula (I):

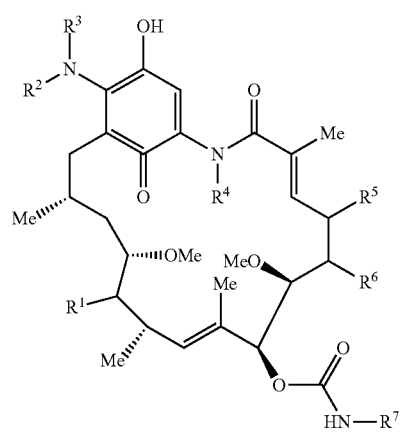

in the presence of a sulfur-containing compound; and (ii) isolating a precipitate, wherein the precipitate is a composition comprising a sulfur-containing compound and a compound of formula (I), wherein:

$R^1$ is —H, —$OR^8$, —$SR^8$ —$N(R^8)(R^9)$, —$N(R^8)C(O)R^9$, —$N(R^8)C(O)OR^9$, —$N(R^8)C(O)N(R^8)(R^9)$, —$C(O)R^8$, —$OC(O)OR^8$, —$OS(O)_2R^8$, —$OS(O)_2OR^8$, —$OP(O)_2OR^8$ or —CN;

each of $R^2$ and $R^3$ is, independently, selected from —H, alkyl, alkenyl, alkynyl, cycloalkyl, cycloalkenyl, heterocyclyl, aryl, aralkyl, heteroaryl, heteroaralkyl, or —C(=O)CH$_3$; or $R^2$ and $R^3$ taken together with the nitrogen to which they are bonded represent a 3- to 8-membered heterocyclyl ring which contains 1 to 3 heteroatoms selected from O, N, S, and P;

$R^4$ is —H, alkyl, alkenyl or aralkyl;

$R^5$ and $R^6$ are each —H, or $R^5$ and $R^6$ taken together form a bond;

$R^7$ is —H, alkyl, alkenyl, alkynyl, cycloalkyl, cycloalkenyl, heterocyclyl, aryl, aralkyl, heteroaryl, or heteroaralkyl; and each instance of $R^8$ and $R^9$ is, independently, selected from —H, alkyl, alkenyl, alkynyl, cycloalkyl, cycloalkenyl, heterocyclyl, aryl, aralkyl, heteroaryl, or heteroaralkyl; or $R^8$ and $R^9$ taken together represent a 3 to 8 membered optionally substituted heterocyclyl ring which contains 1 to 3 heteroatoms selected from O, N, S, and P.

In certain embodiments, the percent sulfur of the composition is greater than 0.05 percent as measured by Elemental Analysis.

In certain embodiments, the composition is a stable composition.

In certain embodiments, the composition is stable at 40° C. and 75% relative humidity for at least one day.

In certain embodiments, the sulfur-containing compound is a sulfite.

In certain embodiments, the sulfur-containing compound is a reducing agent. As used herein, a "reducing agent" is an agent sufficient to reduce the benzoquinone group of a compound of formula (II) to the hydroquinone compound of formula (I).

In certain embodiments, the sulfur-containing compound is a sulfite reducing agent or another sulfur-containing compound which has similar reducing capacity to that of sulfites. In certain embodiments, the sulfur-containing compound is a sulfite reducing agent.

Exemplary sulfite reducing agents include, but are not limited to, sodium sulfite, sodium metabisulfite, sodium bisulfite, sodium hydrosulfite, sodium formaldehyde sulfoxylate, potassium bisufite, and potassium metabisulfite. In certain embodiments, the sulfite reducing agent is sodium hydrosulfite.

Also provided is a method for preparing a formulation comprising the additional step of:

(iv) mixing the precipitate of step (iii) with one or more excipients to provide a formulation.

In certain embodiments, the one or more excipients is selected from sugars, polymers, surfactants, antioxidants, solubilizing or suspending agents, or combinations thereof.

In certain embodiments, the mixing step (iv) provides a homogenous formulation (e.g., a clear solution). In certain embodiments, the mixing step (iv) provides a heterogenous formulation (e.g., an emulsion, suspension). In certain embodiments, the heterogenous formulation is an emulsion.

In certain embodiments, the method further comprises the step (v) of drying the formulation. In certain embodiments, the formulation is dried under reduced pressure (e.g., under vacuum, by lyophilization).

In certain embodiments, the dried formulation is a powder, sponge or foam.

EXEMPLIFICATION

The invention now being generally described, it will be more readily understood by reference to the following examples, which are included merely for purposes of illustration of certain aspects and embodiments of the present invention, and are not intended to limit the invention.

Example 1

Preparation of 17-amino geldanamycin hydroquinone HCl Salt (17-AG-HQ-HCl)

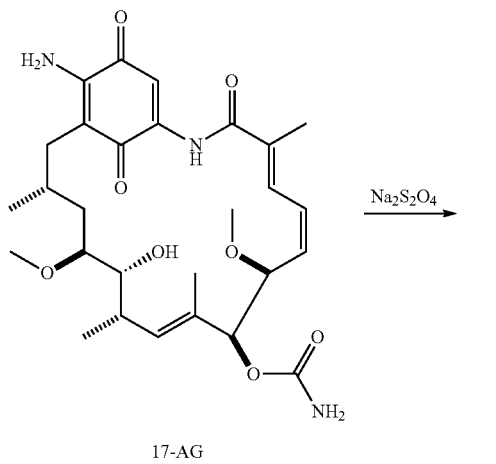

17-AG

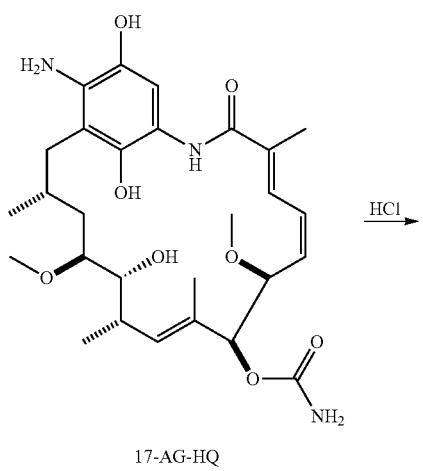

17-AG-HQ

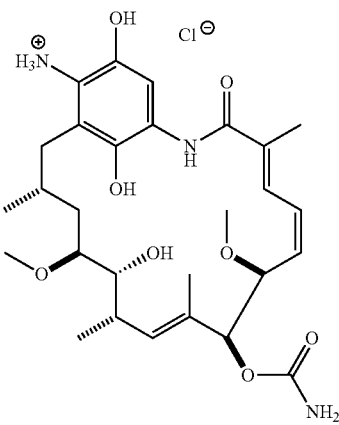

17-AG-HQ-HCl

Step 1: Geldanamycin (1.12 g, 2 mmol, 1 eq) was added to anhydrous dichloromethane (5 mL). NH$_3$ in methanol was added to this solution (9 mL, 100 mmol, 50 eq) and was allowed to stir for 24 hours. The reaction solution was diluted with dichloromethane and extracted with water, followed by dilute HCl. The organic layer was collected washed with brine, dried over Na$_2$SO$_4$ and concentrated under reduced pressure to yield a purple solid. This solid was recrystalized twice from acetone/heptanes to yield 0.239 of 17-amino-17-demethoxygeldanamycin (17-AG).

Step 2: 17-amino-17-demethoxygeldanamycin (17-AG) (0.55 g, 1 mmol, 1 eq) was dissolved in EtOAc (100 mL). A freshly prepared solution of 10% aqueous sodium hydrosulfite (Na$_2$S$_2$O$_4$) (10 mL, 0.68 M) was added and stirred for 1 hour at room temperature. The color changed from dark purple to bright yellow, indicating a complete reaction. The layers were separated and the organic phase was dried with magnesium sulfate. The drying agent was rinsed with EtOAc (2×10 mL). An aliquot of the organic phase was taken, concentrated under reduced pressure and analyzed for sulfur content. Elemental Analysis for 17-AG-HQ of Example 1 is listed in Table 1.

Step 3: The organic phase was acidified with 1.5 M HCl in EtOAc (1 mL) to pH 2 over 20 minutes. The resulting slurry was stirred for 1.5 h at room temperature. The solids were isolated by filtration, rinsed with ethyl acetate (10 mL) and dried under vacuum to provide the 17-AG-HQ HCl salt of Example 1 (0.524 g, 87% yield).

Figure 8:
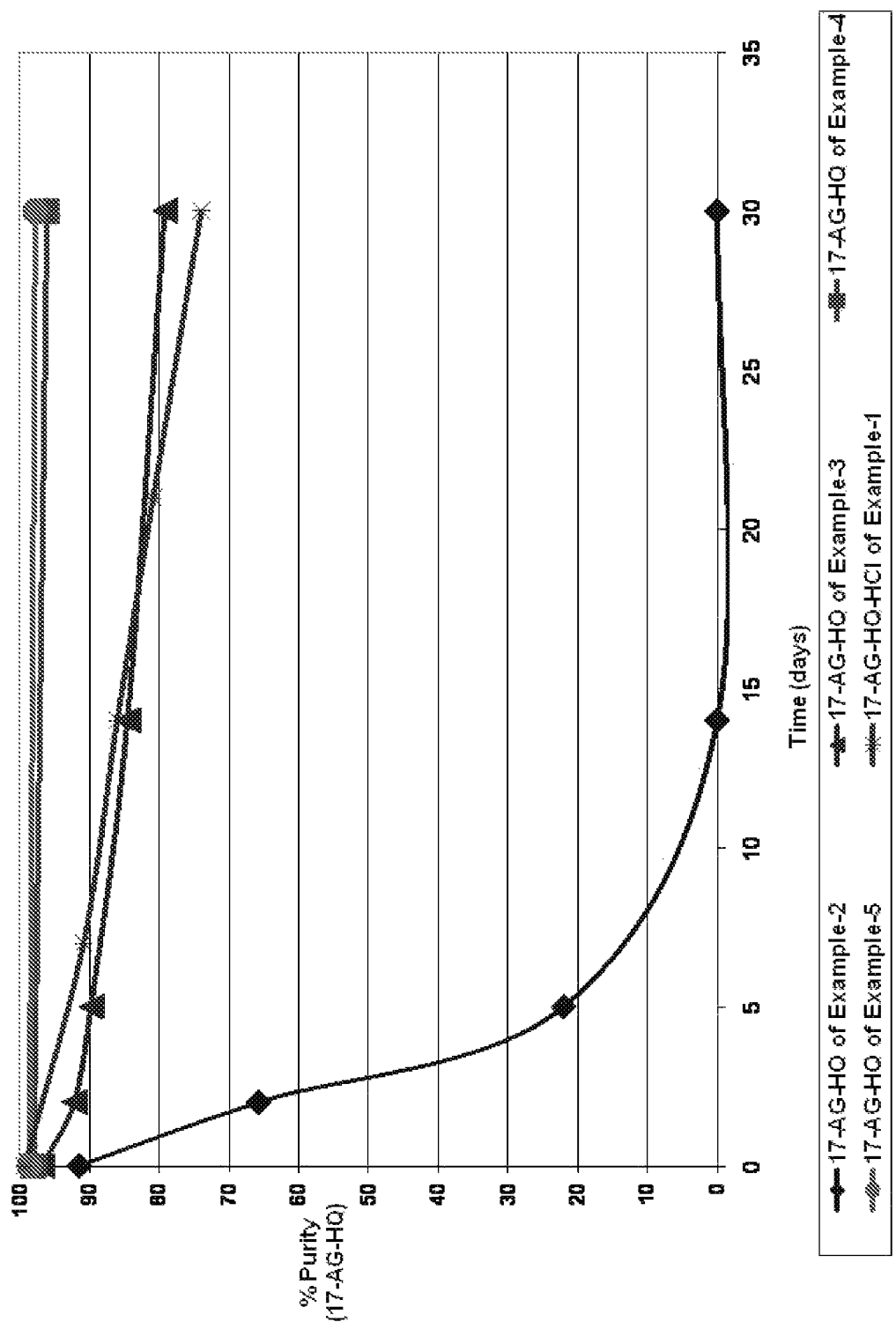
FIG. 8 is a graph depicting the stability of 17-AG-HQ of Example 1 to 5 at 40° C. and 75% relative humidity (RH).

The stability data for 17-AG-HQ-Cl salt when kept at 40° C. and 75% relative humidity (RH) is depicted in FIG. 8 (see also Table 2).

Examples 2-6

Preparation of Compositions Comprising 17-amino geldanamycin hydroquinone (17-AG-HQ)

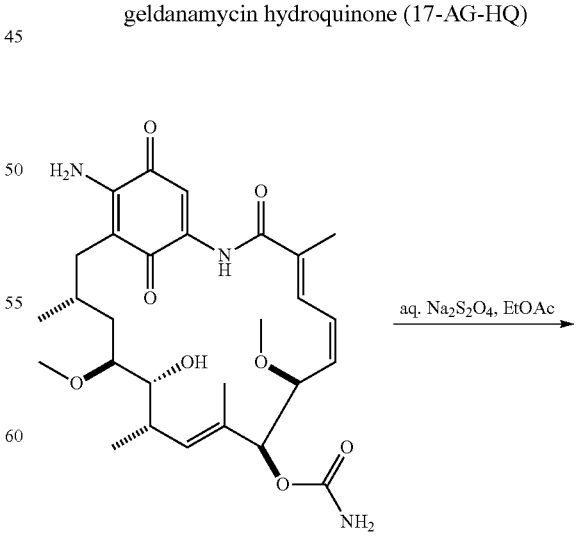

17-AG

-continued

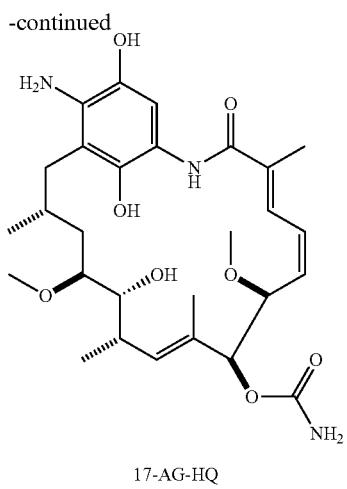

17-AG-HQ

Example 2

To a solution of 17-aminogeldanamycin (17-AG) (6.0 g, 11 mmol, 1.0 equiv) in ethyl acetate (1000 mL) at 22° C. was added aqueous sodium hydrosulfite ($Na_2S_2O_4$) (120 g in 1000 mL; 0.68M). The biphasic mixture was stirred vigorously for 60 minutes until the purple solution turned yellow. The organic layer was separated, washed with 1000 mL water and dried over magnesium sulfate (18 g). The organic solution was filtered and the drying agent washed with 500 mL ethyl acetate. The solution was concentrated under reduced pressure to obtain 17-AG-HQ of Example 2 as dark rusty-yellow solid (4.92 g, 8.98 mmol, 82% yield). Percent Purity (HPLC-UV): 92%.

Figure 2:
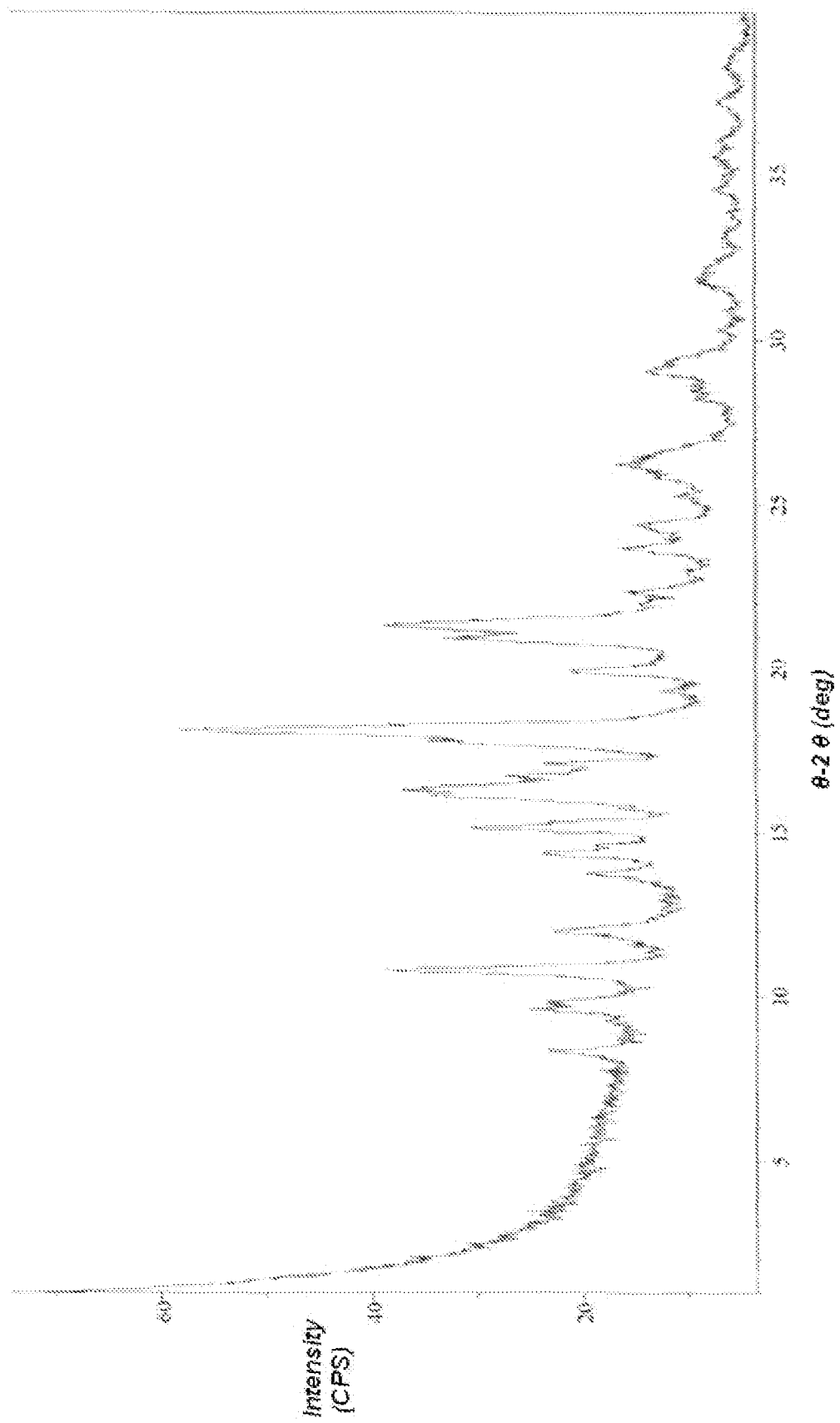
FIG. 2 depicts the X-ray Powder Diffraction (XRPD) pattern of 17-AG-HQ of Example 2.
Figure 3:
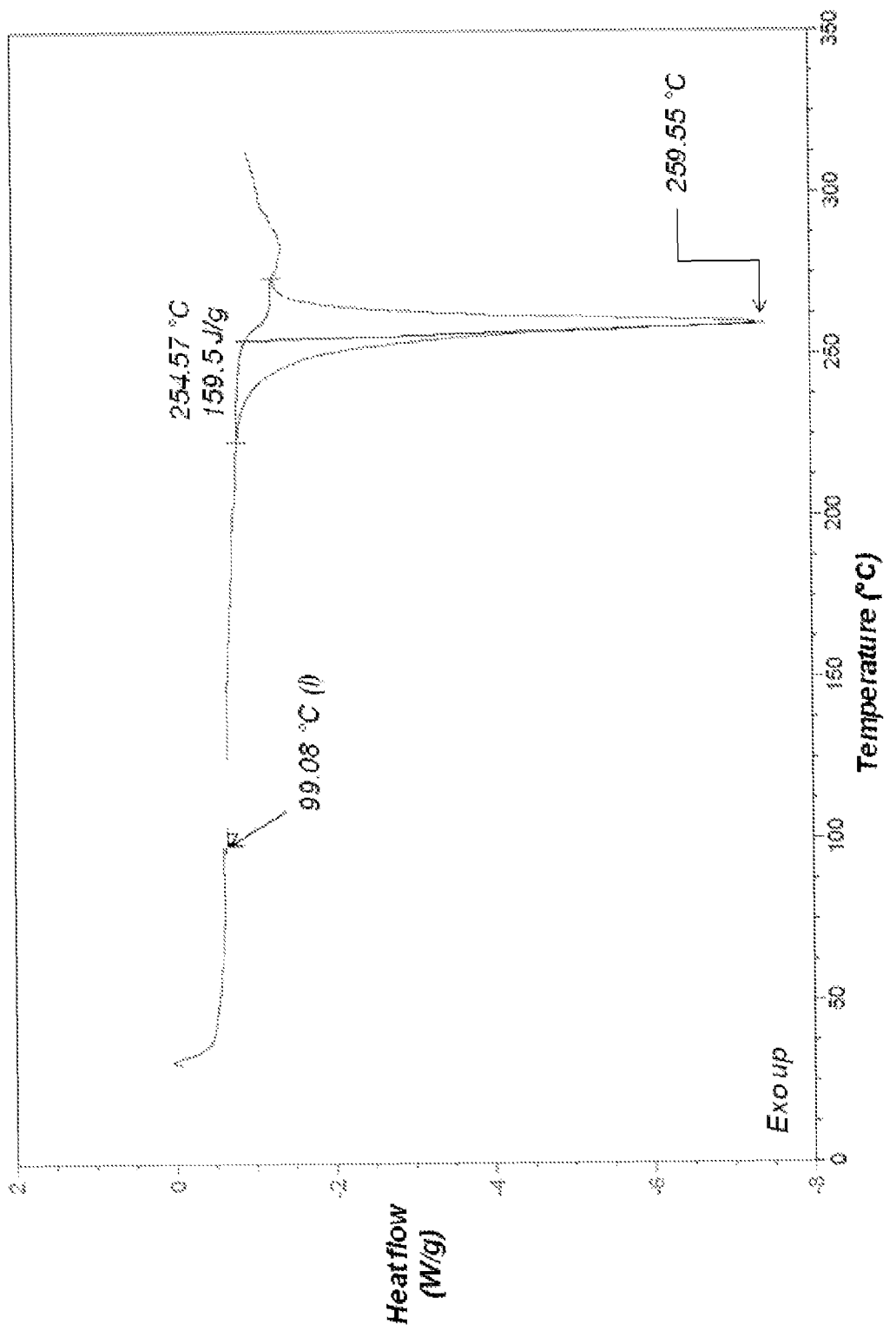
FIG. 3 depicts the Differential Scanning Calorimetry (DSC) thermogram of 17-AG-HQ of Example 2 showing an endotherm at 259.55° C.

Exemplary HPLC, X-Ray powder diffraction (XRPD) and differential scanning calorimetry (DSC) data for the above compound is depicted in FIGS. 1, 2 and 3, respectively. Elemental Analysis for 17-AG-HQ of Example 2 is listed in Table 1.

17-AG-HQ of Example 2 was found to be less stable than 17-AG-HQ HCl salt of Example 1 (i.e., more prone to oxidation). The stability data for 17-AG-HQ of Example 2 when kept at 40° C. and 75% relative humidity (RH) is depicted in FIG. 8 (see Table 2 for tabulated stability data). It was observed that 17-AG-HQ of Example 2 completely oxidizes to its quinone form in two weeks at 40° C. and 75° RH as determined by HPLC.

Example 3

To a solution of 17-aminogeldanamycin (17-AG) (9.0 g, 16.5 mmol, 1.0 equiv) in ethyl acetate (1250 mL) at 22° C. was added aqueous sodium hydrosulfite ($Na_2S_2O_4$) (178 g in 1250 mL; 0.8M). The biphasic mixture was stirred vigorously until the purple solution turned yellow (60 min) and resulted in a precipitate in the organic layer. The precipitate was filtered and redissolved in 500 mL of ethyl acetate. The organic layer was separated, washed with 500 mL brine and dried over magnesium sulfate. The organic solution was filtered and the drying agent washed with 500 mL ethyl acetate. The solution was concentrated under reduced pressure to obtain an orange solid residue. The residue was redissolved in ethyl acetate and concentrated under reduced pressure to obtain 17-AG-HQ of Example 3 as a bright yellow solid (8.53 g, 15.58 mmol, 94% yield). Percent Purity (HPLC-UV): 97%.

Figure 4:
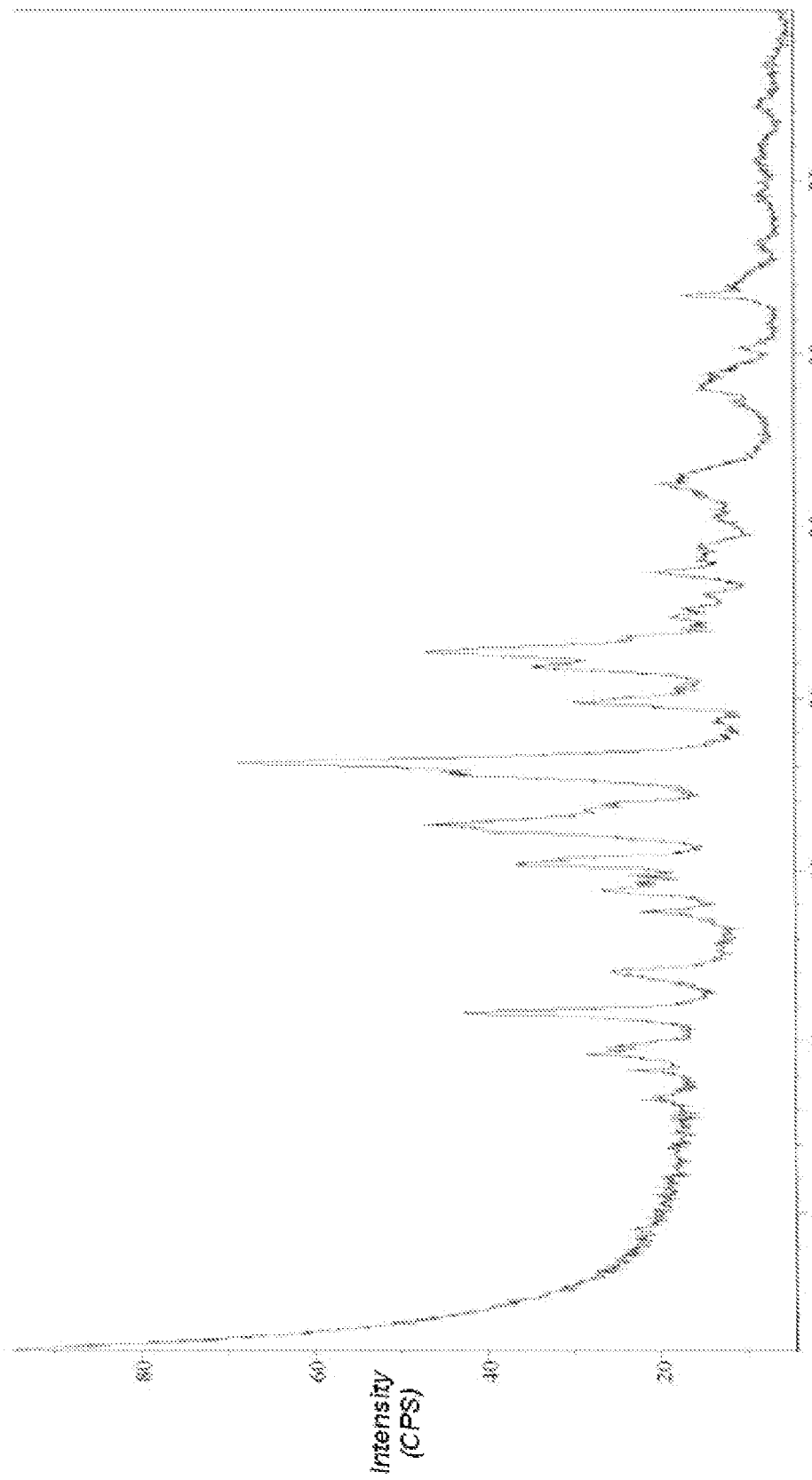
FIG. 4 depicts the X-ray Powder Diffraction (XRPD) pattern of 17-AG-HQ of Example 3.
Figure 5:
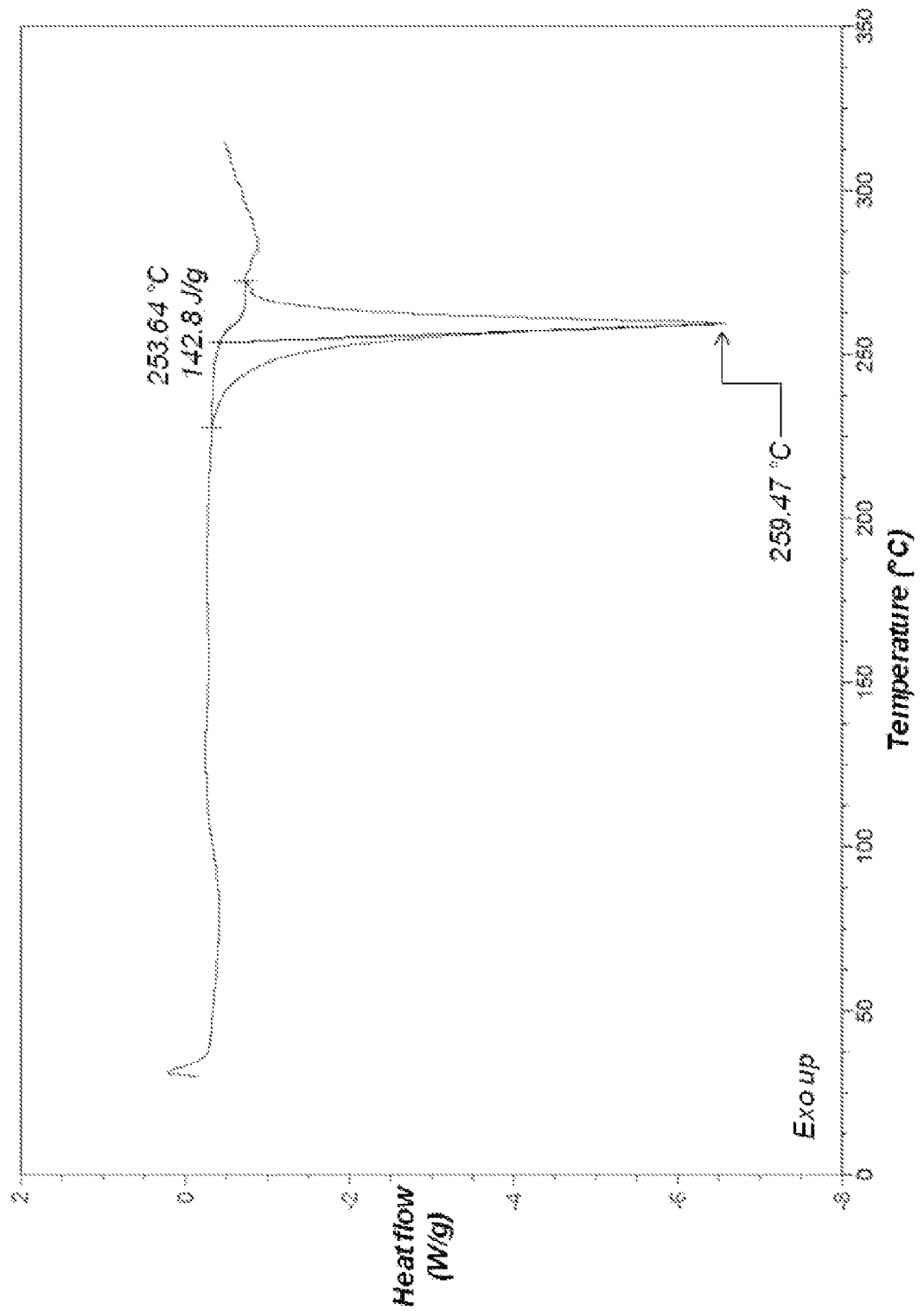
FIG. 5 depicts the Differential Scanning Calorimetry (DSC) thermogram of 17-AG-HQ of Example 3 showing an endotherm at 259.47° C.

Exemplary XRPD and DSC data are depicted in FIGS. 4 and 5, respectively. Elemental Analysis for 17-AG-HQ of Example 3 is listed in Table 1.

When compared to 17-AG-HQ of Example 2, 17-AG-HQ of Example 3 shows greater stability over a period of time when kept at 40° C. and 75% relative humidity (RH) (see FIG. 8 and Table 2). The greater stability can be attributed to a higher sulfur content of 17-AG-HQ of Example 3 as compared to the sulfur content of 17-AG-HQ of Example 2 (see Table 1).

Example 4

To a solution of 17-aminogeldanamycin (17-AG) (1.0 g, 1.83 mmol, 1.0 equiv) in ethyl acetate (139 mL) at 22° C. was added aqueous sodium hydrosulfite ($Na_2S_2O_4$) (20 g in 139 mL; 0.8M). The biphasic mixture was stirred vigorously until the purple solution turned yellow (30 min) and resulting in a precipitate in the organic layer. The precipitated solid and organic layer, together, were separated from the aqueous layer and washed with 150 mL brine. The precipitated solid was then filtered from the organic layer and the organic layer was discarded. The precipitated solid was dried in a vacuum oven (30° C., 24 hours) to obtain 17-AG-HQ of Example 4 as a bright yellow solid (680 mg, 1.24 mmol, 68% yield). Percent Purity (HPLC-UV): 98%.

Figure 6:
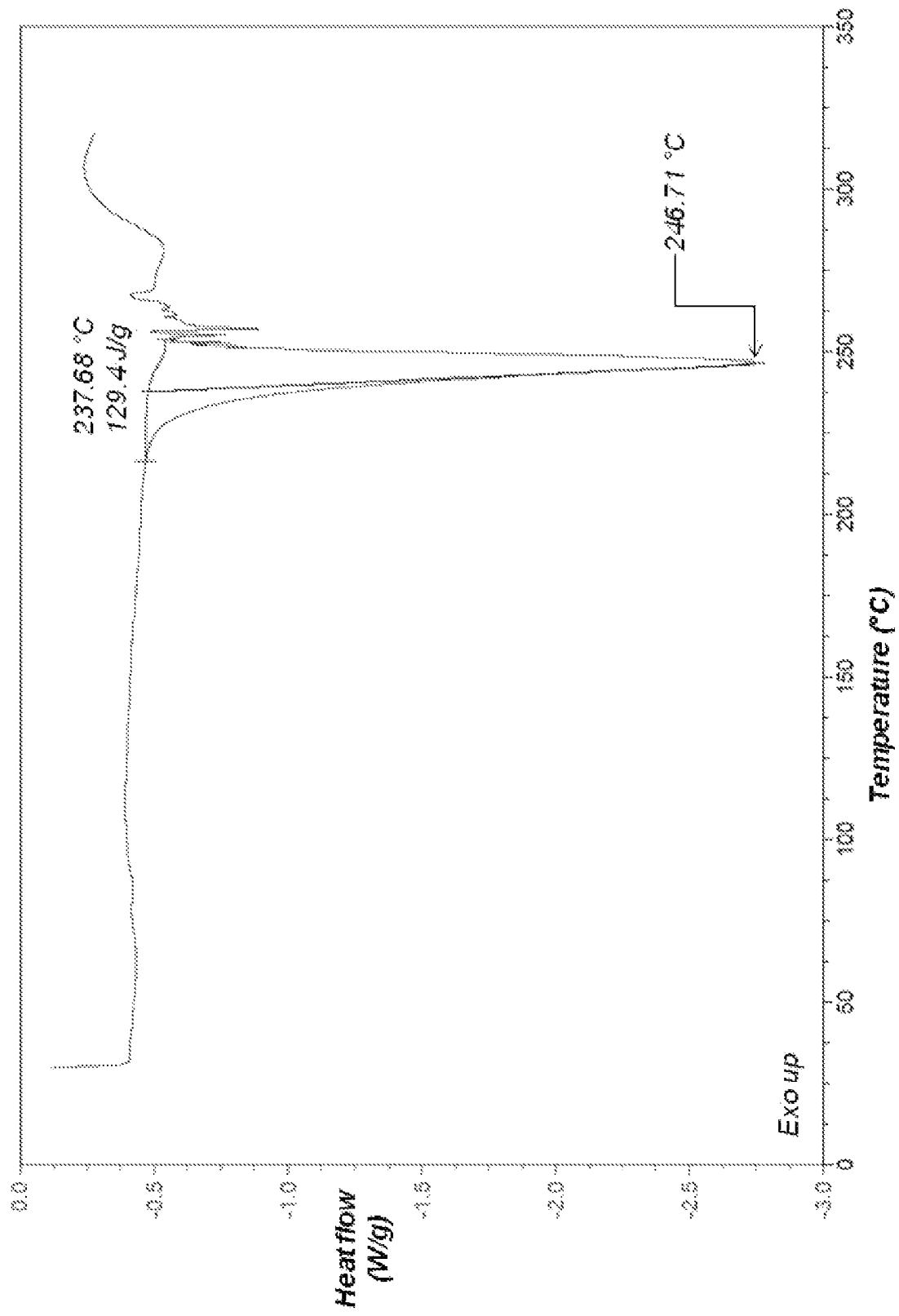
FIG. 6 depicts the Differential Scanning Calorimetry (DSC) thermogram of 17-AG-HQ of Example 4 showing an endotherm at 246.71° C.

The DSC of the above compound is depicted in FIG. 6. Elemental Analysis for 17-AG-HQ of Example 4 is listed in Table 1.

When compared to Examples 2 and 3, 17-AG-HQ of Example 4 shows greater stability over a period of time when kept at 40° C. and 75% relative humidity (RH) (see FIG. 8 and Table 2). The greater stability can be attributed to a higher sulfur content of 17-AG-HQ of Example 4 compared to the sulfur content of 17-AG-HQ of Examples 2 and 3 (see Table 1).

Example 5

To a solution of 17-aminogeldanamycin (17-AG) (1.0 g, 1.83 mmol, 1.0 equiv) in ethyl acetate (139 mL) at 22° C. was added aqueous sodium hydrosulfite ($Na_2S_2O_4$) (20 g in 139 mL; 0.8M). The biphasic mixture was stirred vigorously until the purple solution turned yellow (30 min) and resulting in a precipitate in the organic layer. The precipitated solid was filtered directly from the reaction mixture and dried in a vacuum oven (30° C., 24 hours) to obtain 17-AG-HQ of Example 5 as a bright yellow solid (730 g, 1.33 mmol, 73% yield). Percent Purity (HPLC-UV): 98.6%.

Figure 7:
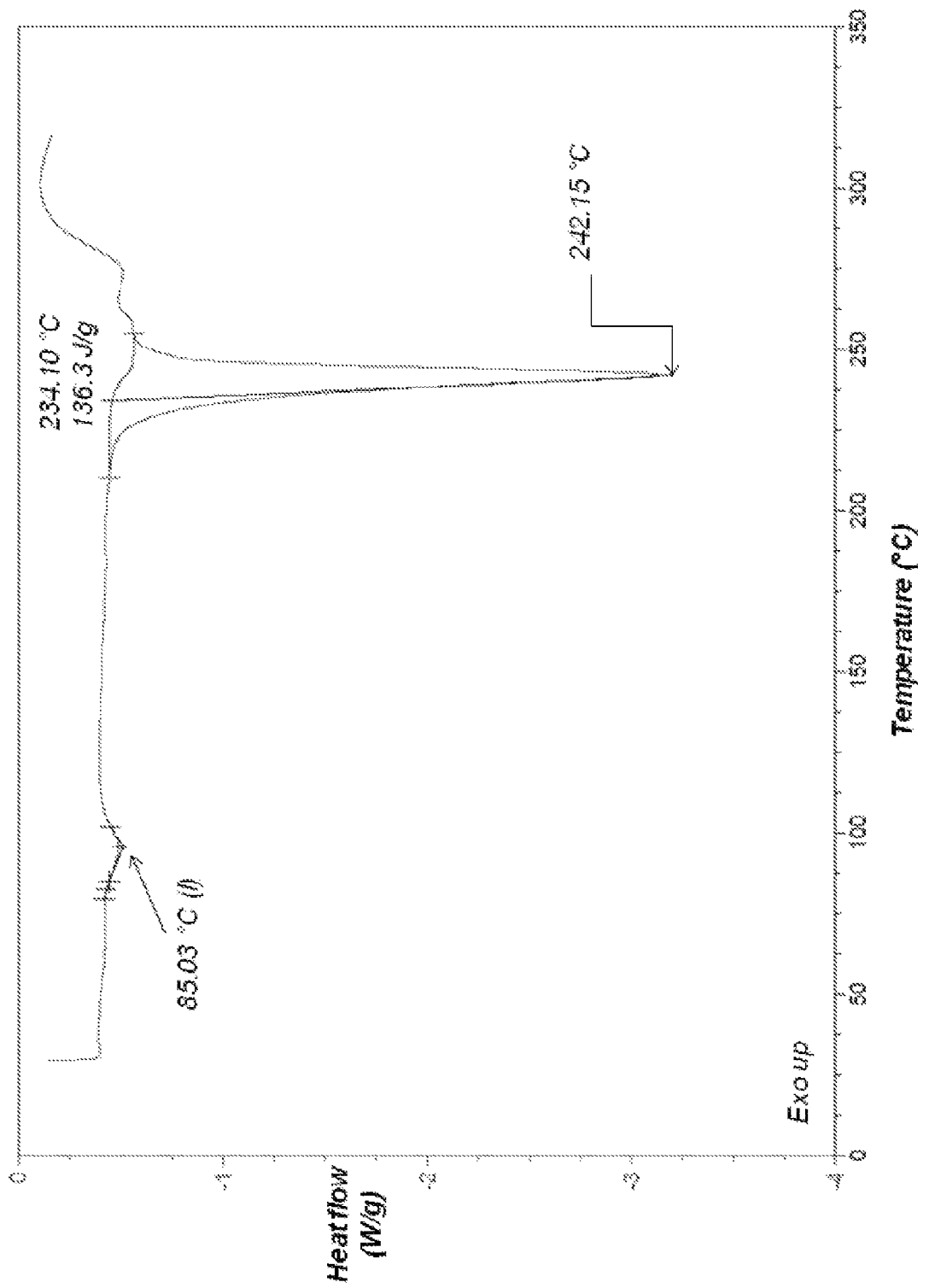
FIG. 7 depicts the Differential Scanning Calorimetry (DSC) thermogram of 17-AG-HQ of Example 5 showing an endotherm at 242.15° C.

The DSC of the above compound is depicted in FIG. 7. Elemental Analysis of 17-AG-HQ of Example 5 is listed in Table 1.

When compared to Examples 2, 3 and 4, the 17-AG-HQ of Example 5 shows the greatest stability over a period of time when kept at 40° C. and 75% relative humidity (RH) (see FIG. 8 and Table 2). The high stability can be attributed to a higher sulfur content of 17-AG-HQ of Example 5 compared to the sulfur content of 17-AG-HQ of Examples 2, 3 and 4 (see Table 1).

Example 6

Example 6A. To a solution of 17-aminogeldanamycin (17-AG) (3.03 grams, 5.17 mmol, 1.0 equiv) in ethyl acetate (360 mL) at 22° C. was added aqueous sodium hydrosulfite ($Na_2S_2O_4$) (12.5 g in 125 mL; 0.57M). The biphasic mixture was stirred vigorously until the purple mixture turned yellow (30 minutes). At that time, half of the organic layer was removed from the reaction and was used in the preparation of 17-AG-HQ of Example 6B (see below). The remaining reaction was allowed to stir until a precipitate formed (2 h). The organic layer was filtered and the precipitate was washed with several aliquots of EtOAc (25 mL, 1×) and water (25 mL, 1×). The washed precipitate was dried under vacuum to obtain 17-amino-geldanamycin hydroquinone (17-AG-HQ) of Example 6A as a bright yellow solid (1.223 g, 2.23 mmol, 40.0% yield). Percent Purity (HPLC-UV): 97%.

Example 6B. To the organic filtrate from Example 6A was added an aqueous sodium hydrosulfite ($Na_2S_2O_4$) (10 g in 100 mL; 0.57M). The biphasic mixture was stirred vigorously for 10 min to ensure full reconversion to 17-AG-HQ. The yellow organic layer was separated and was washed with 100 mL NaCl and dried with $MgSO_4$. The organic solution was filtered and the drying agent was rinsed with EtOAc (100 mL). The organic layers were combined and the solution was concentrated under reduced pressure to obtain 17-amino-geldanamycin hydroquinone (17-AG-HQ) of Example 6B as a rusty yellow solid (1.470 g, 2.68 mmol, 48.8% yield). Percent Purity (HPLC-UV): 96%.

Figure 9:
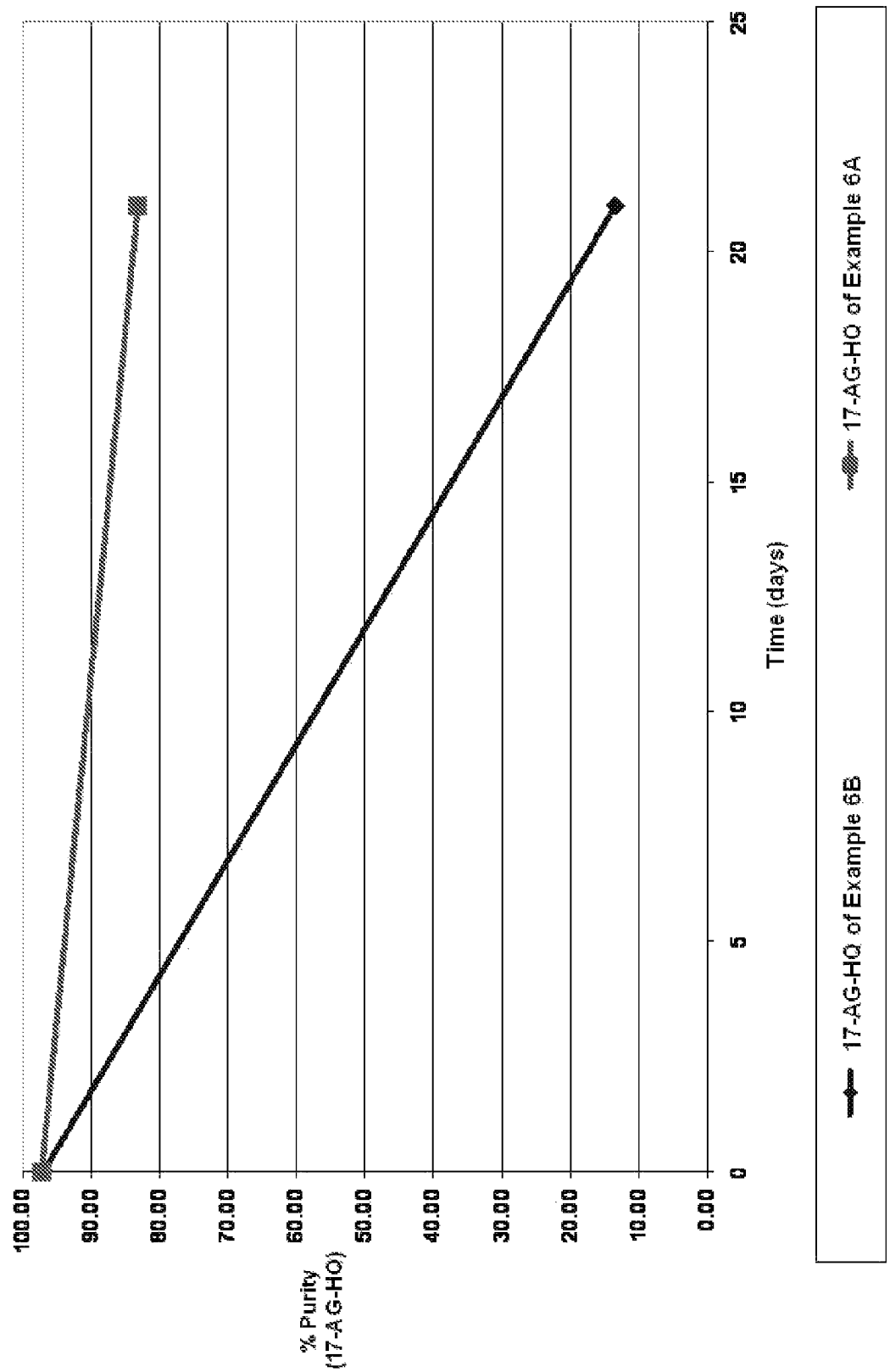
FIG. 9 is a graph depicting the stability of 17-AG-HQ of Example 6A and 6B at 40° C. and 75% relative humidity (RH).

Comparison of Examples 6A and 6B. When compared to 17-AG-HQ of Example 6B, 17-AG-HQ of Example 6A shows greater stability over a period of time when kept at 40° C. and 75% relative humidity (RH) (see FIG. 9 and Table 2). It was observed that 17-AG-HQ of Example 6B completely oxidizes into its quinone form in 3 weeks at 40° C. and 75% RH as determined by HPLC. The greater stability can be attributed to a higher sulfur content of 17-AG-HQ of Example 6A as compared to the sulfur content of 17-AG-HQ of Example 6B (See Table 1).

TABLE 1

| 17-AG-HQ | % Carbon | % Hydrogen | % Nitrogen | % Sulfur |
|---|---|---|---|---|
| Example 1 | 56.28 | 7.84 | 6.62 | <0.05 |
| Example 2 | 60.90 | 7.72 | 7.42 | <0.05 |
| Example 3 | 60.26 | 7.72 | 7.30 | 0.51 |
| Example 4 | 48.83 | 6.81 | 6.12 | 1.37 |
| Example 5 | 44.85 | 5.46 | 5.48 | 5.35 |
| Example 6A | 50.91 | 7.10 | 6.29 | 1.72 |
| Example 6B | 60.30 | 7.79 | 7.09 | <0.05 |

Stability data for the compounds and compositions of Examples 1-6 is summarized in Table 2 below.

TABLE 2

| | Percent Purity of 17-AG-HQ | | | | | |
|---|---|---|---|---|---|---|
| Composition | T = 0 Days | T = 2 Days | T = 5 Days | T = 14 Days | T = 21 Days | T = 30 Days |
| 17-AG-HQ-HCl salt | 99 | — | — | 88 | — | 74 |
| 17-AG-HQ of Example 2 | 92 | 66 | 22 | 0 | — | 0 |
| 17-AG-HQ of Example 3 | 97 | 93 | 91 | 87 | 81 | 79 |
| 17-AG-HQ of Example 4 | 99 | — | — | — | — | 97 |
| 17-AG-HQ of Example 5 | 99 | — | — | — | — | 98 |
| 17-AG-HQ of Example 6A | 97 | — | — | — | 83 | — |
| 17-AG-HQ of Example 6B | 97 | — | — | — | 13 | — |

In general, use of a higher concentration of sodium hydrosulfite as reductant (compare Examples 2 and 3), formation and isolation of a 17-AG-HQ precipitate (compare Examples 6A and 6B), and/or limiting the synthetic workup of the reaction, such as foregoing an aqueous workup step (compare Examples 4 and 5), can provide a hydroquinone having greater sulfur content and higher stability.

Example 7

Preparation of 17-benzylamino-geldanamycin (17-BAG)

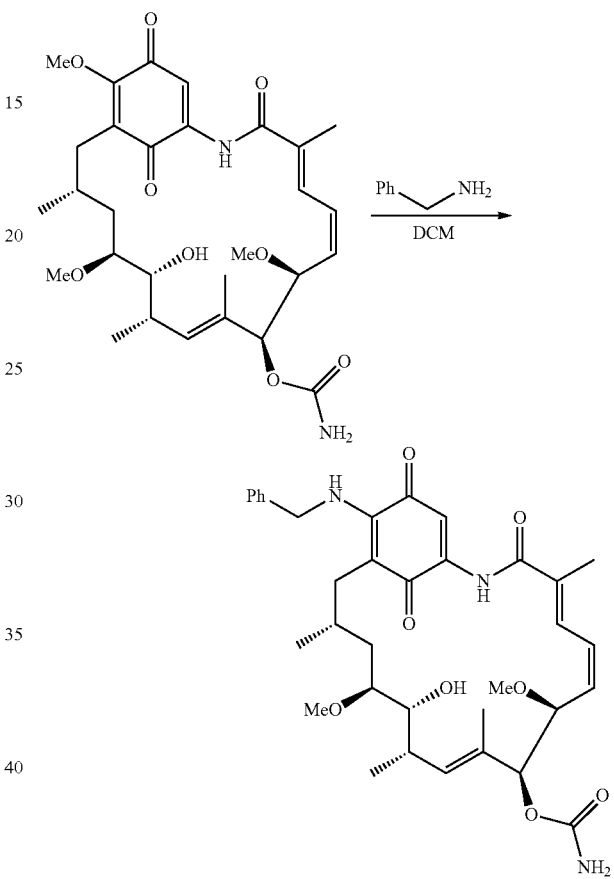

To a solution of geldanamycin (4.00 g, 7.13 mmol, 1 eq.) in DCM (143 mL, 0.050 M) was added benzylamine (4.67 mL, 42.8 mmol, 6 eq.). The reaction was allowed to stir at 22° C. for 24 hours under a nitrogen atmosphere. During this time, the reaction mixture changed from a yellow solution to a dark purple solution. The reaction solution was quenched with hydrochloric acid (7.13 mL, 6 N, 6 eq) and was diluted with 300 mL ethyl acetate. The organic layer was washed with 150 mL saturated NaCl. The aqueous layer was extracted with 150 mL ethyl acetate (3×) to remove the purple product. The organic layers were collected, dried over $Na_2SO_4$ and concentrated under reduced pressure to yield a purple solid. The purple solid was purified by silica gel column chromatography to yield 17-benzylamino-geldanamycin (17-BAG) (4.50 g, 7.08 mmol, 99%). Percent Purity (HPLC-UV): 99.5%.

Example 8

Preparation of 17-benzylamino-geldanamycin hydroquinone (17-BAG-HQ)

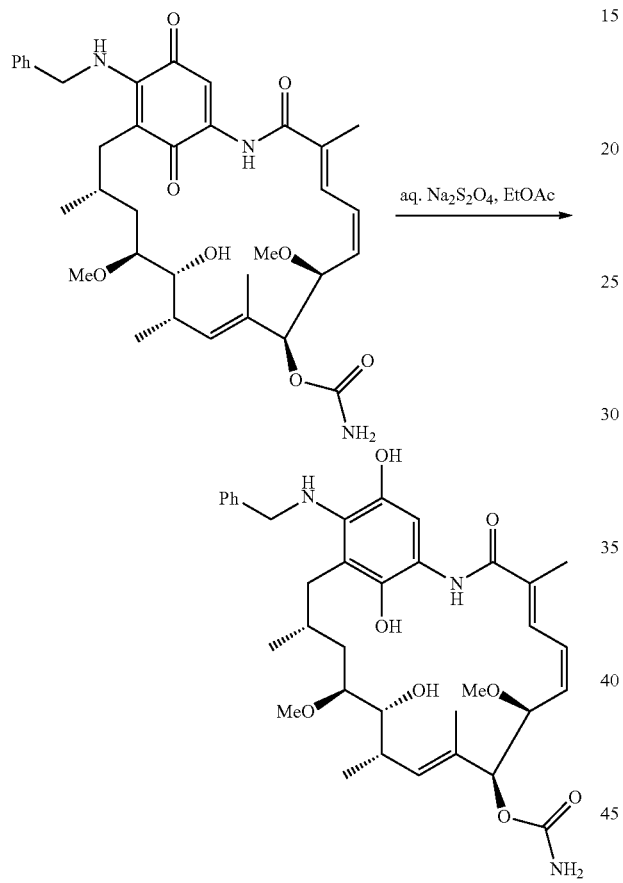

Example 8A. To a solution of 17-benzylamino-geldanamycin (17-BAG) (3.5 g, 5.51 mmol, 1 eq) in ethyl acetate (350 mL) at 22° C. was added aqueous sodium hydrosulfite ($Na_2S_2O_4$) (12.5 g in 125 mL; 0.57 M). The biphasic mixture was stirred vigorously until the purple mixture turned yellow (60 minutes). At that time, half of the organic layer was removed from the reaction and was used in the preparation of 17-BAG-HQ of Example 8B (see below). The $Na_2S_2O_4$ aqueous layer was replaced with 125 mL of freshly prepared solution of aqueous sodium hydrosulfite ($Na_2S_2O_4$) (25 g in 125 mL; 1.1 M). The reaction mixture was stirred vigorously at 22° C. for 72 h under a nitrogen atmosphere until a precipitate formed. The organic layer was filtered and the precipitate was washed with several aliquots of ethyl acetate (25 mL, 3×) and water (25 mL, 3××). The washed precipitate was dried under vacuum to obtain 17-benzylamino-geldanamycin hydroquinone (17-BAG-HQ) of Example 8A as a bright yellow solid (941.0 mg, 1.536 mmol, 27.9% Yield). Percent Purity (HPLC-UV): 97%.

Example 8B. The organic layer removed at T=60 min in Example 8A above was washed with saturated NaCl, dried with $Na_2SO_4$, and filtered. The mixture was concentrated under reduced pressure to yield 17-benzylamino-geldanamycin hydroquinone (17-BAG-HQ) of Example 8B as an orange-yellow solid (1.025 g, 1.60 mmol, 29.2% Yield). Percent Purity (HPLC-UV): 97%.

Figure 10:
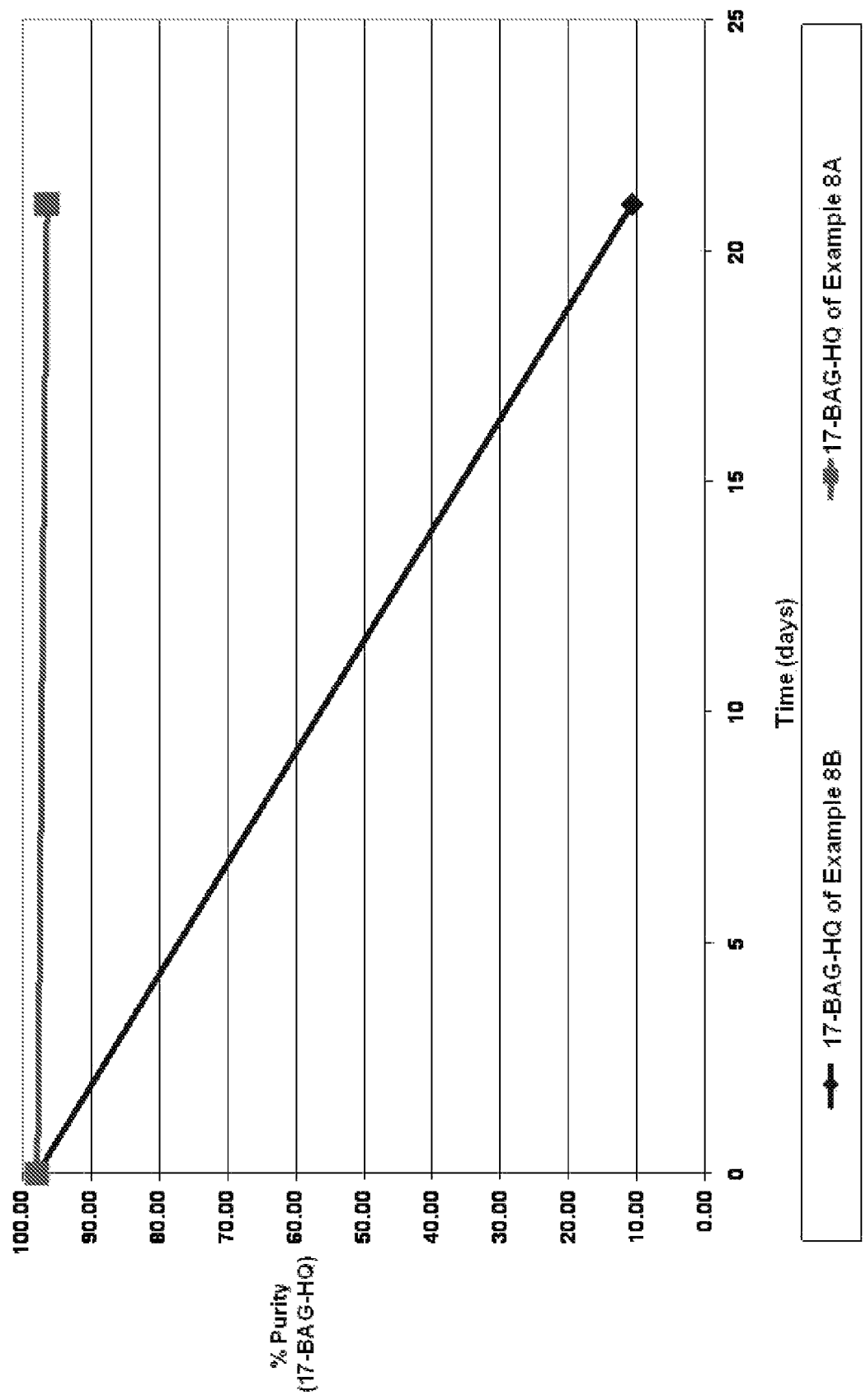
FIG. 10 is a graph depicting the stability of 17-BAG-HQ of Example 8A and 8B at 40° C. and 75% relative humidity (RH).

Comparison of Examples 8A and 8B. When compared to 17-BAG-HQ of Example 8B, the 17-BAG-HQ of Example 8A shows greater stability over a period of time when kept at 40° C. and 75% relative humidity (RH) (see FIG. 10 and Table 4). The greater stability can be attributed to a higher sulfur content of 17-BAG-HQ of Example 8A as compared to the sulfur content of 17-BAG-HQ of Example 8B (See Table 3).

TABLE 3

| Composition | % Carbon | % Hydrogen | % Nitrogen | % Sulfur |
|---|---|---|---|---|
| 17-BAG-HQ of Example 8A | 61.85 | 7.18 | 6.24 | 1.84 |
| 17-BAG-HQ of Example 8B | 64.11 | 7.84 | 5.84 | <0.05 |

TABLE 4

| | Percent Purity of 17-BAG | |
|---|---|---|
| Composition | T = 0 Days | T = 21 Days |
| 17-BAG-HQ of Example 8A | 98 | 96 |
| 17-BAG-HQ of Example 8B | 98 | 11 |

Example 9

Preparation of 17-(2-fluoroethylamino)-geldanamycin (17-FEAG)

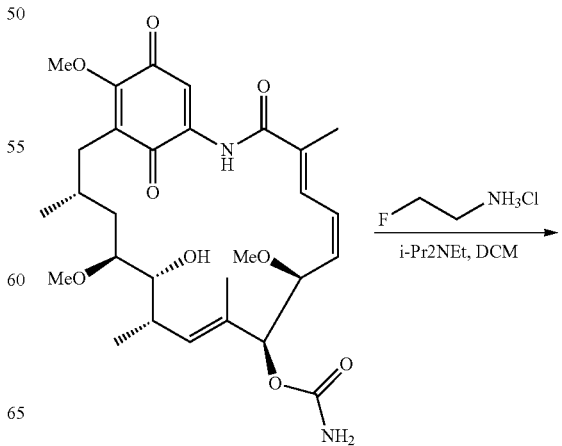

-continued

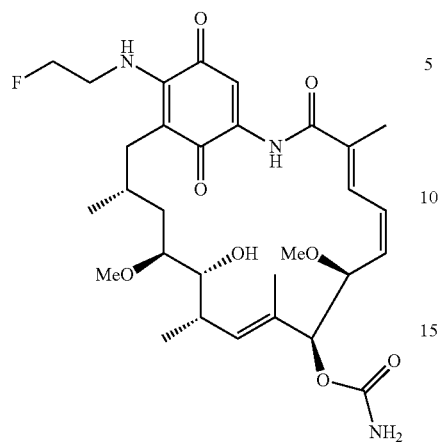

To a solution of geldanamycin (4.00 g, 7.13 mmol, 1 eq.) in DCM (143 mL, 0.050 M) was added 2-fluoroethylamine hydrochloride (7.10 g, 71.3 mmol, 8 eq) and diisopropylethylamine (24.85 mL, 143 mmol, 20 eq.). The reaction was allowed to stir at 22° C. for 24 h under a nitrogen atmosphere. During this time, the reaction mixture changed from a yellow solution to a dark purple solution. The reaction was quenched with hydrochloric acid (23.78 mL, 6 N, 20 eq.), diluted with 350 mL EtOAc and washed with 150 mL saturated NaCl. The aqueous layer was extracted with 150 mL ethyl acetate (3×) to remove the purple product. The organic layers were collected, dried over MgSO$_4$ and concentrated under reduced pressure to yield 17-(2-fluoroethylamino)-geldanamycin (17-FEAG) (4.20 g, 7.10 mmol, 99%). Percent Purity (HPLC-UV): 99%.

Example 10

Preparation of 17-(2-fluoroethylamino)-geldanamycin hydroquinone (17-FEAG-HQ)

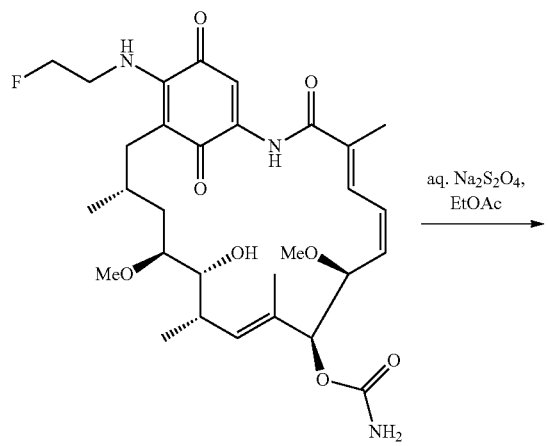

aq. Na$_2$S$_2$O$_4$, EtOAc

-continued

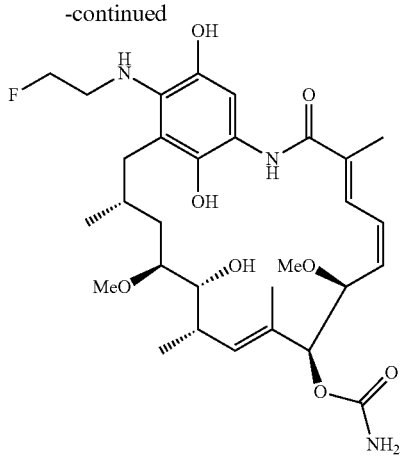

Example 10A. To a solution of 17-(2-fluoroethylamino)-geldanamycin (17-FEAG) (3.0 g, 5.07 mmol) in EtOAc (30 mL) was added freshly prepared 20% aqueous sodium hydrosulfite (Na$_2$S$_2$O$_4$) (25 g in 125 mL; 1.1 M). The biphasic mixture was stirred vigorously until the purple reaction mixture turned yellow (60 minutes) and a precipitate formed in the organic layer (24 h). The organic layer was filtered and the precipitate was washed with several aliquots of ethyl acetate (25 mL, 3×) and water (25 mL, 3×). The organic filtrate was reserved for use in the preparation of 17-FEAG-HQ of Example 10B (see below). The precipitate was dried under vacuum to obtain 17-(2-fluoroethylamino)-geldanamycin hydroquinone (17-FEAG-HQ) of Example 10A as a bright yellow solid (1.667 g, 2.81 mmol, 55.4% Yield). Percent Purity (HPLC-UV): 98%.

Example 10B. To the organic filtrate from Example 10A was added an aqueous solution of sodium hydrosulfite (Na$_2$S$_2$O$_4$) (20 g in 100 mL; 1.1 M). The biphasic mixture was stirred vigorously for an hour to ensure full conversion to 17-FEAG-HQ. The yellow organic layer was separated and was washed with 100 mL NaCl and dried with MgSO$_4$. The organic solution was filtered and the drying agent was rinsed with 100 mL EtOAc. The organic layers were combined and the solution was concentrated under reduced pressure to obtain 17-(2-fluoroethylamino)-geldanamycin hydroquinone (17-FEAG-HQ) of Example 10B as a rusty yellow solid (735.6 mg, 1.239 mmol, 24.4% Yield). Percent Purity (HPLC-UV): 97%.

Figure 11:
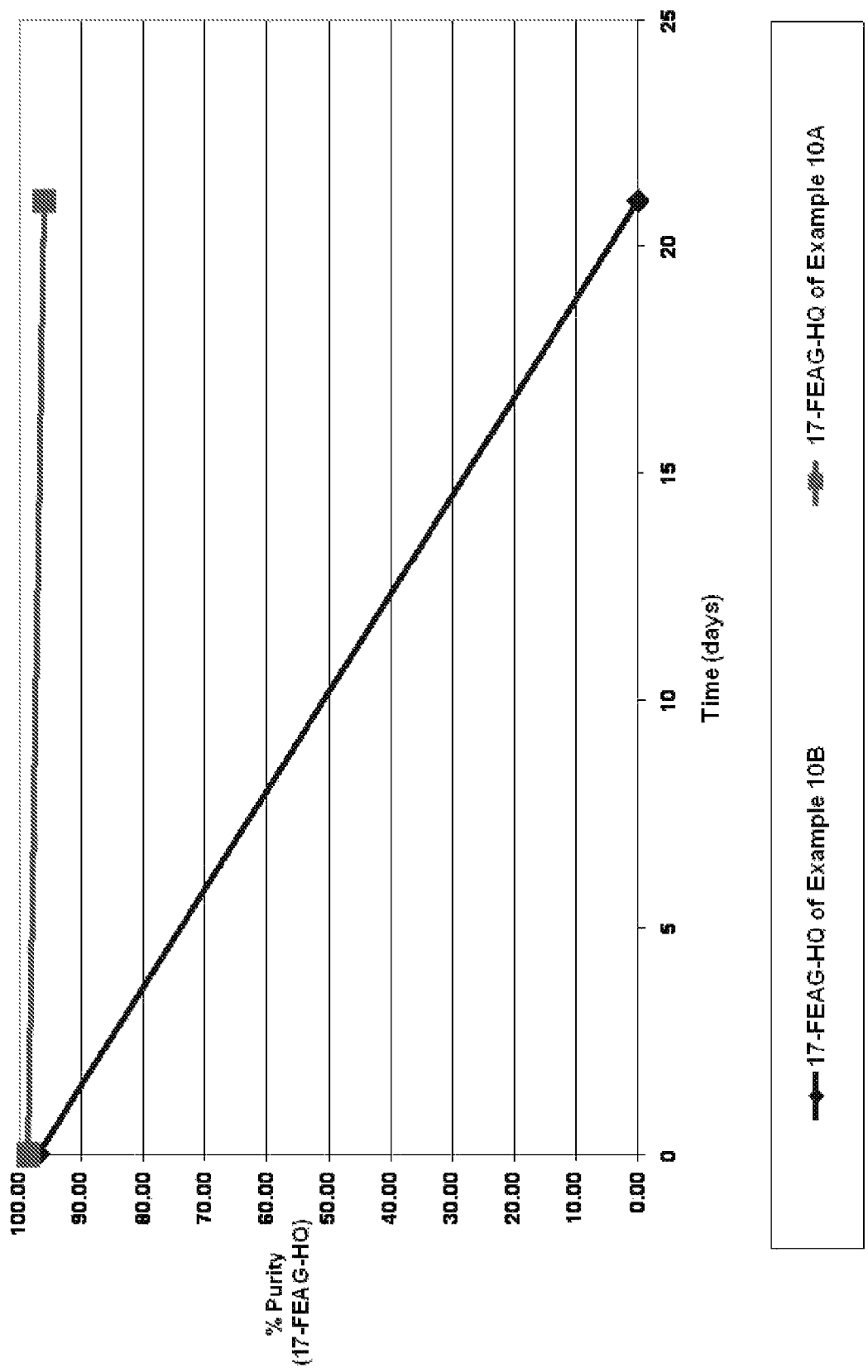
FIG. 11 is a graph depicting the stability of 17-FEAG-HQ of Example 10A and 10B at 40° C. and 75% relative humidity (RH).

Comparison of Examples 10A and 10B. When compared to 17-FEAG-HQ of Example 10B, 17-FEAG-HQ of Example 10A shows greater stability over a period of time when kept at 40° C. and 75% relative humidity (RH) (see FIG. 11 and Table 6). The greater stability can be attributed to a higher sulfur content of 17-FEAG-HQ of Example 10A as compared to the sulfur content of 17-FEAG-HQ of Example 10B (See Table 5).

TABLE 5

| Composition | % Carbon | % Hydrogen | % Nitrogen | % Sulfur |
|---|---|---|---|---|
| 17-FEAG-HQ of Example 10A | 59.58 | 7.21 | 6.81 | 0.45 |
| 17-FEAG-HQ of Example 10B | 59.97 | 7.77 | 6.30 | <0.05 |

TABLE 6

| | Percent Purity of 17-FEAG | |
|---|---|---|
| Composition | T = 0 Days | T = 21 Days |
| 17-FEAG-HQ of Example 10A | 99 | 96 |
| 17-FEAG-HQ of Example 10B | 97 | 0 |

Example 11

Preparation of 17-allylamino-geldanamycin hydroquinone (17-AAG-HQ)

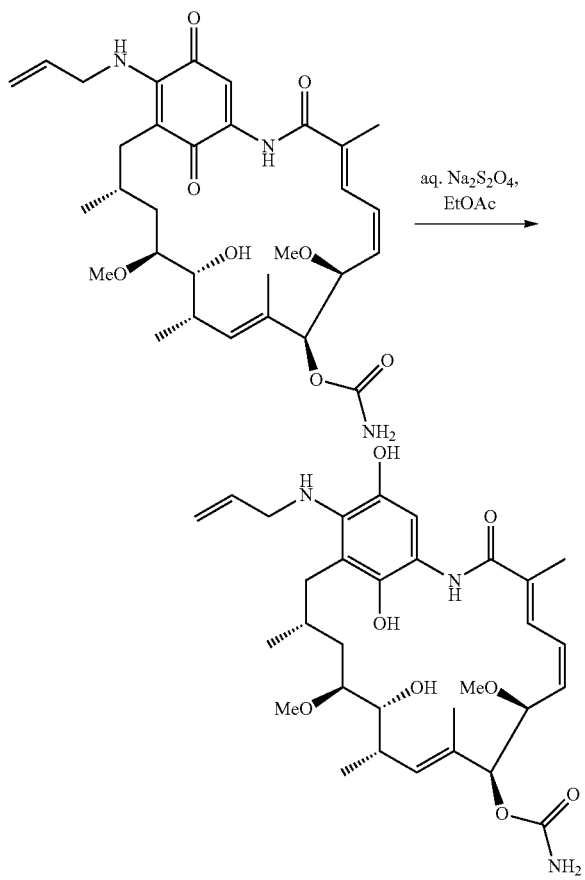

Example 11A. To a solution of 17-allylamino-geldanamycin (17-AAG) (3.03 grams, 5.17 mmol, 1.0 equiv) in EtOAc (60 mL) at 22° C. was added sodium hydrosulfite ($Na_2S_2O_4$) (25 g in 125 mL; 1.1 M). The biphasic mixture was stirred vigorously until the purple mixture turned yellow (60 min) and a precipitate formed in the organic layer (60 h). The organic layer was filtered and the precipitate was washed with several aliquots of ethyl acetate (25 mL, 3×) and water (25 mL, 3×). The organic filtrate was reserved for use in the preparation of 17-AAG-HQ of Example 11B (see below). The washed precipitate was collected and dried under vacuum to obtain 17-allylamino-geldanamycin hydroquinone (17-AAG-HQ) of Example 11A as a bright yellow solid (654.0 mg, 1.11 mmol, 21.5% Yield). Percent Purity (HPLC-UV): 98%.

Example 11B. To the organic filtrate from Example 11A was added an aqueous solution of sodium hydrosulfite ($Na_2S_2O_4$) (20 g in 100 mL; 1.1M). The biphasic mixture was stirred vigorously for 1 h to ensure full conversion to 17-AAG-HQ. The yellow organic layer was separated and washed with 100 mL NaCl and dried with $MgSO_4$. The organic solution was filtered and the drying agent was rinsed with 100 mL EtOAc. The organic layers were combined and the solution was concentrated under reduced pressure to 17-allylamino-geldanamycin hydroquinone (17-AAG-HQ) of Example 11B as a rusty yellow solid (2.25 grams, 3.38 mmol, 74.0%). Percent Purity (HPLC-UV): 97%.

Figure 12:
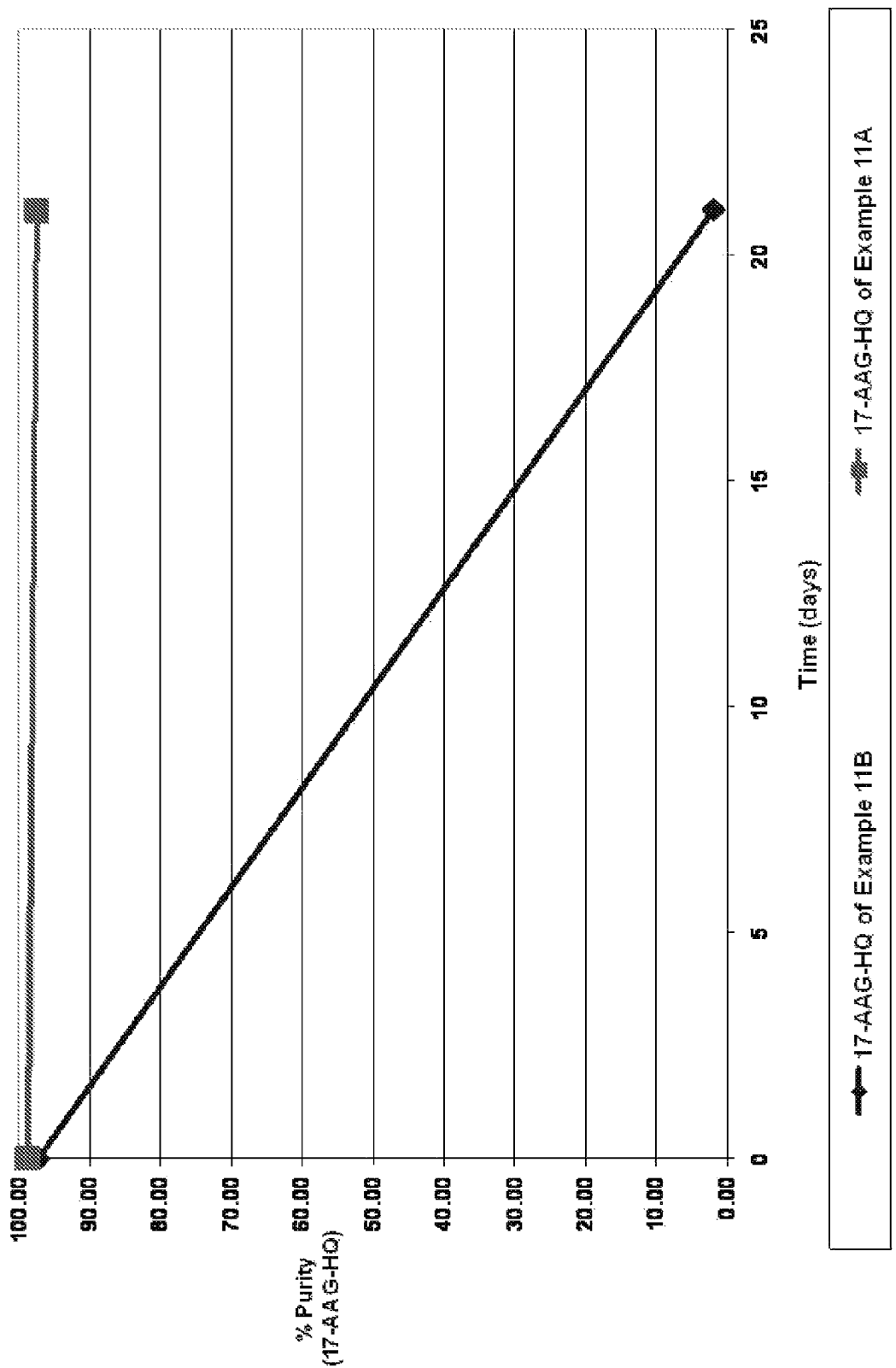
FIG. 12 is a graph depicting the stability of 17-AAG-HQ of Example 11A and 11B at 40° C. and 75% relative humidity (RH).

Comparison of Examples 11A and 11B. When compared to 17-AAG-HQ of Example 11B, 17-AAG-HQ of Example 11A shows greater stability over a period of time when kept at 40° C. and 75% relative humidity (RH) (see FIG. 12 and Table 8). The greater stability can be attributed to a higher sulfur content of 17-AAG-HQ of Example 11A as compared to the sulfur content of 17-AAG-HQ of Example 11B (See Table 7).

TABLE 7

| Composition | % Carbon | % Hydrogen | % Nitrogen | % Sulfur |
|---|---|---|---|---|
| 17-AAG-HQ of Example 11A | 58.38 | 7.10 | 6.15 | 2.08 |
| 17-AAG-HQ of Example 11B | 61.32 | 7.65 | 6.13 | <0.05 |

TABLE 8

| | Percent Purity of 17-AAG | |
|---|---|---|
| Composition | T = 0 Days | T = 21 Days |
| 17-AAG-HQ of Example 11A | 99 | 97 |
| 17-AAG-HQ of Example 11B | 97 | 2 |

Example 12

Solubilizing or Suspending Agents

Solvents (2 mL) were pipetted out into labeled vials (Table 4). After purging the headspace with argon, the solvent vials were chilled at 4° C. for 1 hour. 17-AG-HQ of Example 2 (10 mg) was added each solvent vial and headspace was purged again with argon. The vials were checked for color change for up to one hour. Color change is an indication of stability: 17-AG-HQ is yellow while 17-AG is pink, thus a color change from yellow to pink would indicate oxidation of 17-AG-HQ to 17-AG. The results of this experiment are summarized in Table 9 below. This listing of suitable solvents or suspending agents is also applicable for solvating/suspending the hydroquinones of Examples 3-6, 8, 10 or 11.

TABLE 9

| Solvents/Suspending Agents | Observations |
|---|---|
| Ethanol | Dissolves with no color change |
| Dichloromethane | Dissolves with no color change |
| Acetone | Dissolves with no color change |
| Toluene | Dissolves with no color change |
| Mineral Oil | Suspends with no color change |
| Xylene | Dissolves with no color change |
| Methanol | Dissolves with color change to red |

TABLE 9-continued

| Solvents/Suspending Agents | Observations |
|---|---|
| Propylene Glycol | Dissolves with color change to rusty brown |
| DMSO:Acetonitrile:TFA (80:20:0.1) | Dissolves with color change to rusty brown |

Example 13

Formulations 17-AG-HQ of Example 2

(A) NaHSO$_3$ and Sugars

Different solutions were prepared by vortexing a mixture of aqueous sodium bisulfite (3.5 mL; 1 g in 100 mL water) and various sugars (250 mg). The solutions were kept in the refrigerator at 4° C. for 30 min. 100 mg of 17-AG-HQ of Example 2 was then added to each solution and dissolved by vortexing. The resulting solutions were kept in the refrigerator at −80° C. for 4 hrs and then lyophilized for 48 hrs to provide various 17-AG-HQ formulations. For comparative purposes, a formulation was prepared according to the method above, but omitting the sugar (i.e., sodium bisulfate only). Exemplary formulations of 17-AG-HQ of Example 2 are provided in Table 10.

TABLE 10

| Formulations | NaHSO$_3$ | Sugar:17-AG-HQ | Sugar | 17-AG-HQ | Appearance |
|---|---|---|---|---|---|
| Lactose Anhydrous | 3.5 mL | 4:1M | 250 mg | 100 mg | rusty yellow powder |
| Lactose Monohydrate | 3.5 mL | 4:1M | 250 mg | 100 mg | rusty yellow powder |
| Trehalose | 3.5 mL | 4:1M | 250 mg | 100 mg | rusty yellow powder |
| Hydroxypropyl gamma CD | 3.5 mL | 1:1M | 250 | 100 mg | rusty yellow powder |
| NaHSO$_3$ only (no sugar) | 3.5 mL | — | none | 100 mg | yellow powder |

(B) NaHSO$_3$ and Polymers

A solution was prepared by adding 300 mg polyvinyl alcohol (PVA) and 3 mg Tween 80 to 10 mL of aqueous sodium bisulfite (1 g in 100 mL water) and stirring the solutions at 70° C. for 1 hr. 100 mg of 17-AG-HQ of Example 2 was then added to 3.5 mL of the solution and dissolved by vortexing. The solution was kept in the refrigerator at −80° C. for 4 hrs and then lyophilized for 48 hrs. This exemplary polymer formulation comprising a mixture of PVA, Tweeen-80 and 17-AG-HQ of Example 2 is summarized in Table 11.

TABLE 11

| Formulations | NaHSO$_3$ | Polymer: 17-AG-HQ | Polymer | 17-AG-HQ | Appearance |
|---|---|---|---|---|---|
| NaHSO$_3$/polymer (no sugar) | 3.5 mL | 3% w/v PVA (Tween 80-1% w/w of PVA) | 105 mg | 100 mg | white sponge/foam |

Figure 13:
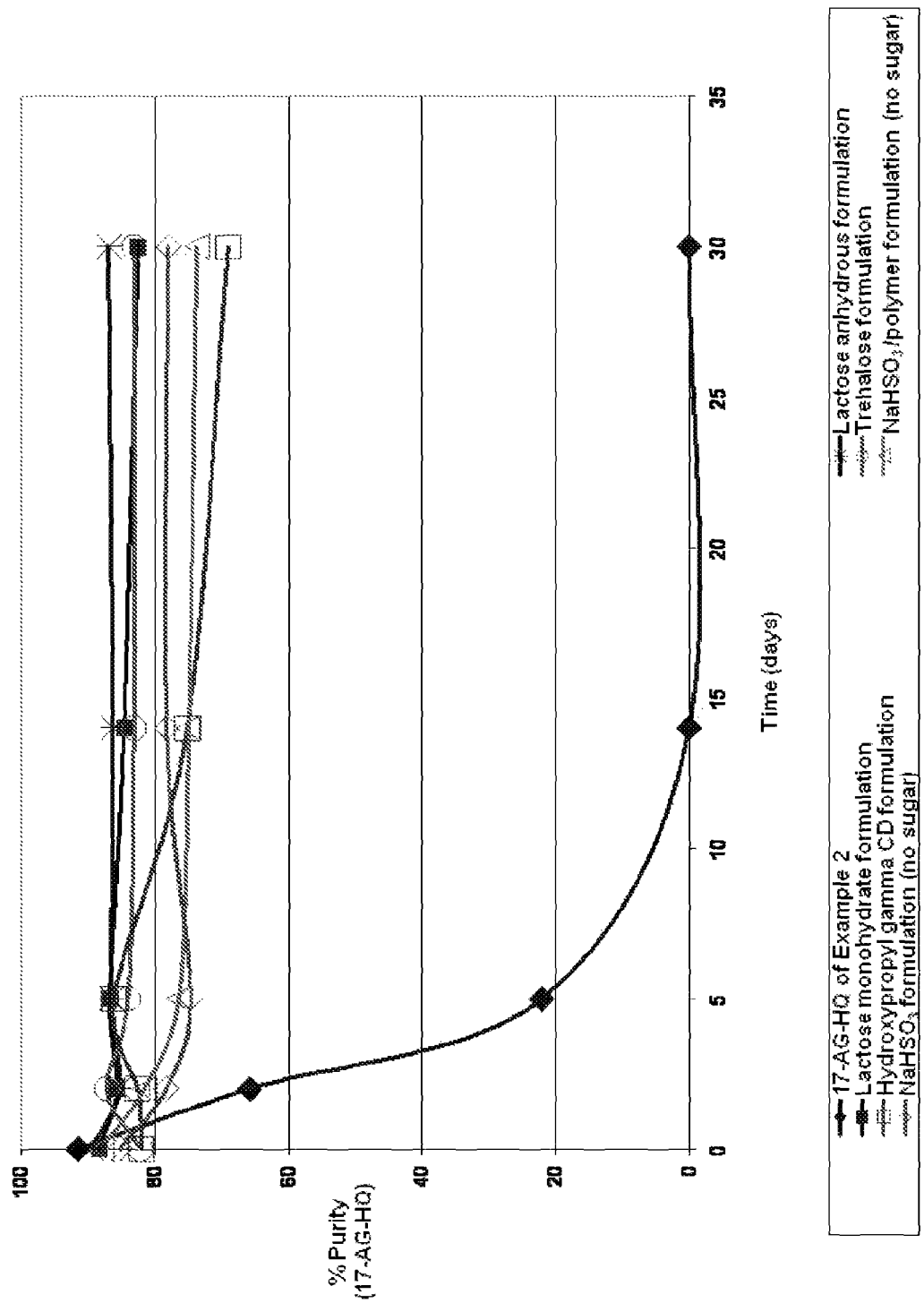
FIG. 13 is a graph depicting the stability of various formulations of 17-AG-HQ of Example 2 at 40° C. and 75% relative humidity (RH).

The stability data for the above-described formulations at 40° C. and 75% RH is shown in FIG. 13 and Table 12. As can be seen from the data, all formulations showed greater stability over a period of a month compared to the 17-AG-HQ of Example 2 not formulated.

TABLE 12

| | Percent Purity of 17-AG-HQ | | | | |
|---|---|---|---|---|---|
| Formulation | T = 0 Days | T = 2 Days | T = 5 Days | T = 14 Days | T = 30 Days |
| 17-AG-HQ of Example 2 | 92 | 66 | 22 | 0 | 0 |
| Lactose Anhydrous | 90 | 85 | 87 | 86 | 87 |
| Lactose Monohydrate | 88 | 86 | 87 | 85 | 83 |
| Trehalose | 82 | 87 | 84 | 83 | 83 |
| Hydroxypropyl-gamma-CD | 82 | 83 | 86 | 75 | 69 |
| NaHSO$_3$/polymer (no sugar) | 88 | 82 | 76 | 75 | 74 |
| NaHSO$_3$ only (no sugar) | 85 | 78 | 75 | 78 | 78 |

Example 14

Formulations OF 17-AG-HQ of Example 3

(A) NaHSO$_3$ and Sugar

Different solutions were prepared by vortexing a mixture of aqueous sodium bisulfite (3.5 mL; 1 g in 100 mL water) and various sugars (250 mg). The solutions were kept in the refrigerator at 4° C. for 30 min. 100 mg of 17-AG-HQ of Example 3 was added to each solution and dissolved by vortexing. The resulting solutions were kept in the refrigerator at −80° C. for 4 hrs and then lyophilized for 48 hrs. For comparative purposes, a formulation was prepared according to the method above, but omitting the sugar (i.e., sodium bisulfate only). Exemplary formulations of 17-AG-HQ of Example 3 are provided in Table 13.

TABLE 13

| Formulation | NaHSO$_3$ | Sugar:17-AG-HQ | Sugar | 17-AG-HQ | Appearance |
|---|---|---|---|---|---|
| Lactose Anhydrous | 3.5 mL | 4:1M | 250 mg | 100 mg | Yellow powder |
| Lactose Monohydrate | 3.5 mL | 4:1M | 250 mg | 100 mg | Yellow powder |
| Trehalose | 3.5 mL | 4:1M | 250 mg | 100 mg | Yellow powder |
| Hydroxy-propyl-gamma-CD | 3.5 mL | 1:1M | 250 mg | 100 mg | Yellow powder |
| NaHSO$_3$ only (no sugar) | 3.5 mL | none | none | 100 mg | Yellow powder |

Figure 14:
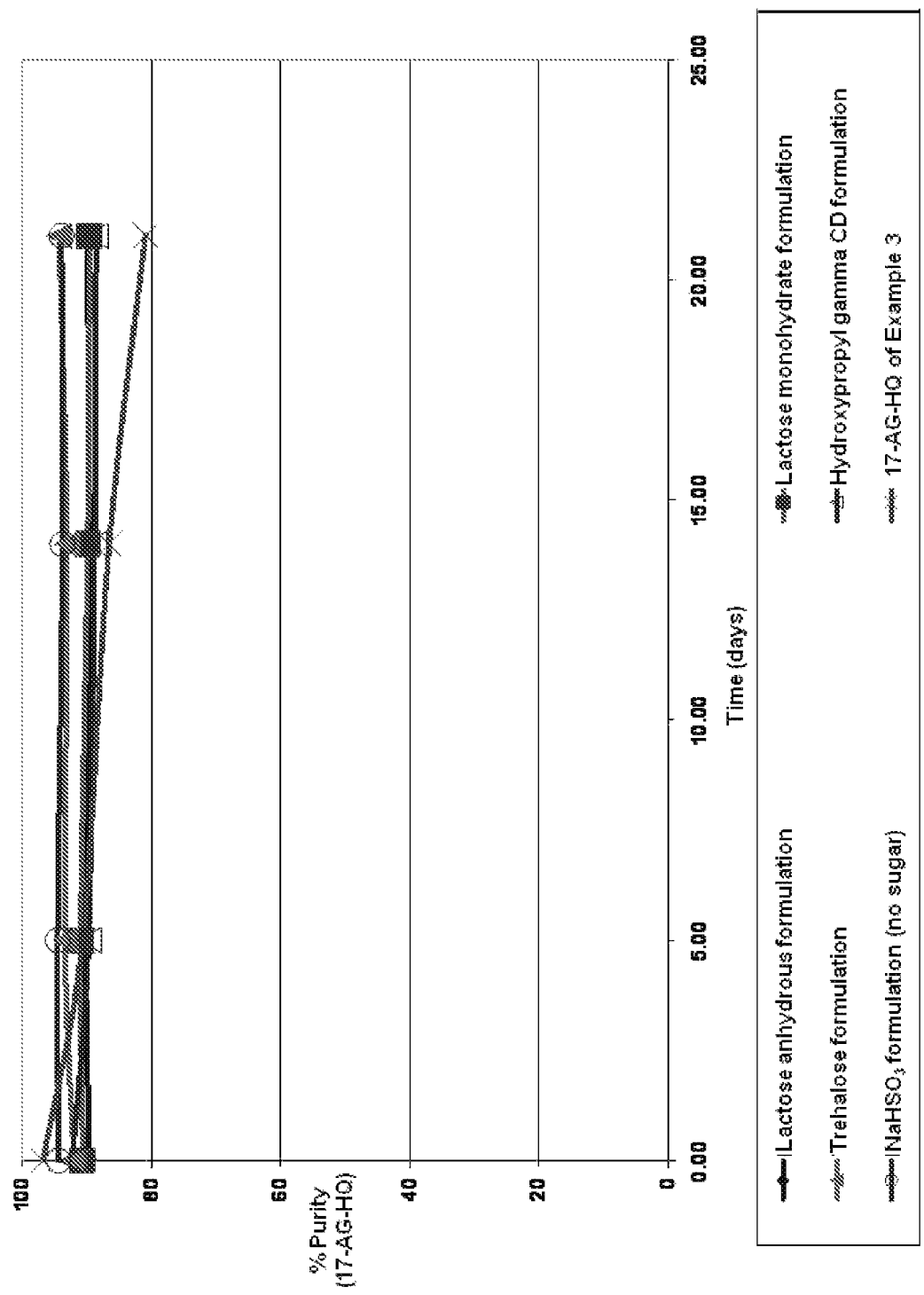
FIG. 14 is a graph depicting the stability of various formulations of 17-AG-HQ of Example 3 at 40° C. and 75% relative humidity (RH).

The stability data for the 17-AG-HQ formulations at 40° C. and 75% RH is shown in FIG. 14 and Table 14. As can be seen from the data, all formulations showed greater stability when compared to 17-AG-HQ of Example 3 not formulated.

TABLE 14

| | Percent Purity of 17-AG-HQ | | | |
|---|---|---|---|---|
| Formulation | T = 0 Days | T = 5 Days | T = 14 Days | T = 21 Days |
| 17-AG-HQ of Example 3 | 97 | 91 | 87 | 81 |
| Lactose Anhydrous | 90 | 90 | 90 | 90 |
| Lactose Monohydrate | 91 | 91 | 90 | 90 |
| Trehalose | 92 | 93 | 93 | 94 |
| Hydroxypropyl-gamma-CD | 92 | 90 | 89 | 89 |
| NaHSO$_3$ only (no sugar) | 95 | 95 | 94 | 94 |

(B) NaHSO$_3$ and Mineral Oil

Sodium bisulfite (100 mg) was added to 10 mL of light mineral oil and homogenized for 5 minutes using a high shear homogenizer. The prepared suspension was pipetted (5 mL) into 20 mL scintillation glass vials to which 140 mg of 17-AG-HQ of Example 3 was added and the suspension was mixed by homogenizing for 5 minutes until the particles were dispersed in the oil. The particles in the oil suspension settled readily but could be easily redispersed on shaking.

Figure 15:
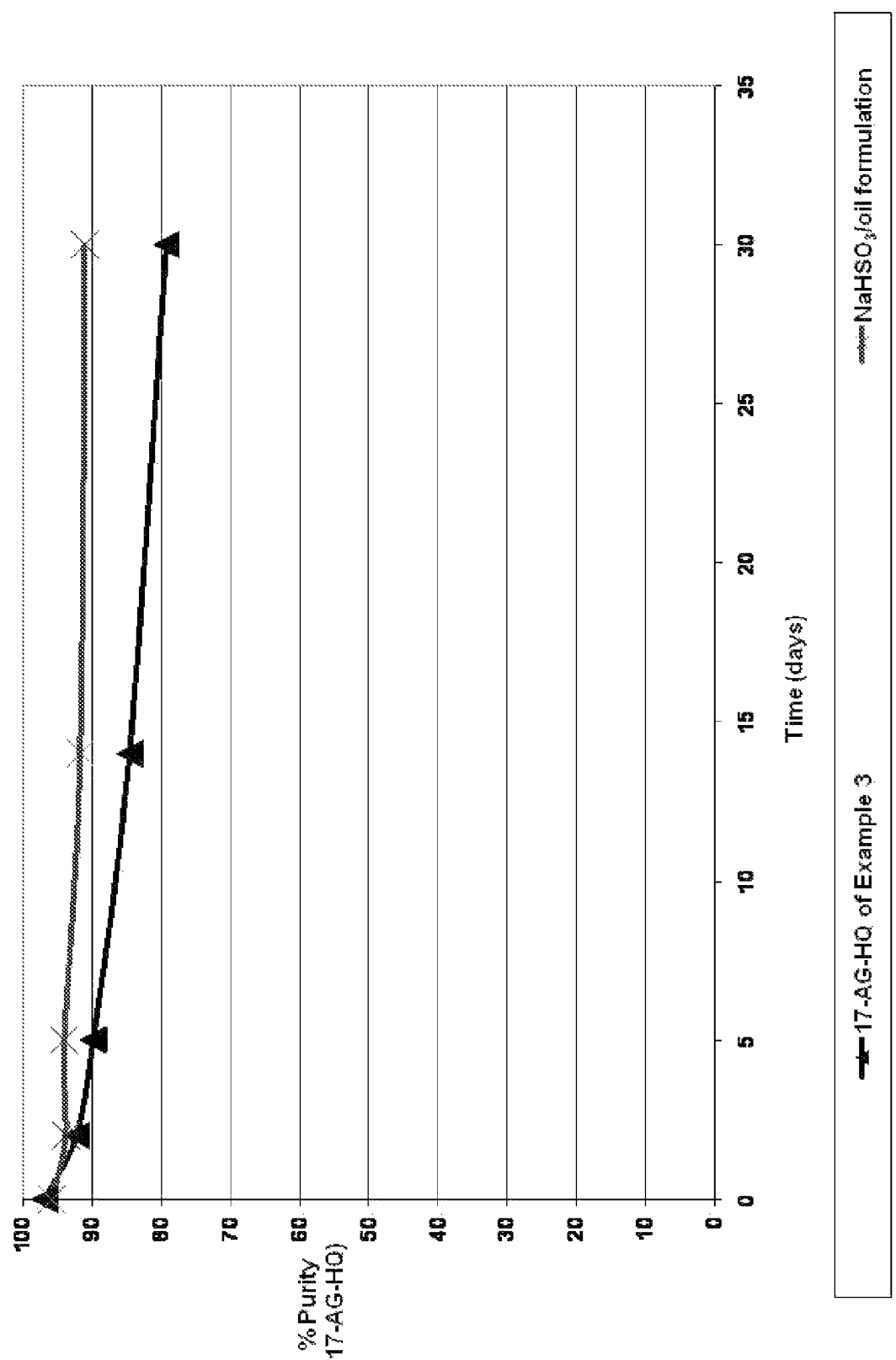
FIG. 15 is a graph depicting the stability of a NaHSO$_3$/mineral oil formulation of 17-AG-HQ of Example 3 at 40° C. and 75% relative humidity (RH).

The stability data for the mineral oil formulation at 40° C. and 75% RH is shown in FIG. 15 and Table 15.

TABLE 15

| | Percent Purity of 17-AG-HQ | | | |
|---|---|---|---|---|
| Formulation | T = 0 Days | T = 5 Days | T = 14 Days | T = 21 Days |
| 17-AG-HQ of Example 3 | 97 | 91 | 87 | 81 |
| NaHSO$_3$/Oil | 92 | 92 | 90 | 89 |

(C) NaHSO$_3$ and Polymer (Microencapsulated Formulation)

17-AG-HQ of Example 3 was microencapsulated in high molecular weight poly-vinyl alcohol polymer using the following oil-in-water emulsion method.

Sodium bisulfite (NaHSO$_3$) (100 mg) was dissolved in 10 mL of deionized water. To this solution, polyvinyl alcohol (PVA, 300 mg) and Tween 80 (3 mg) was added and dissolved by stirring at 70° C. for 1 hour. A mineral oil suspension of 17-AG-HQ of Example 3 was prepared by adding 50 mg of sodium bisulfite to 5 mL of light mineral oil and homogenizing for 5 minutes using a high shear homogenizer. 17-AG-HQ (70 mg) of Example 3 was added to the oil and the suspension was mixed by homogenizing for 5 minutes until the particles were dispersed in the oil.

An oil-in-water emulsion was prepared by gradually adding 1 mL of the suspension of 17-AG-HQ in mineral oil dropwise with a syringe to 3.5 mL of the PVA/Tween aqueous solution while stirring. The emulsion was stirred for an additional 5 minutes until small yellow microspheres separated in a clear solution. The microspheres were filtered and collected in a 20 mL scintillation vial which was kept in the refrigerator at −80° C. for 4 hrs and then lyophilized for 48 hrs. The desired product was obtained as rusty yellow sponge of microspheres.

Figure 16:
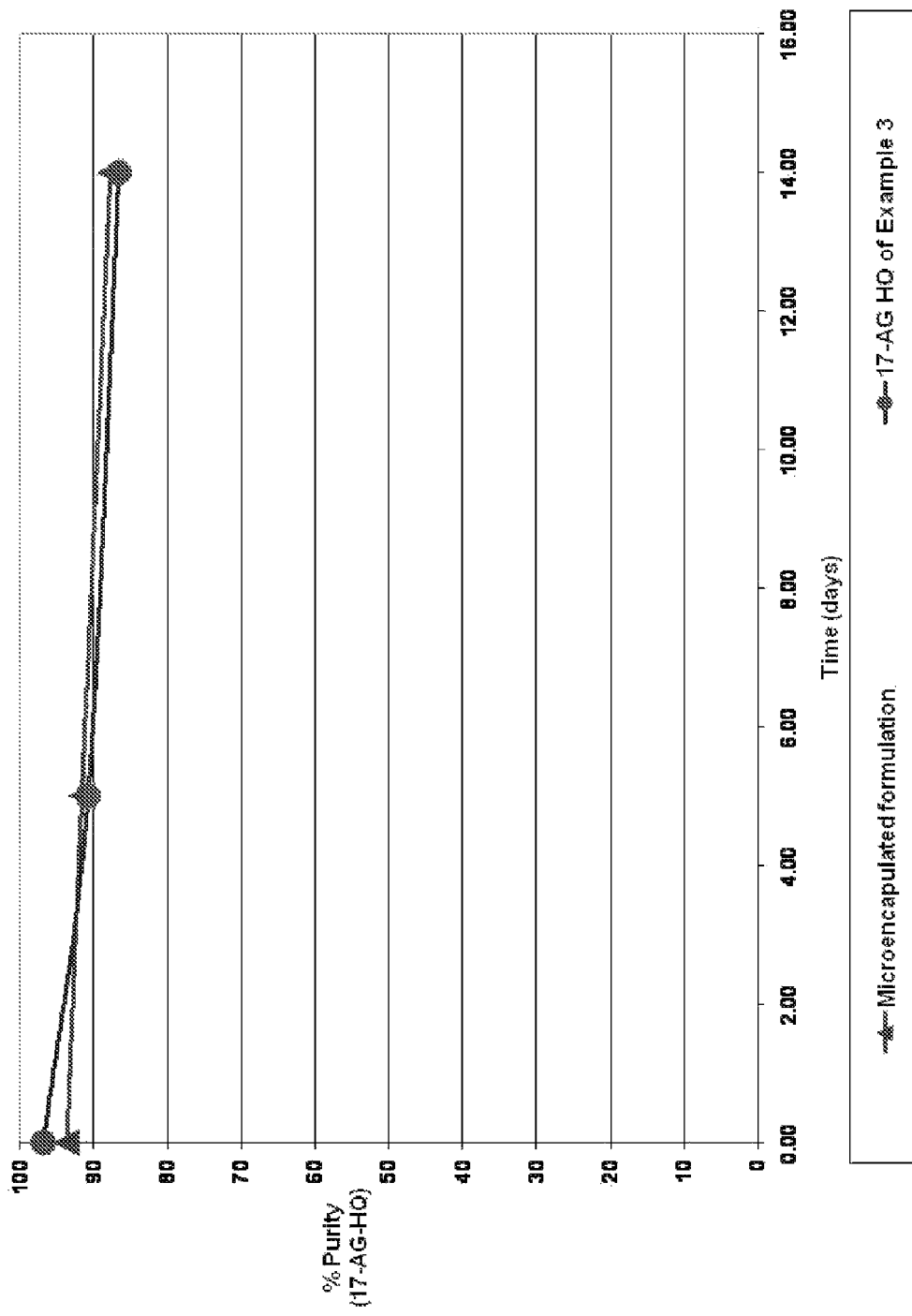
FIG. 16 is a graph depicting the stability of the microencapsulation formulation of 17-AG-HQ of Example 3 at 40° C. and 75% relative humidity (RH).
Figure 17:
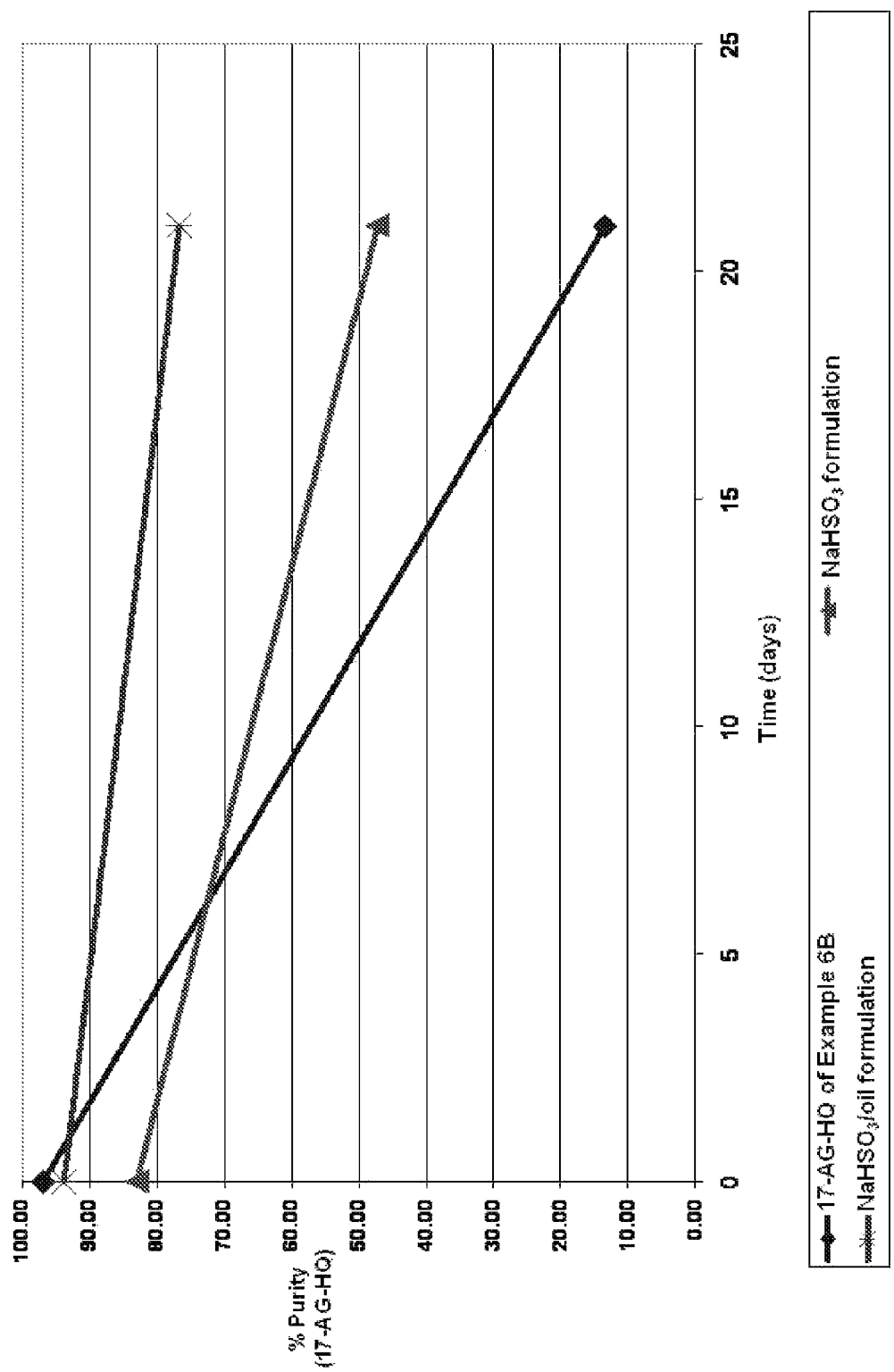
FIG. 17 is a graph depicting the stability of NaHSO$_3$ formulations of 17-AG-HQ of Example 6B at 40° C. and 75% relative humidity (RH).
Figure 18:
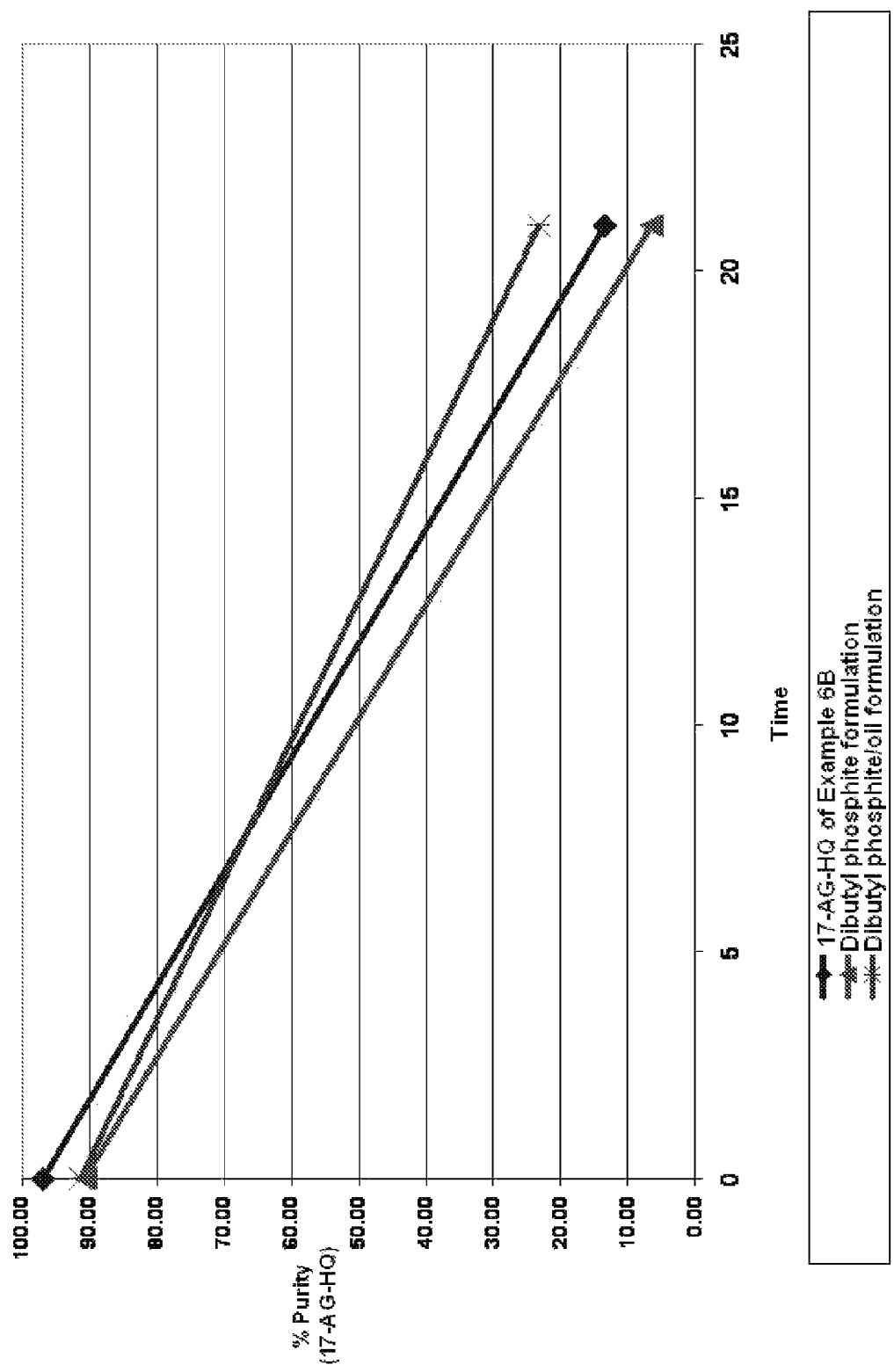
FIG. 18 is a graph depicting the stability of dibutyl phosphite formulations of 17-AG-HQ of Example 6B at at 40° C. and 75% relative humidity (RH).
Figure 19:
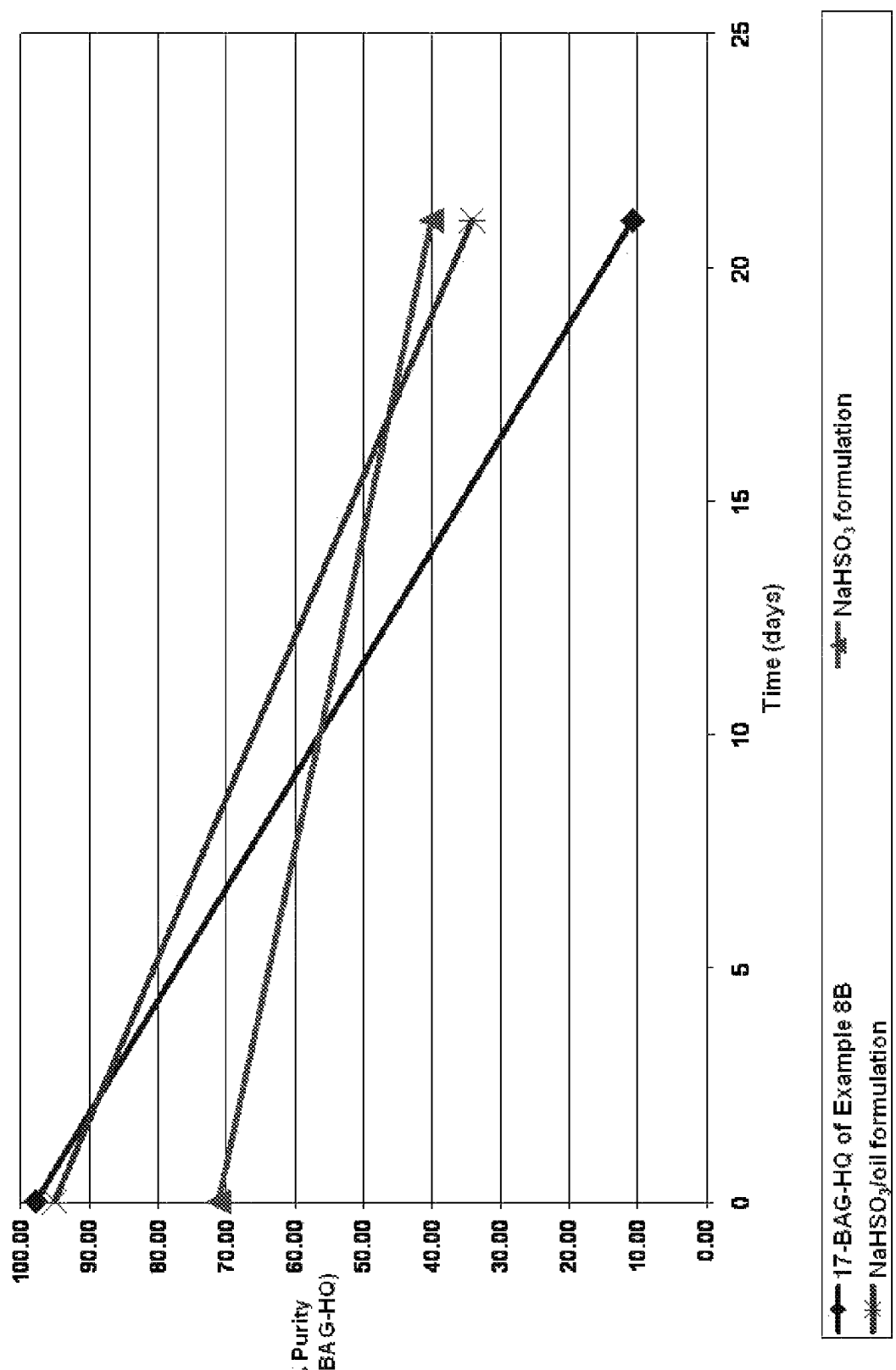
FIG. 19 is a graph depicting the stability of NaHSO$_3$ formulations of 17-BAG-HQ of Example 8B at at 40° C. and 75% relative humidity (RH).
Figure 20:
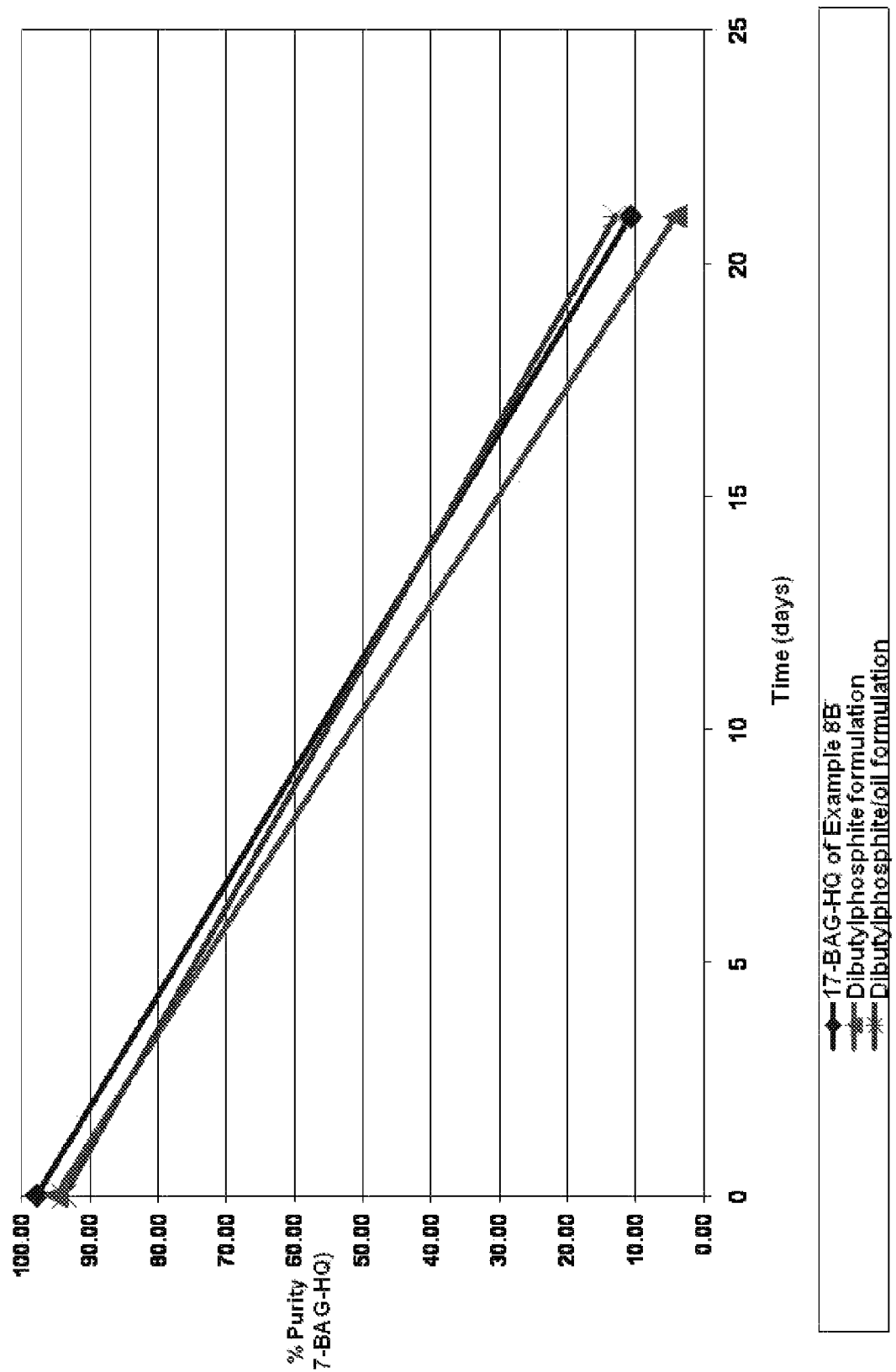
FIG. 20 is a graph depicting the stability of dibutyl phosphite formulations of 17-BAG-HQ of Example 8B at at 40° C. and 75% relative humidity (RH).
Figure 21:
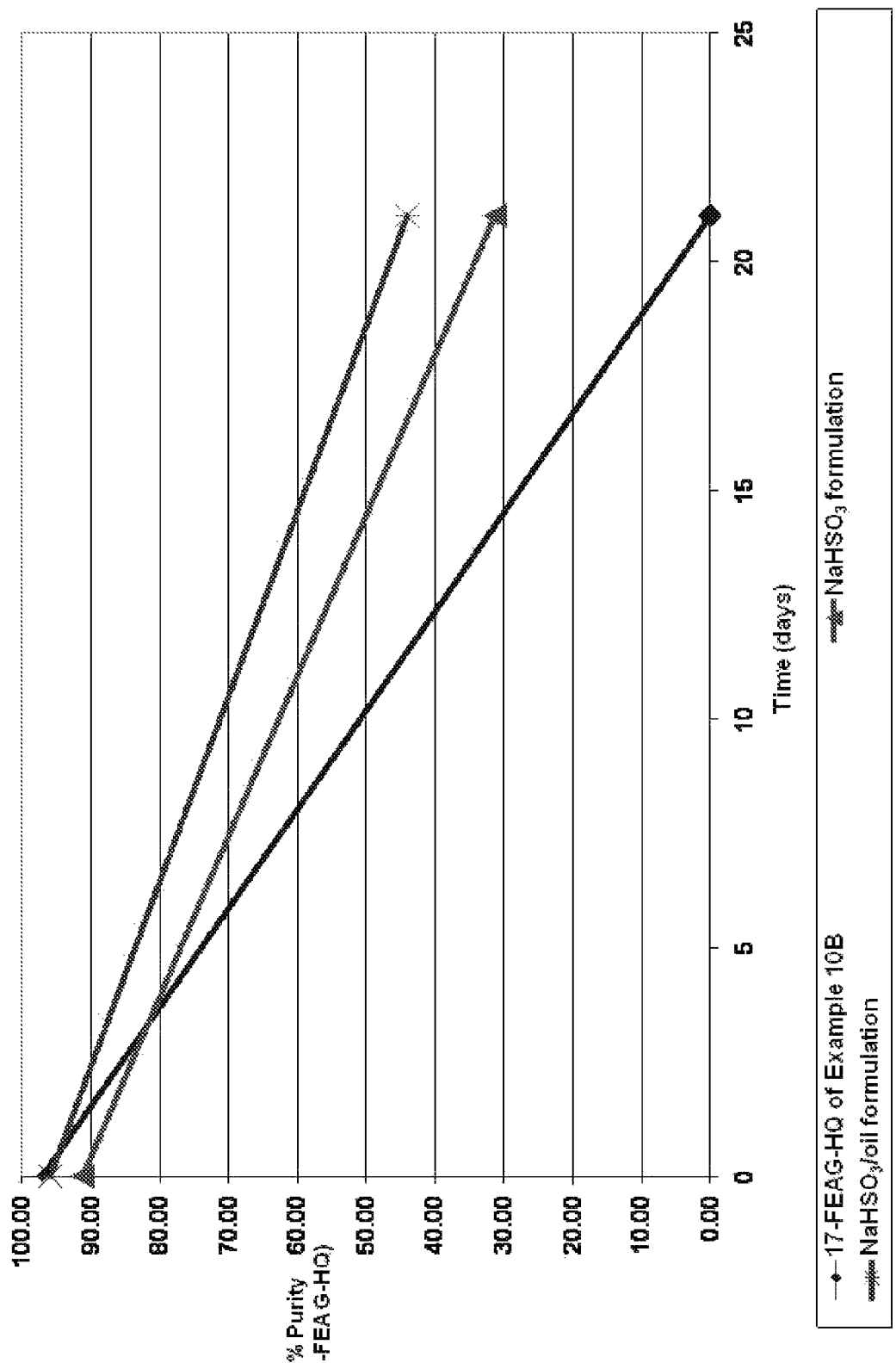
FIG. 21 is a graph depicting the stability of NaHSO$_3$ formulations of 17-FEAG-HQ of Example 10B at at 40° C. and 75% relative humidity (RH).
Figure 22:
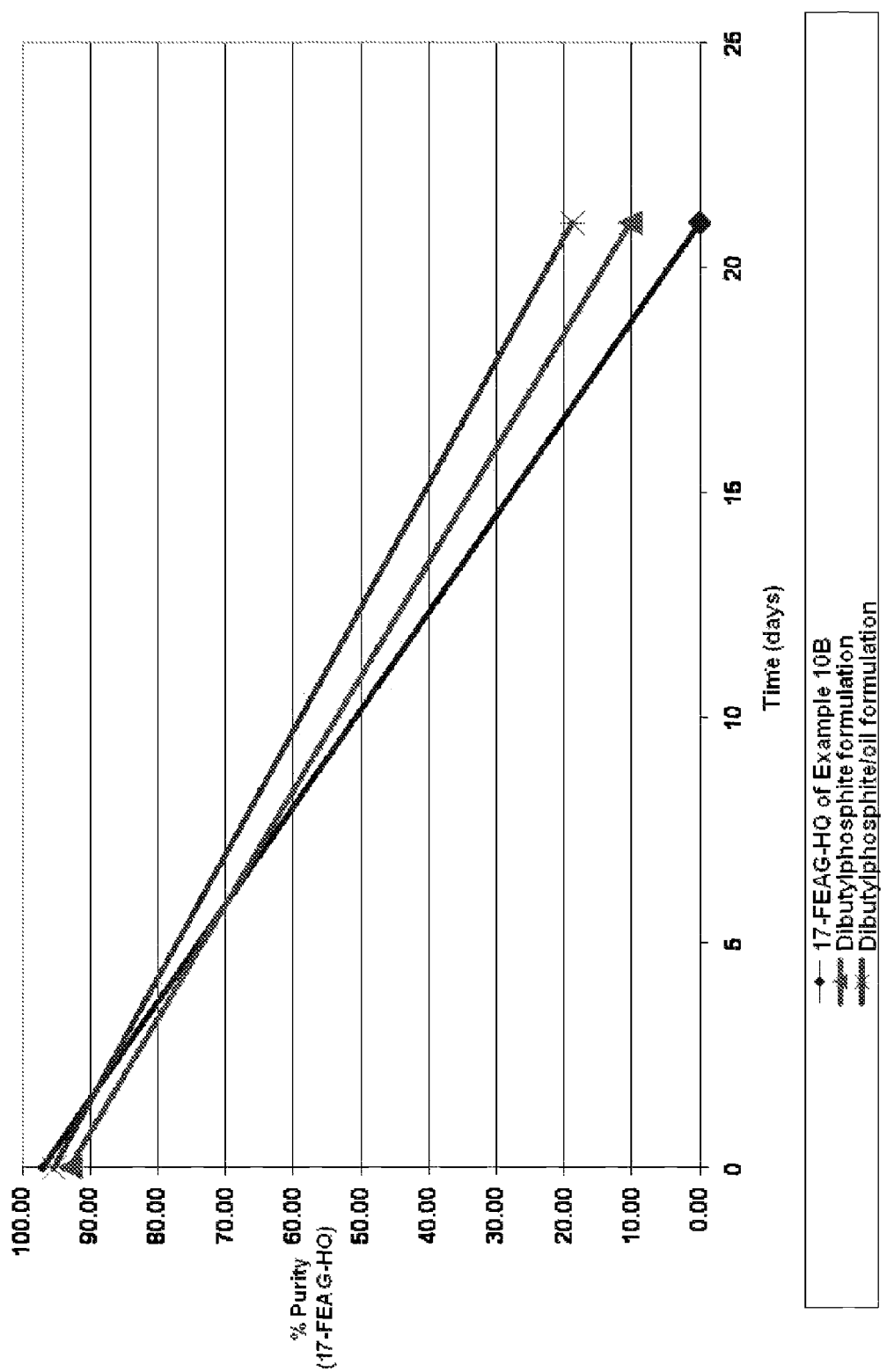
FIG. 22 is a graph depicting the stability of dibutyl phosphite formulations of 17-FEAG-HQ of Example 10B at at 40° C. and 75% relative humidity (RH).
Figure 23:
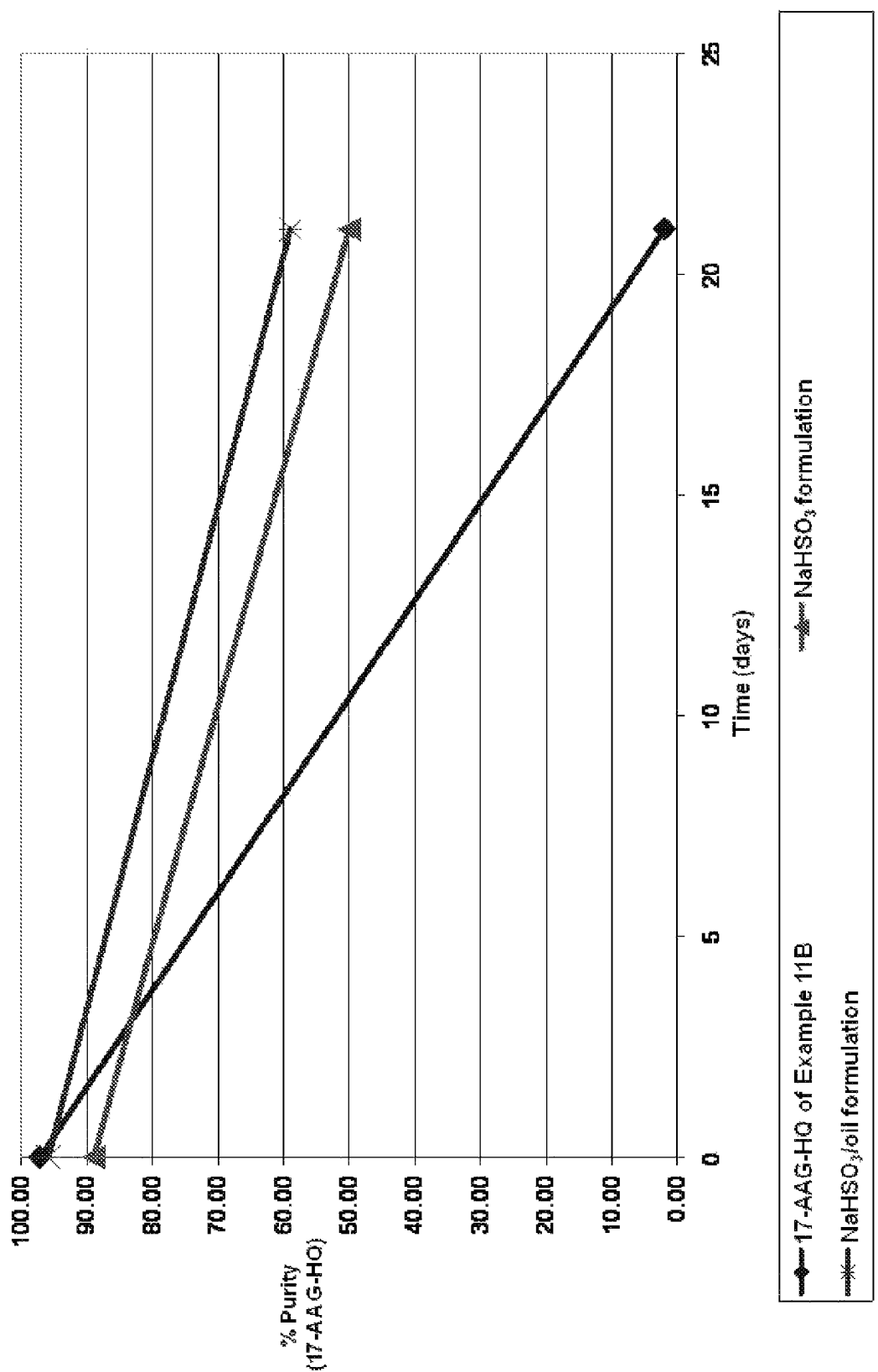
FIG. 23 is a graph depicting the stability of NaHSO$_3$ formulations of 17-AAG-HQ of Example 11B at 40° C. and 75% relative humidity (RH).
Figure 24:
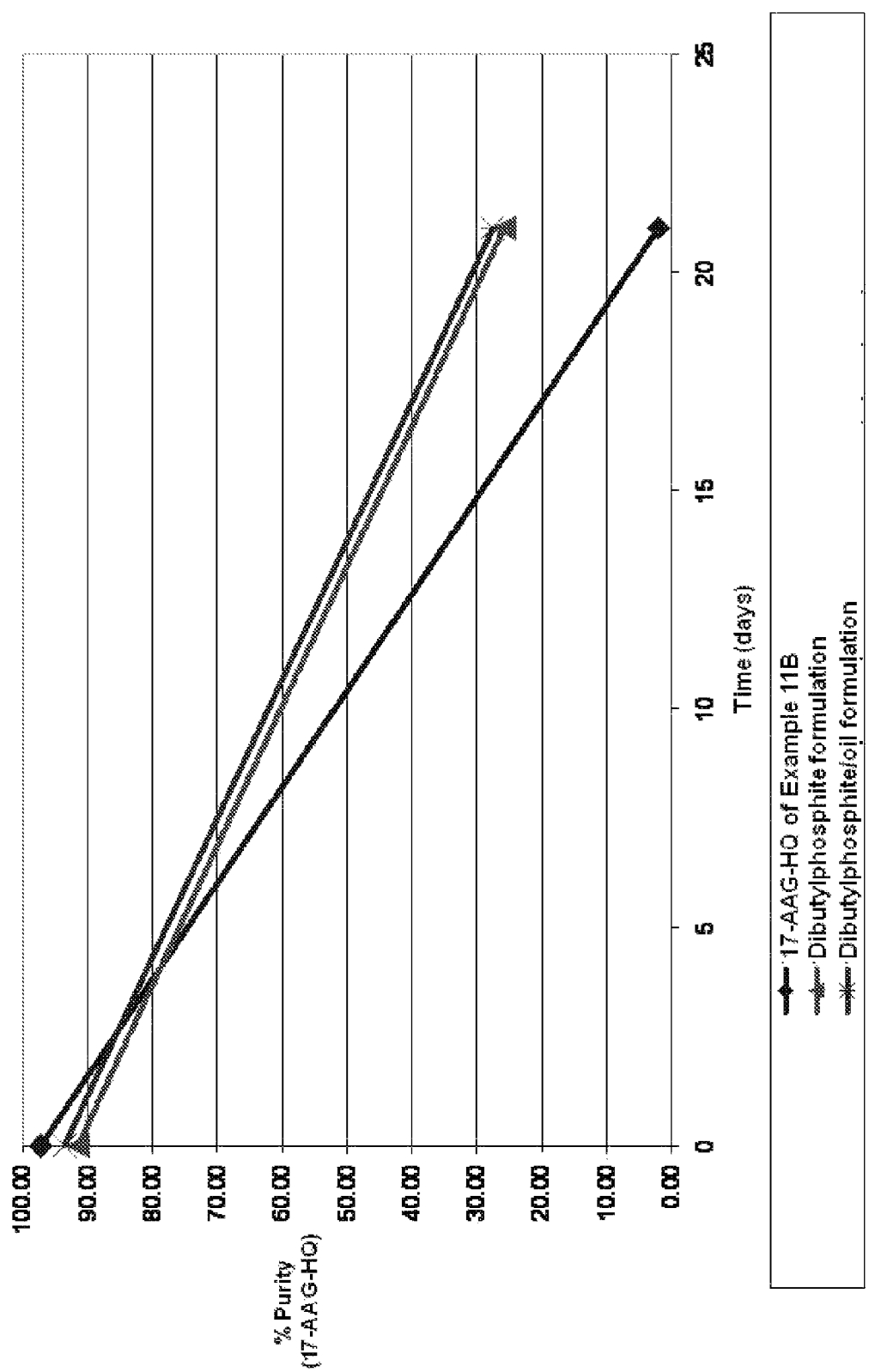
FIG. 24 is a graph depicting the stability of dibutyl phosphite formulations of 17-AAG-HQ of Example 11B at at 40° C. and 75% relative humidity (RH).

The stability data for the microencapsulated formulation of 17-AG-HQ of Example 3 at 40° C. at 75% RH is depicted in FIG. 16. As can be seen from the data, the formulation shows good stability under high temperature and humidity conditions.

Example 15

Formulations of Examples 6B, 8B, 10B and 11B (A) NaHSO$_3$

An aqueous sodium bisulfite solution (1 g in 100 mL water) was cooled on ice and purged with nitrogen for 20 minutes. To 3.5 mL of this solution was added 100 mg of a hydroquinone of Examples 6B, 8B, 10B or 11B, and the mixture dissolved by vortexing. Each reaction vial was purged with nitrogen, sealed and stored at −80° C. for 4 hrs and then lyophilized for 24 hrs. Each hydroquinone formulation was obtained as a rusty yellow powder.

The stability data for the formulations at 40° C. and 75% RH is shown in FIGS. 17, 19, 21, and 23 and Tables 16-19. As can be seen from the data, all the hydroquinone formulations showed greater stability compared to hydroquinones of Examples 6B, 8B, 10B or 11B not formulated.

(B) NaHSO$_3$ and Mineral Oil

A suspension of sodium bisulfate (NaHSO$_3$) (1 g) and light mineral oil (100 mL) was homogenized for 5 minutes using a high shear homogenizer. To 3.5 mL of this suspension was added 100 mg of a hydroquinone of Examples 6B, 8B, 10B or 11B, and the mixture was vortexed until the particles were evenly dispersed in oil. The particles in the oil suspension settled readily but could be redispersed upon shaking.

The stability data for the mineral oil formulations at 40° C. and 75% RH is shown in FIGS. 17, 19, 21, and 23 and Tables 16-19. As can be seen from the data, all formulations showed greater stability when compared to hydroquinones of Examples 6B, 8B, 10B or 11B not formulated.

(C) Dibutyl Phosphite

An aqueous dibutyl phosphite solution (1 mL of dibutyl phosphite in 100 mL water) was kept on ice and purged with nitrogen for 20 minutes. To 3.5 mL of this solution was added 100 mg of a hydroquinone of Examples 6B, 8B, 10B or 11B, and the mixture dissolved by vortexing. Each reaction vial was purged with nitrogen, sealed and stored at −80° C. for 4 hrs and then lyophilized for 24 hrs. Each hydroquinone formulation was obtained as a rusty yellow powder.

The stability data for the formulations at 40° C. and 75% RH is shown in FIGS. 18, 20, 22 and 24 and Tables 16-19. As can be seen from the data, formulations for 17-AG-HQ of Example 6B (FIGS. 18) and 17-BAG-HQ of Example 8B (FIG. 20) showed little to no improvement in stability when compared to the hydroquinones of 6B and 8B not formulated. Formulations for 17-FEAG-HQ of Example 10B (FIG. 22) and 17-AAG of Example 11B (FIG. 24) showed some improvement in stability (i.e., 10% and 25% improvement, respectively) compared to the hydroquinones of 10B and 11B not formulated.

(D) Dibutyl Phosphite and Mineral Oil

A suspension of dibutyl phosphite (1 mL) and light mineral oil (100 mL) was homogenized for 5 minutes using a high shear homogenizer. To 3.5 mL of this suspension was added 100 mg of a hydroquinone of Examples 6B, 8B, 10B or 11B, and the mixture was vortexed until the particles were evenly dispersed in oil. The particles in the oil suspension settled readily could be easily redispersed upon shaking.

The stability data for the mineral oil suspension at 40° C. and 75% RH is shown in FIGS. 18, 20, 22 and 24 and Tables 16-19. As can be seen from the data, the formulation for 17-BAG-HQ of Example 8B (FIG. 20) showed little improvement in stability when compared to the hydroquinone of 8B not formulated. Formulations for 17-AG-HQ of Example 6B (FIG. 18), 17-FEAG-HQ of Example 10B (FIGS. 22), and 17-AAG of Example 11B (FIG. 24) showed some improvement in stability (i.e., 10%, 20% and 30% improvement, respectively) compared to the hydroquinones of 6B, 10B and 11B not formulated.

TABLE 16

| Example 6B Formulations | Percent Purity of 17-AG-HQ | |
|---|---|---|
| | T = 0 Days | T = 21 Days |
| 17-AG-HQ of Example 6B | 97 | 13 |
| NaHSO$_3$ formulation | 83 | 47 |
| NaHSO$_3$/mineral oil formulation | 94 | 77 |
| dibutyl phosphite formulation | 91 | 6 |
| dibutyl phosphite/mineral oil formulation | 91 | 23 |

TABLE 17

| Example 8B Formulations | Percent Purity of 17-BAG-HQ | |
|---|---|---|
| | T = 0 Days | T = 21 Days |
| 17-BAG-HQ of Example 8B | 98 | 11 |
| NaHSO$_3$ formulation | 71 | 40 |
| NaHSO$_3$/mineral oil formulation | 95 | 34 |
| dibutyl phosphite formulation | 95 | 4 |
| dibutyl phosphite/mineral oil formulation | 94 | 13 |

TABLE 18

| Example 10B Formulations | Percent Purity of 17-FEAG-HQ | |
|---|---|---|
| | T = 0 Days | T = 21 Days |
| 17-FEAG-HQ of Example 10B | 97 | 0 |
| NaHSO$_3$ | 71 | 51 |
| NaHSO$_3$/mineral oil formulation | 96 | 44 |
| dibutyl phosphite formulation | 93 | 10 |
| dibutyl phosphite/mineral oil formulation | 95 | 19 |

TABLE 19

| Example 11B Formulations | Percent Purity of 17-AAG-HQ | |
|---|---|---|
| | T = 0 Days | T = 21 Days |
| 17-AAG-HQ of Example 11B | 97 | 2 |
| NaHSO$_3$ formulation | 89 | 50 |
| NaHSO$_3$/mineral oil formulation | 96 | 59 |
| dibutyl phosphite formulation | 92 | 26 |
| dibutyl phosphite/mineral oil formulation | 94 | 27 |

Equivalents

Those skilled in the art will recognize, or be able to ascertain using no more than routine experimentation, many equivalents to the specific embodiments of the invention described herein. Such equivalents form part of the invention, and are intended to be encompassed by the following claims.

We claim:

1. A solid composition, comprising a sulfite; and a compound of formula (I):

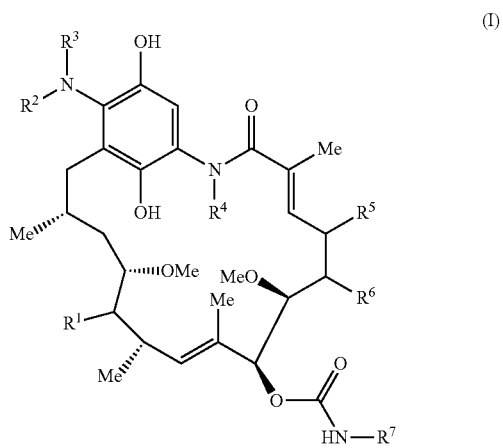

wherein:

R$^1$ is —H, —OR$^8$, —SR$^8$ —N(R$^8$)(R$^9$), —N(R$^8$)C(O) R$^9$, —N(R$^8$)C(O)OR$^9$, —N(R$^8$)C(O)N(R$^8$)(R$^9$), —OC(O)R$^8$, —OC(O)OR$^8$, —OS(O)$_2$R$^8$, —OS(O)$_2$ OR$^8$, —OP(O)$_2$OR$^8$ or —CN;

each of R$^2$ and R$^3$ is, independently, selected from —H, alkyl, alkenyl, alkynyl, cycloalkyl, cycloalkenyl, heterocyclyl, aryl, aralkyl, heteroaryl, heteroaralkyl, or —C(=O)CH$_3$; or R$^2$ and R$^3$ taken together with the nitrogen to which they are bonded represent a 3- to 8-membered heterocyclyl ring which contains 1 to 3 heteroatoms selected from O, N, S, and P;

R$^4$ is —H, alkyl, alkenyl or aralkyl;

R$^5$ and R$^6$ are each —H, or R$^5$ and R$^6$ taken together form a bond;

R$^7$ is —H, alkyl, alkenyl, alkynyl, cycloalkyl, cycloalkenyl, heterocyclyl, aryl, aralkyl, heteroaryl, or heteroaralkyl; and each instance of R$^8$ and R$^9$ is, independently, selected from —H, alkyl, alkenyl, alkynyl, cycloalkyl, cycloalkenyl, heterocyclyl, aryl, aralkyl, heteroaryl, or heteroaralkyl; or R$^8$ and R$^9$ taken together represent a 3 to 8 membered optionally substituted heterocyclyl ring which contains 1 to 3 heteroatoms selected from O, N, S, and P;

the sulfur content of the composition is greater than 0.5 percent as measured by Elemental Analysis; at least about 80% of the original amount of the compound of formula (I) remains after said composition is stored for 14 days at 40° C. and 75% relative humidity; and the sulfite is selected from the group consisting of potassium bisulfite, sodium bisulfite, calcium bisulfite, magnesium bisulfite, potassium metabisulfite, sodium metabisulfite, calcium metabisulfite, magnesium metabisulfite, potassium sulfite, sodium sulfite, calcium sulfite, magnesium sulfite, potassium hydrosulfite, sodium hydrosulfite, calcium hydrosulfite, magnesium hydrosulfite, and sodium formaldehyde sulfoxylate.

2. The composition according to claim 1, wherein the compound is of the formula (I-a):

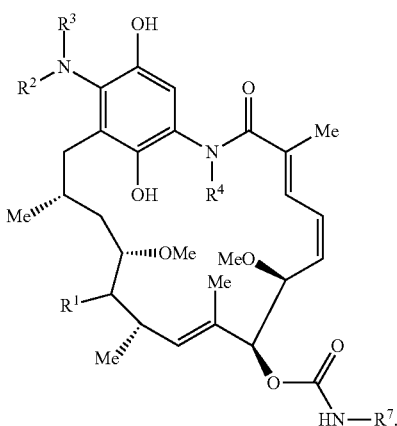

3. The composition according to claim 1, wherein the compound is of the formula (I-b):

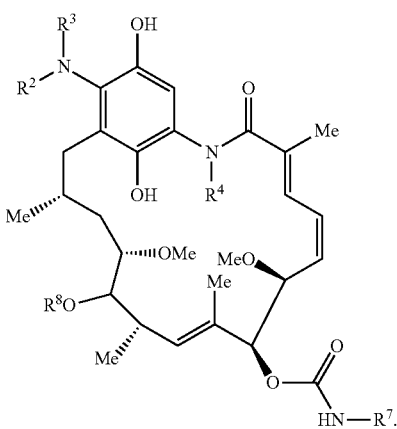

4. The composition according to claim 1, wherein the compound is of the formula (I-c):

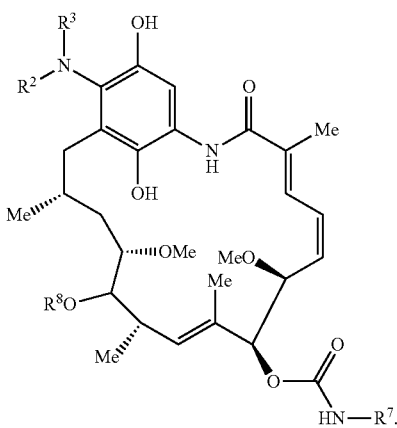

5. The composition according to claim 1, wherein the compound is of the formula (I-d):

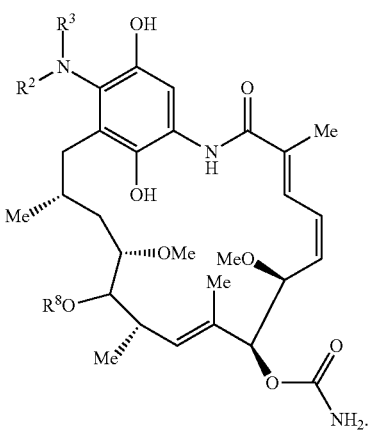

6. The composition of claim 5, wherein $R^2$ is selected from the group consisting of —H, alkyl, alkenyl, alkynyl, cycloalkyl, cycloalkenyl, heterocyclyl, aryl, aralkyl, heteroaryl and heteroaralkyl; and $R^3$ is —H.

7. The composition according to claim 6, wherein $R^2$ is —H.

8. The composition according to claim 1, wherein the compound of formula (I) is selected from the group consisting of:

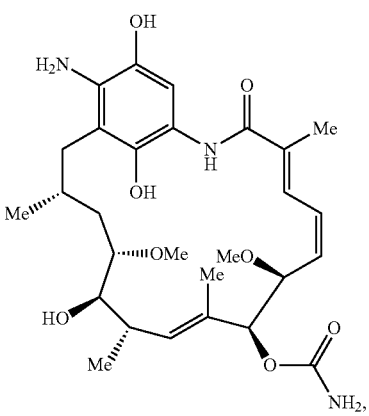

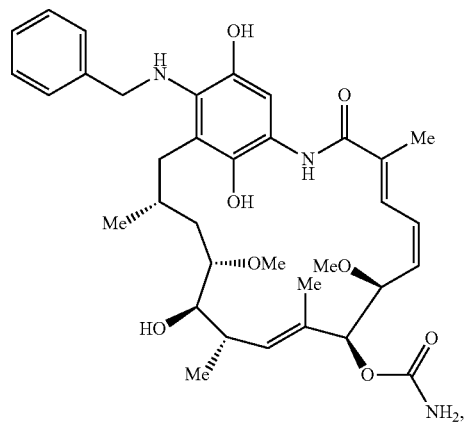

55
-continued
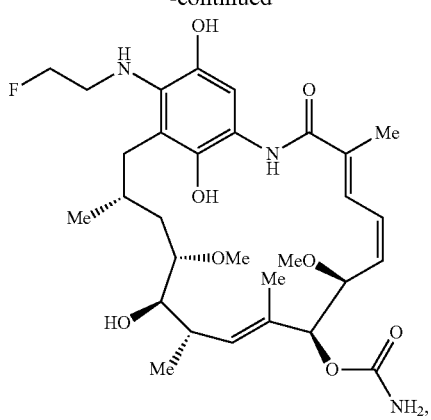
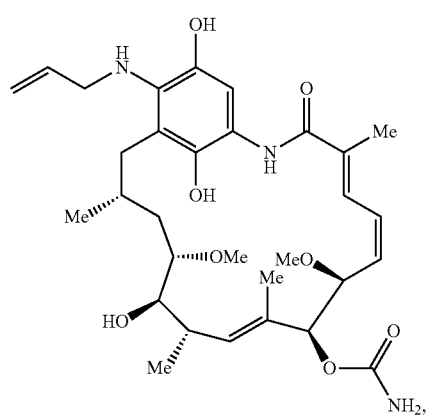
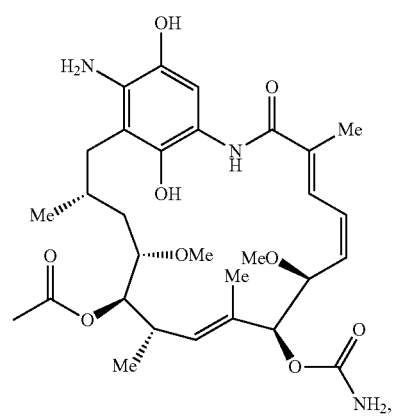
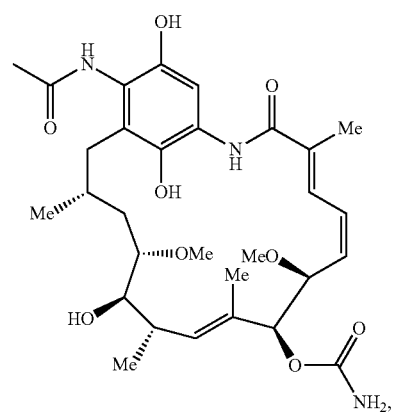
56
-continued
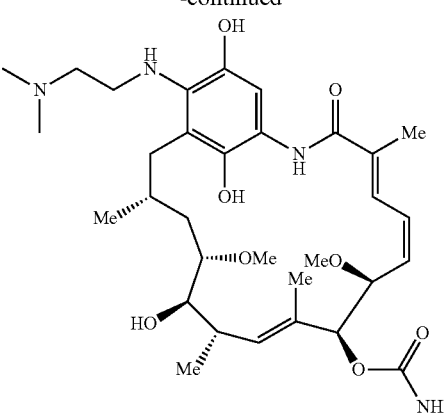
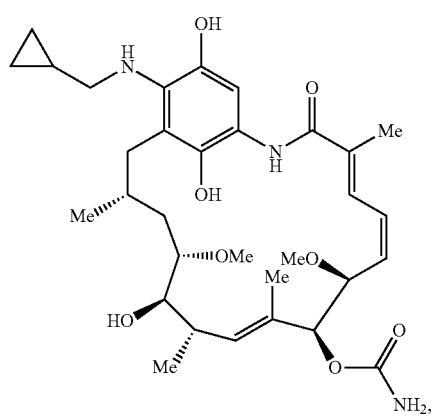
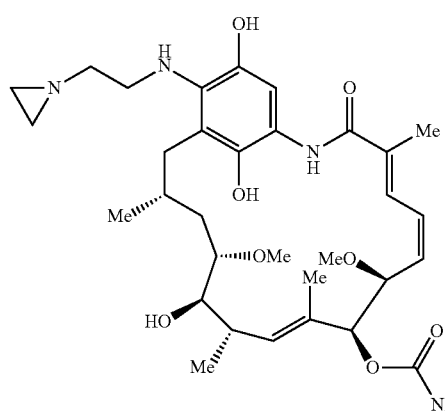
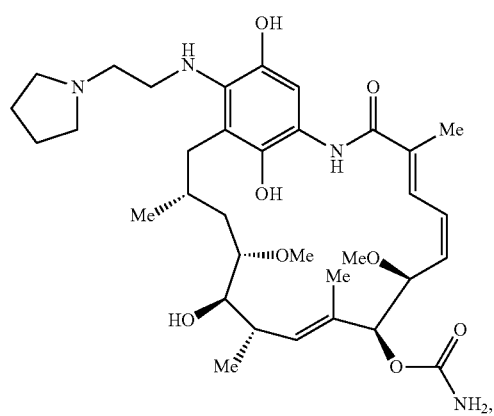

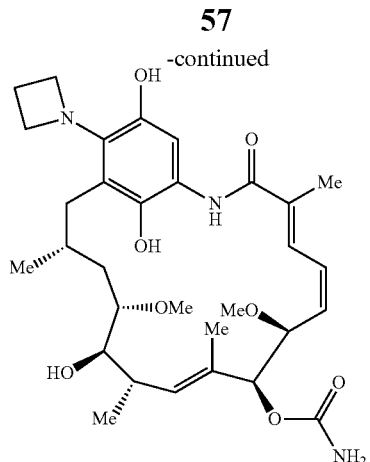

and

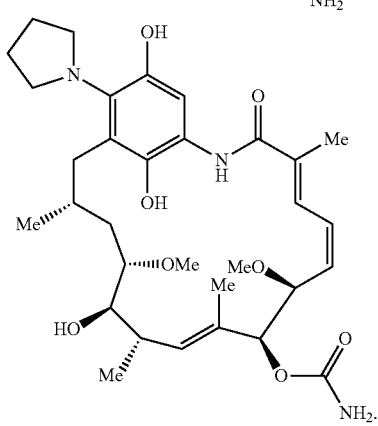

9. The composition according to claim 1, wherein the percent sulfur of the composition is greater than 1.0 percent as measured by Elemental Analysis.

10. A pharmaceutical formulation comprising a composition of claim 1; and a pharmaceutically acceptable excipient.

11. The formulation according to claim 10, wherein the pharmaceutically acceptable excipient is a sugar.

12. The formulation according to claim 11, wherein the sugar is selected from the group consisting of anhydrous lactose, lactose monohydrate, trehalose and hydroxypropyl-gamma-CD.

13. The formulation according to claim 10, wherein the pharmaceutically acceptable excipient is a polymer.

14. The formulation according to claim 13, wherein the polymer is polyvinyl alcohol.

15. The formulation according to claim 10, wherein the pharmaceutically acceptable excipient is a surfactant.

16. The formulation according to claim 15, wherein the surfactant is a Tween surfactant.

17. The formulation according to claim 10, wherein the pharmaceutically acceptable excipient is an antioxidant.

18. The formulation according to claim 10, wherein the pharmaceutically acceptable excipient is a solubilizing or suspending agent.

19. The formulation according to claim 18, wherein the solubilizing or suspending agents is selected from the group consisting of water, organic solvents, oils, and mixtures thereof.

20. The formulation according to claim 10, wherein the compound is of the formula (I-a):

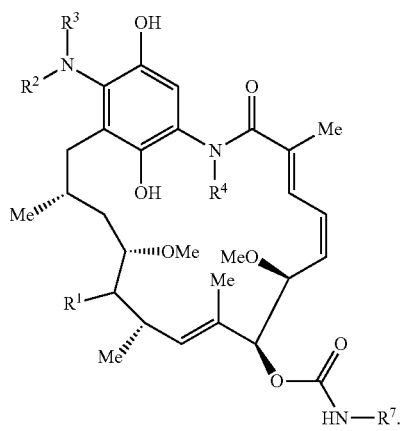

21. The formulation according to claim 10, wherein the compound is of the formula (I-b):

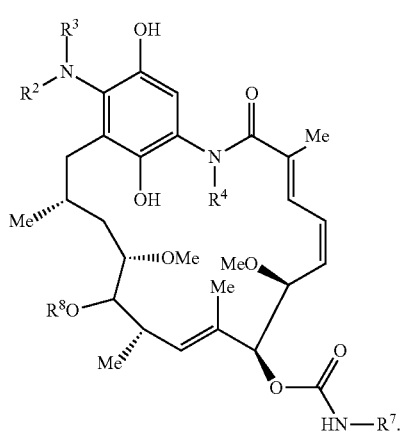

22. The formulation according to claim 10, wherein the compound is of the formula (I-c):

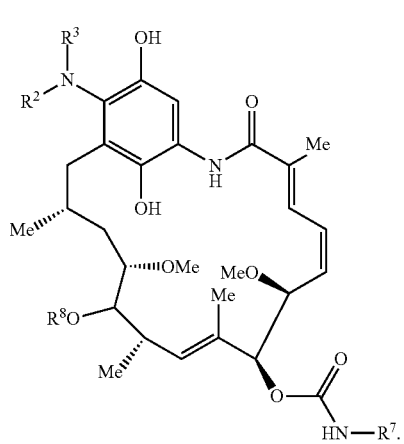

23. The formulation according to claim 10, wherein the compound is of the formula (I-d):

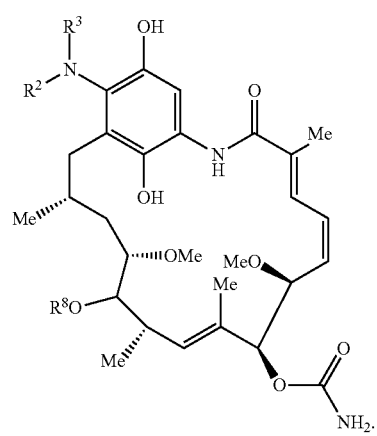
(I-d)
24. The formulation of claim 23, wherein R² is selected from the group consisting of —H, alkyl, alkenyl, alkynyl, cycloalkyl, cycloalkenyl, heterocyclyl, aryl, aralkyl, heteroaryl and heteroaralkyl; and R³ is —H.
25. The formulation according to claim 24, wherein R² is —H.
26. The formulation according to claim 10, wherein the compound of formula (I) is selected from the group consisting of:
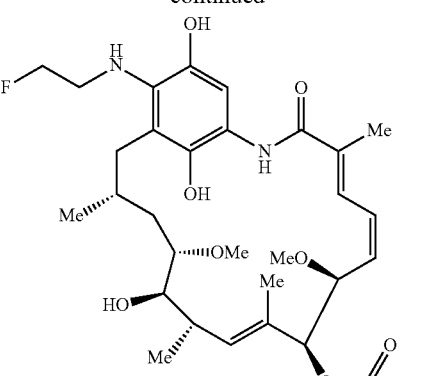
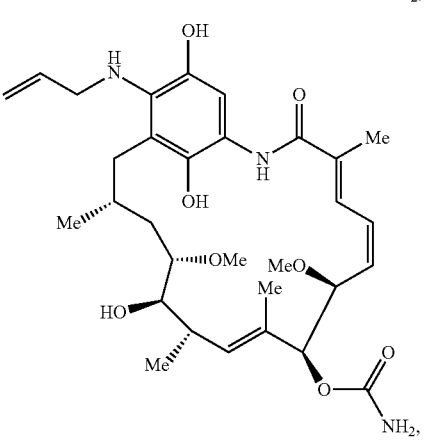
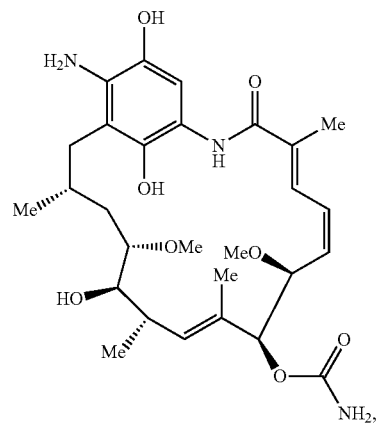
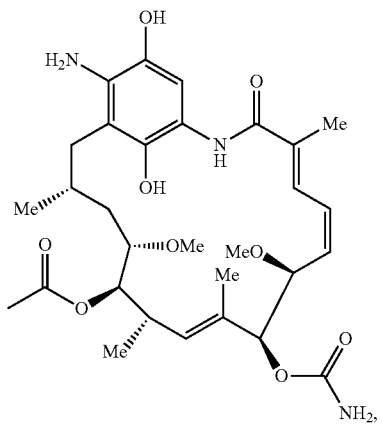
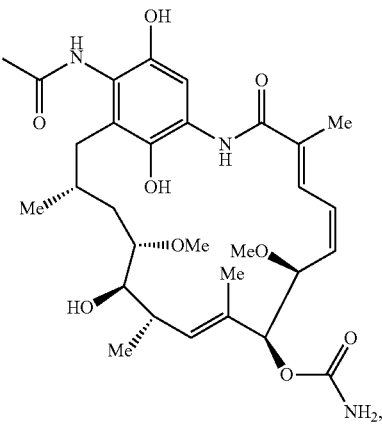

61
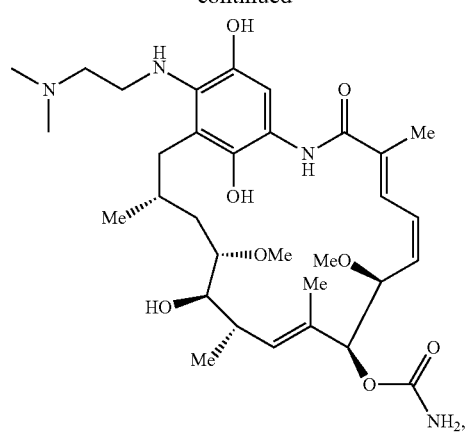
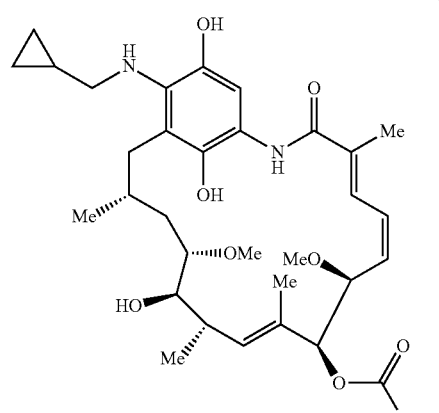
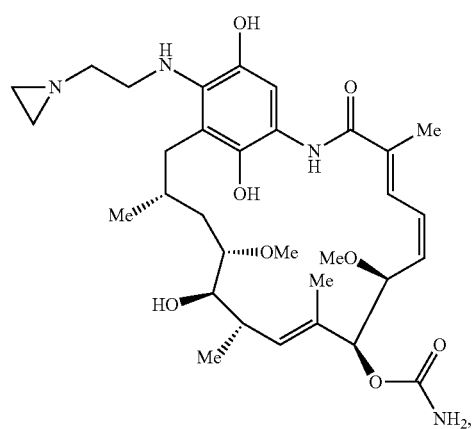
62
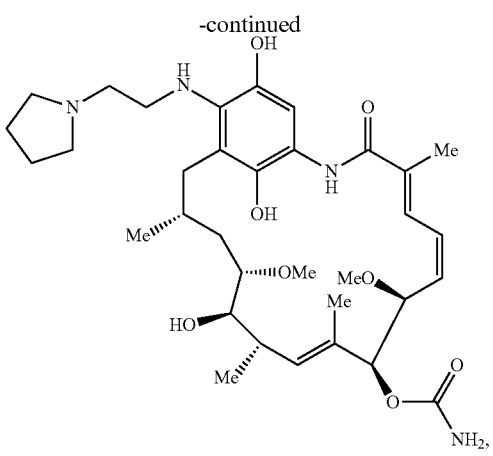
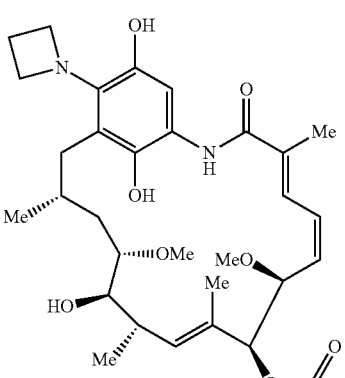
and
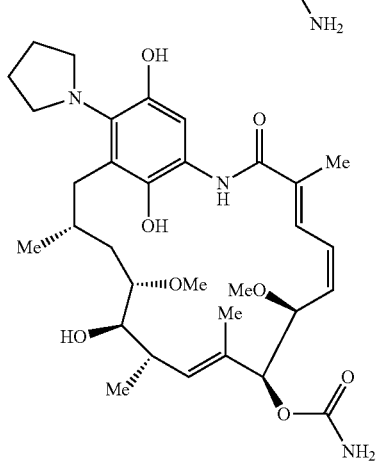
* * * * *